(12) United States Patent
Chen et al.

(10) Patent No.: US 7,625,724 B2
(45) Date of Patent: Dec. 1, 2009

(54) MAVS IN THE PREVENTION AND TREATMENT OF VIRAL DISEASES

(75) Inventors: Zhijian James Chen, Dallas, TX (US); Rashu Seth Bhargava, Dallas, TX (US); Lijun Sun, Dallas, TX (US); Xiao-Dong Li, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 294 days.

(21) Appl. No.: 11/509,924

(22) Filed: Aug. 25, 2006

(65) Prior Publication Data

US 2008/0003614 A1    Jan. 3, 2008

Related U.S. Application Data

(60) Provisional application No. 60/711,451, filed on Aug. 25, 2005.

(51) Int. Cl.
*C12P 19/34*    (2006.01)

(52) U.S. Cl. ..................................... 435/91.1

(58) Field of Classification Search ................ 435/91.1
See application file for complete search history.

(56) References Cited

U.S. PATENT DOCUMENTS

2006/0275794 A1 * 12/2006 Carrino et al. ................. 435/6

FOREIGN PATENT DOCUMENTS

WO    WO 2007/013391    *    2/2007

OTHER PUBLICATIONS

Crozat, K., and Beutler, B. (2004). TLR7: A new sensor of viral infection. Proc Natl Acad Sci U S A 101, 6835-6836.
Diebold, S. S., Kaisho, T., Hemmi, H., Akira, S., and Reis e Sousa, C. (2004). Innate antiviral responses by means of TLR7-mediated recognition of single-stranded RNA. Science 303, 1529-1531.
Freundt, E. C., and Lenardo, M. J. (2005). Interfering with interferons: Hepatitis C virus counters innate immunity. Proc Natl Acad Sci U S A 102, 17539-17540.
Hiscott, J., Grandvaux, N., Sharma, S., Tenoever, B. R., Servant, M. J., and Lin, R. (2003). Convergence of the NF-kappaB and interferon signaling pathways in the regulation of antiviral defense and apoptosis. Ann N Y Acad Sci 1010, 237-248.
Kaufmann, T., Schlipf, S., Sanz, J., Neubert, K., Stein, R., and Borner, C. (2003). Characterization of the signal that directs Bcl-x(L), but not Bcl-2, to the mitochondrial outer membrane. J Cell Biol 160, 53-64.
Kovacsovics, M., Martinon, F., Micheau, O., Bodmer, J. L., Hofmann, K., and Tschopp, J. (2002). Overexpression of Helicard, a CARD-containing helicase cleaved during apoptosis, accelerates DNA degradation. Curr Biol 12, 838-843.
Li, X. D., Sun, L., Seth, R. B., Pineda, G., and Chen, Z. J. (2005). Hepatitis C virus protease NS3/4A cleaves mitochondrial antiviral signaling protein off the mitochondria to evade innate immunity. Proc Natl Acad Sci U S A 102, 17717-17722.
McWhirter, S. M., Tenoever, B. R., and Maniatis, T. (2005). Connecting mitochondria and innate immunity. Cell 122, 645-647.
Schwer, B., Ren, S., Pietschmann, T., Kartenbeck, J., Kaehlcke, K., Bartenschlager, R., Yen, T. S., and Ott, M. (2004). Targeting of hepatitis C virus core protein to mitochondria through a novel C-terminal localization motif. J Virol 78, 7958-7968.
Seth, R. B., Sun, L., Ea, C. K., and Chen, Z. J. (2005). Identification and characterization of MAVS, a mitochondrial antiviral signaling protein that activates NF-kappaB and IRF 3. Cell 122, 669-682.
Xu. L G., Wang, Y. Y., Han, K. J., Li, L. Y., Zhai, Z., and Shu, H. B. (2005). VISA Is an Adapter Protein Required for Virus-Triggered IFN-beta Signaling. Mol Cell 19, 727-740.
Ye, H., Arron, J. R., Lamothe, B., Cirilli, M., Kobayashi, T., Shevde, N. K., Segal, D., Dzivenu, O. K., Vologodskaia, M., Yim, M., et al. (2002). Distinct molecular mechanism for initiating TRAF6 signalling. Nature 418, 443-447.

* cited by examiner

*Primary Examiner*—Ali R. Salimi
(74) *Attorney, Agent, or Firm*—Chainey P. Singleton; Edwin S. Flores; Chalker Flores, LLP

(57) ABSTRACT

The present invention includes compositions and methods for the identification, characterization and use of a novel antiviral protein that includes a mitochondrial anti-viral signaling protein.

12 Claims, 54 Drawing Sheets

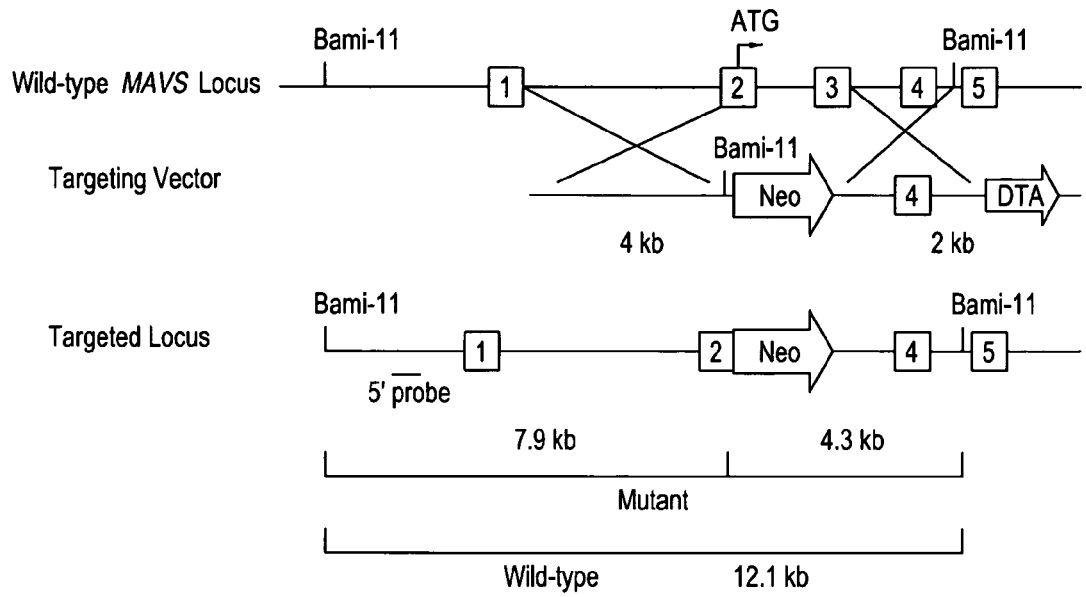
FIG. 14A
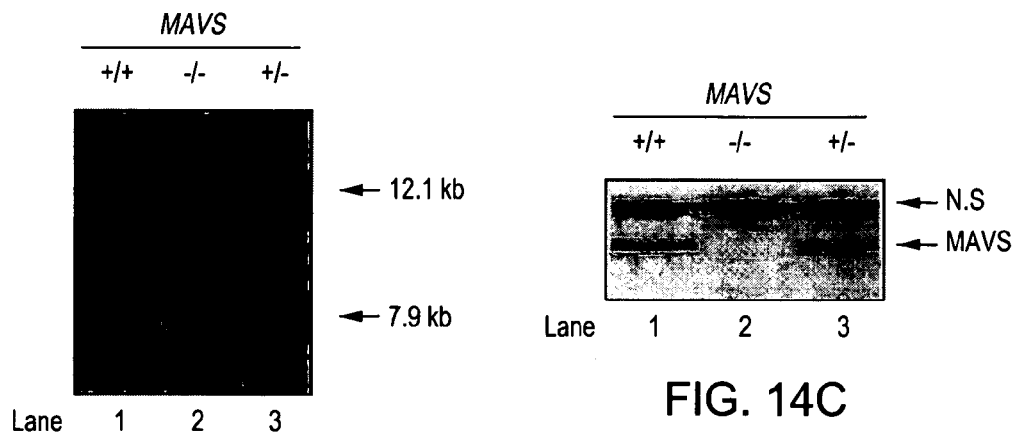
FIG. 14B
FIG. 14C
| Mavs | +/+ | +/- | -/- |
|---|---|---|---|
| Total # | 111 | 223 | 108 |
| % | 25.1 | 50.5 | 24.4 |
FIG. 14D

|  | −10 | +10 |
|---|---|---|
| NS3/4A | CMSADLEVVT | STWVLVGGVL |
| NS4A/4B | YREFDEMEEC | ASHLPYIEQG |
| NS4B/5A | WINEDCSTPC | SGSWLRDVWD |
| NS5A/5B | EEASEDVVCC | SMSYTWTGAL |
|  | 508 | → TM |
| MAVS (human) | RKFQEREVPC | HRPSPGALWL |
| MAVS (chimpanzee) | RKFQEREVPC | HRPSPGALWL |
| MAVS (mouse) | QQPQEEEEHC | ASSMPWAKWL |
| MAVS (rat) | QQSPEEEEPC | SGDSNGPSLL |
| MAVS (chicken) | NNSSHAEVPT | SGDSNGPSLL |
| MAVS (puffer fish) | PAPQDPTKKT | SSHFLTTNTK |

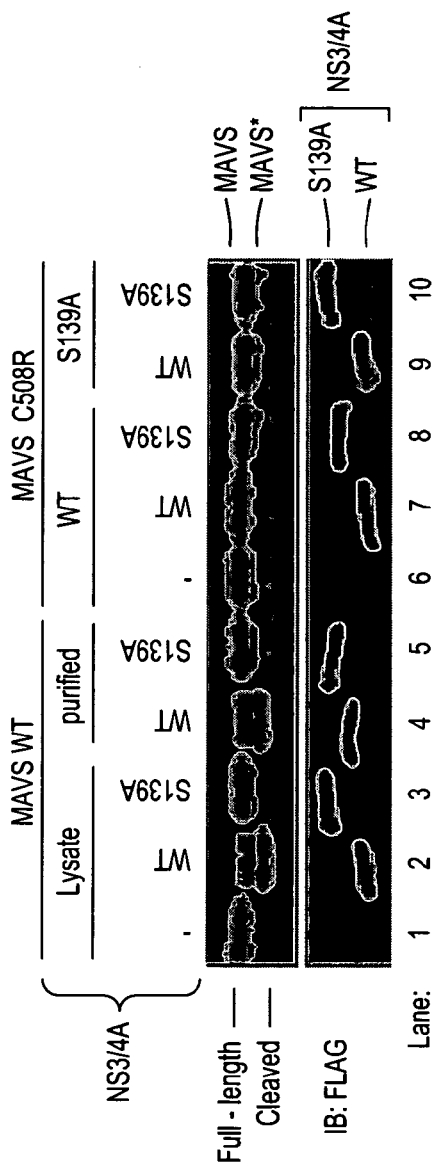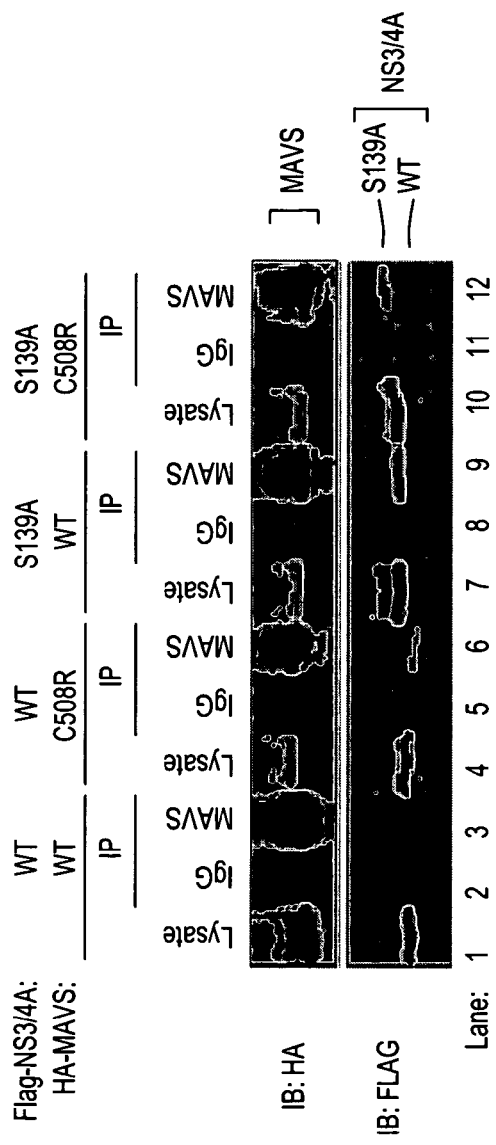
FIG. 23A
FIG. 23B

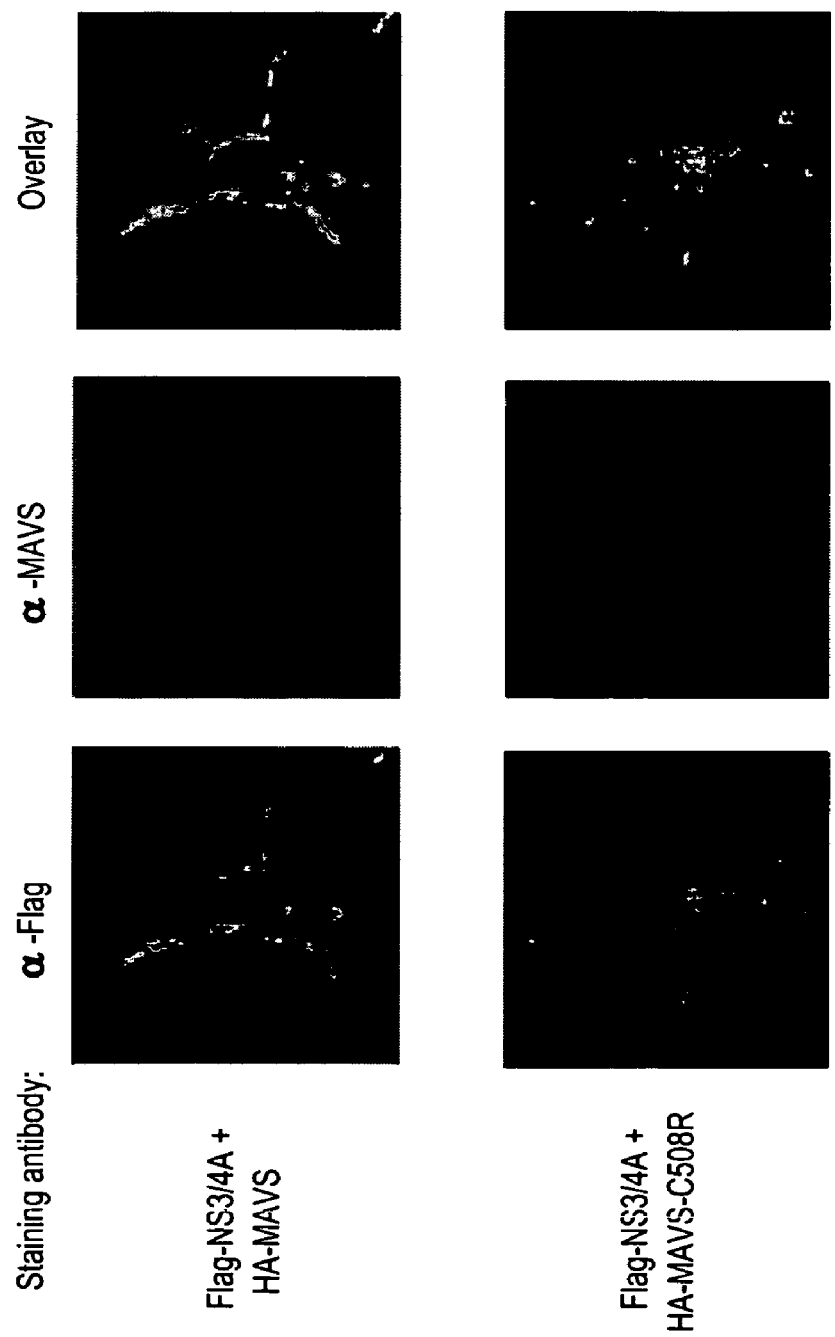

MAVS IN THE PREVENTION AND TREATMENT OF VIRAL DISEASES

STATEMENT OF FEDERALLY FUNDED RESEARCH

This invention was made with U.S. Government support under Contract No. RO1-AI60919 and 1-S10-RR19406 awarded by the NIH. The government has certain rights in this invention.

TECHNICAL FIELD OF THE INVENTION

The present invention relates in general to the field of mediators of immune responses, and more particularly, to a gene that encodes a protein essential for viral immunity.

INCORPORATION-BY-REFERENCE OF MATERIALS FILED ON COMPACT DISC

The present application includes a Sequence Listing filed electronically on Feb. 28, 2007. The Sequence Listing is presented in a single file named UTSW1051.txt. The Sequence Listing was last modified Feb. 18, 2007 at 2:54 PM and includes 9,486 bytes.

BACKGROUND OF THE INVENTION

This application claims priority to Ser. No. 60/711,451 filed Aug. 25, 2005, the entire contents of which are incorporated herein by reference. Without limiting the scope of the invention, its background is described in connection with antiviral agents.

Viral diseases have remained a major global health threat. It would have been a far more devastating epidemic if there were no innate immunity, which is the first line of defense against microbial pathogens. How viruses elicit and evade host innate immune defense is not well understood.

Viral infection of host cells triggers innate and adaptive immune responses that are essential for the survival of the host. A highly effective antiviral immune response is the production of type-I interferons, such as interferon-α (IFN-α) and interferon-β (IFN-β). These interferons activate the JAK-STAT pathway to stimulate the expression of interferon-stimulated genes (ISGs), which collectively inhibit viral replication and assembly (Darnell et al., 1994). The genes encoding interferons are regulated by the assembly of an enhanceosome containing several transcription factors including NF-κB and IRF3, both of which are regulated by subcellular localization (Maniatis et al., 1998). In unstimulated cells, NF-κB is sequestered in the cytoplasm in association with an inhibitor of the IκB family (Baeuerle and Baltimore, 1988). Stimulation of cells with cytokines (e.g., TNFα or IL-1β) or pathogens (e.g., bacteria or viruses) leads to the activation of a large kinase complex consisting of the catalytic subunits IKKα and IKKβ, and the essential regulatory subunit NEMO (also known as IKKγ or IKKAP). The activated IKK complex phosphorylates IκB and targets this inhibitor for degradation by the ubiquitin-proteasome pathway. NF-κB is then liberated to enter the nucleus to turn on a battery of genes essential for immune and inflammatory responses (Silverman and Maniatis, 2001).

Similar to NF-κB, IRF3 is also retained in the cytoplasm of unstimulated cells. After viral or bacterial infection of cells, IRF3 is phosphorylated at multiple serine and threonine residues at the C-terminus (Hiscott et al., 2003; Yoneyama et al., 2002). The phosphorylated IRF3 then homodimerizes and enters the nucleus to activate IFN-β in a highly cooperative manner with NF-κB. The kinases that phosphorylate IRF3 have recently been identified as the IKK-like kinases TBK1 and IKKε (Fitzgerald et al., 2003; Sharma et al., 2003). Genetic studies have shown that TBK1 is important for interferon production by the bacterial cell wall component lipopolysaccharides (LPS) as well as viruses (Hemmi et al., 2004; McWhirter et al., 2004). In some cells, however, the function of TBK1 may be compensated by IKKε or other kinases (Perry et al., 2004; Yoneyama et al., 2004). TBK1 and IKKε can also phosphorylate and activate IRF7 (tenOever et al., 2004), another IRF family member essential for the production of type-I interferons such as interferon-α (Honda et al., 2005).

Both NF-κB and IRFs are tightly regulated by microbial pathogens, including RNA viruses. After entry into host cell and uncoating of an RNA virus, the viral RNA replicates to produce double-stranded RNA intermediates, which are recognized by the host as a pathogen-associated molecular pattern (PAMP). Several proteins that recognize viral RNA have been discovered, including Toll-like receptors TLR3, 7 and 8 (Akira and Takeda, 2004). TLR3 contains an intracellular Toll-Interleukin Receptor (TIR) domain that signals to NF-κB and IRF3 via the adaptor protein TRIF (Akira and Takeda, 2004), whereas the TIR domain of TLR7 and TLR8 binds to another adaptor MyD88, which associates with and activates IRF7 to induce interferon-α (Kawai et al., 2004). In addition, TLRs contain several extracellular Leucine-Rich Repeats (LRR) that presumably recognize microbial ligands. Thus, the topology of these receptors dictates that they can only recognize extracellular dsRNA or single-stranded RNA associated with viral particles that are internalized into the endosomes (Crozat and Beutler, 2004). The receptor that detects intracellular dsRNA generated by the virus is a newly identified protein RIG-I, which has two N-terminal caspase activation and recruitment domains-like (CARD-like) domains, and a C-terminal RNA helicase domain that binds to dsRNA (Sumpter et al., 2005; Yoneyama et al., 2004). Presumably, the binding of viral RNA to RIG-I leads to a conformational change that exposes the CARD-like domain, which then activates downstream signaling. Consistent with this model, overexpression of the N-terminal CARD-like domains of RIG-I is sufficient to activate both NF-κB and IRF3 (Yoneyama et. al., 2004). However, the mechanism by which RIG-I activates NF-κB and IRF3. is currently not understood. A RIG-I-like protein MDA-5 (also known as HELICARD), which also contains two CARD-like domains and an RNA helicase domain, has recently been shown to be involved in dsRNA signaling and apoptosis (Andrejeva et al., 2004; Kang et al., 2002; Kovacsovics et al., 2002). However, MDA-5 does not appear to function redundantly with RIG-I in the antiviral pathway, as an inactivating mutation of RIG-I or the loss of RIG-I expression completely blocks interferon production by several RNA viruses (Kato et al., 2005; Sumpter et al., 2005; Yoneyama et al., 2004).

SUMMARY OF THE INVENTION

The present invention includes the identification and characterization of a novel protein that is essential for NF-κB and IRF3 activation by RNA viruses. This protein, named Mitochondrial Anti-Viral Signaling (MAVS), includes an N-terminal CARD-like domain and a C-terminal transmembrane domain that targets the protein to the mitochondrial membrane. MAVS functions downstream of RIG-I and upstream of IκB and IRF3 phosphorylation. Suppression of MAVS expression blocked interferon production and exacerbated the viral replication and killing of the host cells. Conversely, overexpression of MAVS augmented interferon production and conferred antiviral immunity. Deletion of the CARD-like domain of MAVS abolished its signaling function and converted it into a dominant negative mutant that inhibited interferon induction. Importantly, the mitochondrial targeting transmembrane domain is also essential for MAVS signaling, thus implicating a new role of mitochondria in innate immunity.

Therefore, it was found that the MAVS protein activates the NF-κB and IRF families of transcription factors to induce interferons in viral infected cells to clear viral infection. Unexpectedly, MAVS is a mitochondrial membrane protein and the mitochondrial localization is crucial to MAVS signaling. These results reveal a new role of mitochondria in innate immunity.

In one embodiment, the present invention includes a polynucleotide that encodes a mitochondrial anti-viral signaling (MAVS) protein encoded by the nucleic acid as set forth by SEQ ID NO. 1, which may be, e.g., a DNA, RNA or modified versions thereof. The MAVS protein may be a mouse, rat or other human mitochondrial anti-viral signaling protein. The polynucleotide may be operably linked to a promoter, e.g., a polyoma, Adenovirus 2, Simian Virus 40, β-lactamase, MAVS, lac, tac, trp, Osf, Runt, 3-phosphoglycerate kinase, enolase, alcohol dehydrogenase 2, isocytochrome C, acid phosphatase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and/or a glucokinase promoter. Often, the polynucleotide will be provided as part of a vector, e.g., a plasmid or viral vector. The polynucleotide may be the entire contiguous nucleic acid sequence of SEQ ID NO:1 or portions thereof, e.g., oligonucleotides of 10, 15, 20, 25, 50 or more nucleotides in length, may be single or double stranded, and includes complements and conservative variants thereof.

The present invention also includes an isolated host cell with a vector that expresses a mitochondrial anti-viral signaling protein encoded by the nucleic acid as set forth by SEQ ID NO. 1. The host cell may be a prokaryotic cell or a eukaryotic cell, e.g., a bacterial, fungal or animal host cell. The host cell may even be within a non-human transgenic animal. While some host cells may only carry the gene, the host cell may also express constitutively and/or inductively the mitochondrial anti-viral signaling protein.

Yet another embodiment is a polypeptide having an amino acid sequence that include at least 12 contiguous amino acid residues from SEQ ID NO.:2, the polypeptide having human mitochondrial anti-viral signaling activity. For example, the polypeptide may have the amino acid sequence of SEQ ID NO.:2 and/or conservative mutations thereof. The polypeptide may be used to generate antibodies in an animal or by recombinant methods. As such, the present invention also includes a purified antibody that specifically binds to a polypeptide having an amino acid sequence that includes at least 12 contiguous amino acid residues from SEQ ID NO.:2 that is a mitochondrial anti-viral signaling protein or peptide. The antibody may specifically bind to a polypeptide having the amino acid sequence of SEQ ID NO.:2. The antibody may be linked to a detectable label, e.g., a radioactive label, a fluorogenic label, a nuclear magnetic spin resonance label, biotin and/or an enzyme that generates a colored product upon contact with a chromogenic substrate. Other examples of detectable labels or markers include a gold, a silver or a magnetic particle, alkaline phosphatase, hydrogen peroxidase or glucose oxidase enzyme.

The present invention also includes a method for detecting a mitochondrial anti-viral signaling protein in a sample by obtaining a sample suspected of having an mitochondrial anti-viral signaling protein, contacting the sample with a first antibody that binds to an mitochondrial anti-viral signaling protein under conditions effective to allow the formation of immune complexes and detecting the immune complexes so formed. For example, the antibody may be linked to a radioactive label, a fluorogenic label, a nuclear magnetic spin resonance label, biotin or an enzyme that generates a colored product upon contact with a chromogenic substrate.

The present invention also include an immunodetection kit, in which one or more suitable containers is provided that includes a polypeptide with the amino acid sequence of SEQ ID NO:2, or a first antibody that binds to a polypeptide with the amino acid sequence of SEQ ID NO:2, and at least one immunodetection reagent. Alternatively, the kit may detect nucleic acid sequences in SEQ ID NO.: 1. Immunodetection reagents may include a detectable label that is linked to the polypeptide or the first antibody and/or the immunodetection reagent may be a detectable label that is linked to a second antibody that has binding affinity for the polypeptide or the first antibody.

The present invention also includes a diagnostic method that includes the steps of obtaining a cellular samples from a patient suspected of having a viral expression and determining the level of expression of a mitochondrial anti-viral signaling protein. The diagnostic method may measure an anti-viral activity that may include the overexpression of a mitochondrial anti-viral signaling protein. Using one or more of these methods, a compound may be isolated that enhances or preserves the function of a mitochondrial anti-viral signaling protein isolated by a method that includes the steps of contacting a sample suspected of having a mitochondrial anti-viral signaling protein activator and detecting the downstream activity of the activation of mitochondrial anti-viral signaling protein. Such a compound may be used to treat a viral disease, e.g., a viral disease such as hepatitis C, west nile virus, VSV, influenza or SARS. Examples of virus families that may be treated with the compound include a Picornaviridae, Caliciviridae, Astroviridae, Coronaviridae, Togaviridae, Flaviviridae Paramyxoviridae, Rhabdoviridae, Filoviridae, Orthomyxoviridae, Bunyaviridae, Bornaviridae, Arenaviridae and combinations or mixtures thereof. Specific examples that may be amenable to treatment using the present invention include, e.g., Sindbis virus, rubella, hepatitis C virus, West Nile virus, yellow fever virus, tick-borne encephalitis virus, Japanese encephalitis virus, coxsackivirus, enterovirus, hepatitis A virus, hepatitis C virus, SARS, astrovirus, Dengue fever virus, poliovirus, and Venezuela encephalitis virus, WEE, EEE, Marayo O'nong nong, Ross River, Chikungunya, DV, Rhinovirus, Feline, murine, Norwalk, Bovine, human coronaviridae, RSV, Ebola, respiratory syncytial virus (RSV), Ebola virus, rabies virus, Lassa fever, Argentine hemorrhagic fever virus, La Crosse virus, Rift Valley fever, Hantaan virus, California encephalitis virus, influenza virus A, influenza virus B, measles, mumps, Marburg virus, Bolivian hemorrhagic fever virus, Crimean-Congo virus, HPIV, HMPV, Nipah, Hendra, VSV, LCMV, Junin, Bunyamwera, Uukuniemi, CCHF, HIV-1, HIV-2, HTLV-1, or HTLV-2 and combinations or mixtures thereof. Downstream signals that are detected in the method of the present invention include, e.g., IFN-β secretion, activation of NF-κB and IRF families of transcription factors and/or combinations thereof.

For example, the compound may prevent the destruction, cleavage or inactivation of mitochondrial anti-viral signaling protein, the compound being isolated by a method that includes the steps of contacting a sample suspected of including a mitochondrial anti-viral signaling protein activator, a cell and a virus and detecting the extent of viral infection caused by the virus. The present invention also includes a diagnostic method for detection of the activity, abundance, modification or cleavage of a mitochondrial anti-viral signaling protein for detection, prevention and treatment of viral diseases, the method further including the steps of obtaining a sample suspected of containing an mitochondrial anti-viral signaling protein; contacting the sample with a first antibody that binds to an mitochondrial anti-viral signaling protein, under conditions effective to allow the formation of immune complexes and detecting the immune complexes so formed.

The polynucleotide of the present invention may be used in a transgenic animal that includes a vector that controls the expression mitochondrial anti-viral signaling protein, e.g., overexpresses, wherein the transgenic is used for the development of preventives or therapeutics of viral diseases. The present invention also includes a knockout or knock-in animal with a reduced, depleted or enhanced mitochondrial anti-viral signaling protein and/or constitutive or induceable expression of MAVS or MAVS anti-sense. The present invention also includes various forms of interfering RNAs, as taught herein.

The present invention also includes a high throughput screening method for the isolation of antivirals by contacting a pool of candidates suspected of having a mitochondrial anti-viral signaling protein activator, detecting the downstream activity of the pool of candidates on the activation of mitochondrial anti-viral signaling protein and repeating the steps above with a subgroup of the pool of candidates that activate the mitochondrial anti-viral signaling protein. The assay may be at least in part cell-based, in vitro and/or in vivo.

BRIEF DESCRIPTION OF THE DRAWINGS

For a more complete understanding of the features and advantages of the present invention, reference is now made to the detailed description of the invention along with the accompanying figures and in which:

(FIG. 1A) A schematic diagram of MAVS protein. TM: transmembrane domain. (FIG. 1B) Sequence alignment of the CARD-like domains of MAVS, RIG-I and MDA-5, using the Clustal W program. (FIG. 1C) Sequence alignment of the CARD-like domains of MAVS from different species based on the genome projects. The asterisk (*) indicates the residues that were mutated to alanine in FIG. 6A. (FIG. 1D) Prediction of the MAVS transmembrane domain using the TMpred server. A score of greater than 500 predicts a transmembrane region;

FIG. 2 shows that MAVS is a potent inducer of IFN-β.

FIG. 3 shows that MAVS is required for IFN-β induction by Sendai virus.

FIG. 4 demonstrates that MAVS is a potent antiviral protein.

FIG. 5 shows that MAVS functions downstream of RIG-I and upstream of TBK1.

FIG. 6 shows that the CARD-like domain is essential for MAVS signaling.

FIG. 7 shows that MAVS is a mitochondrial antiviral signaling protein.

FIG. 8 shows that MAVS activates JNK and IRF7.

FIG. 11 shows the localization and mislocalization of MAVS.

FIG. 12 shows the interaction of MAVS with other proteins implicated in the antiviral signaling pathway.

Figure 1:
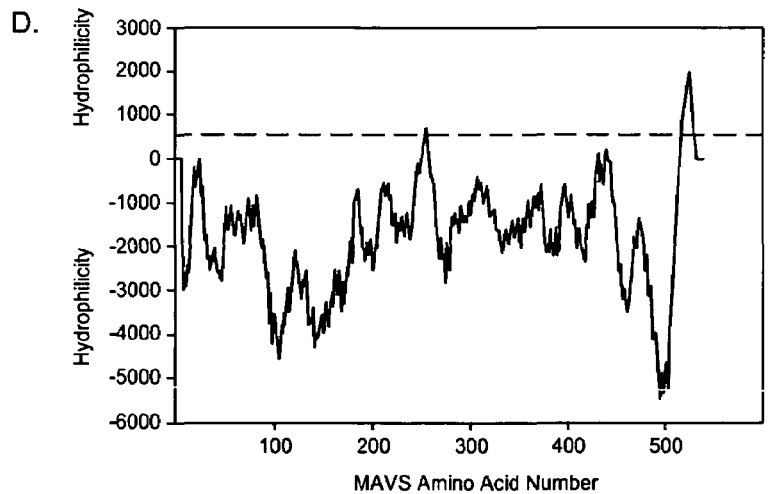
FIG. 1 summarizes the domain and sequence analyses of MAVS.

5×10⁷ pfu) via tail vein injection, and the survival of the mice was monitored for 5 weeks. The mice that survived the viral infections at 2 weeks remained alive after 5 weeks. The gene dosage of Mavs is critical for the survival of mice following viral infection. (D) Wild type (n=4), Mavs+/− (n=4) and Mavs−/− (n=6) mice were infected with VSV-GFP at 1×10⁸ pfu via tail vein injection. The survival of the mice was monitored for 12 days. Littermates of 16-20 weeks old mice were used in this study. (E) Similar to (A), except that 2×10⁸ pfU VSV-GFP was used to infect littermates of 4-7 weeks old mice. Wild-type: n=7; Mavs+/−: n=5; Mavs−/−: n=5.

FIG. 20. MAVS is required for interferon induction by poly(I:C) in vivo. Wild type (n=5), Mavs$^{+/-}$ (n=5) and Mavs$^{-/-}$ (n=6) mice were injected intravenously with 200 μg of poly(I:C), and then sera were collected at indicated times for ELISA to measure the concentrations of IFN-α (A), IFN-β (B) and IL-6 (C). Littermates of 10-12 weeks old mice were used for this study. The error bars indicate standard errors.

FIG. 21. NS3/4A blocks interferon induction by MAVS. (A) HEK293 cells were transfected with the IFN-β luciferase reporter construct together with the expression vector for the wild type or S139A mutant of NS3/4A. On the next day, cells were transfected with expression vectors encoding MAVS, TBK1, or RIG-I(N), or infected with Sendai virus. 24 hours later, the luciferase activity was measured and normalized for transfection efficiency. The error bar represents standard deviation from the mean value of duplicated studies. (B) Similar to (A), except that NF-κB luciferase reporter was used in lieu of IFN-β-Luc. (C) Similar to (A), except that cells were transfected with the UAS-luciferase reporter together with the Gal4-IRF3 expression vector. (D) HEK293 cells were transfected with the wild type or S139A mutant of NS3/4A together with the expression vectors for MAVS (lanes 5-7) or TBK1 (lanes 8-10). In lanes 24, cells were infected with Sendai virus for 24 hours. Cell lysates were resolved by electrophoresis under native (upper) or denaturing condition (middle) and then immunoblotted with an antibody against IRF3. The expression of NS3/4A and TBK1 was also analyzed by immunoblotting with a Flag antibody (bottom panel).

FIG. 22. NS3/4A cleaves MAVS at Cys-508. (A) HEK293 (lanes 1-6) or Huh7 (lanes 7-12) cells were transfected with expression vectors for the wild type (lanes 3, 4, 9 & 10) or S139A mutant (lanes 5, 6, 11 & 12) of NS3/4A or vector (lanes 1, 2, 7 & 8). Cell lysates were separated into membrane pellet (P) or cytosolic supernatant (S), and then immunoblotted with an antibody against MAVS or Flag. The cleavage product of MAVS was indicated as MAVS*. (B) HEK293 cells were transfected with the expression vectors for NS3/4A together with a MAVS mutant containing only the CARD and TM domains (mini-MAVS). The activation of IFN-β by the CARD-TM fragment of MAVS in the presence of wild type or S139A mutant of NS3/4A was determined by measuring the expression of the IFN-β-Luc reporter (middle panel). Cell lysates were analyzed by immunoblotting with the Flag antibody that detects both NS3/4A and MAVS proteins (bottom panel). (C) Alignment of the junction sequences of nonstructural (NS) proteins of HCV, and the putative cleavage site at the C-terminus of MAVS from different species. (D) HEK293 cells were transfected with expression vectors encoding the wild type or C508R mutant of MAVS together with those encoding the wild type or S139A mutant of NS3/4A. Cell lysates were separated by differential centrifugation into the membrane pellet (P) and cytosolic supernatant (S), which were then resolved by 7% (upper panel and lower panel) or 4-20% (middle panel) SDS-PAGE, following by immunoblotting with the indicated antibody that detects the N-terminus (Flag; upper panel) or C-terminus (HA; middle panel) of MAVS, or NS3/4A (Myc; lower panel). (E) HEK293 cells were transfected with MAVS and NS3/4A expression vectors as in (D), except that IFN-β-Luc was also co-transfected to measure the induction of IFN-β by luciferase assay.

FIG. 23. NS3/4A binds to and colocalizes with MAVS in the mitochondria, and it cleaves MAVS in vitro. (A) Flag-tagged wild type or S139A mutant of NS3/4A was expressed in HEK293 cells, and then purified using Flag-Sepharose. The purified NS3/4A proteins (lanes 4, 5, 9 & 10) or lysates containing NS3/4A (lanes 1-3, 6-8) were incubated with ³⁵S-labeled MAVS or C508R mutant of MAVS, which was synthesized by in vitro translation and purified using Flag-Sepharose. After incubation at 30° C. for 2 hours, proteins were separated by SDS-PAGE and analyzed by PhosphorImaging (top) or immunoblotting (bottom). The cleavage product of MAVS was indicated as MAVS*. (B) HEK293 cells were transfected with expression vectors for Flag-NS3/4A and HA-MAVS as indicated. Cell lysates were immunoprecipitated with the MAVS antibody (lanes 3, 6, 9 & 12) or control IgG (lanes 2, 5, 8 & 11). The precipitated proteins were analyzed by immunoblotting with an antibody against HA (top) or Flag (bottom). (C) Expression vectors for Flag-NS3/4A and HA-MAVS or C508R mutant were transfected into HeLa cells, and the localization of these proteins were stained by the indicated antibodies and visualized by confocal microscopy.

FIG. 24. MAVS is cleaved at Cys-508 in an HCV replicon cell line. (A) Cell lysates from Huh7 (lanes 1 & 2) or Replicon cells (K2040; lanes 3 & 4) were separated by centrifugation into the membrane pellet (P) and cytosolic supernatant (S), which were then analyzed by immunoblotting with an antibody against MAVS or NS3. The cleavage products of MAVS were indicated as MAVS*. (B & C) Expression vectors for MAVS, C508 mutant of MAVS, or RIG-I(N) was co-transfected with the IFN-β luciferase reporter into Huh7 (B) or Replicon (C) cell lines. 24 hours after transfection, cells were infected with Sendai virus or mock infected for another 24 hours before harvesting for luciferase assay.

Figure 25A:
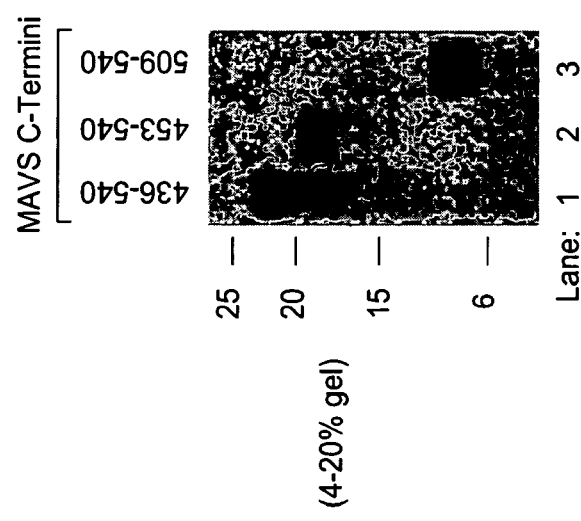

FIG. 25. MAVS is cleaved by NS3/4A at Cys-508, but not other C-terminal cysteines. (A) Expression vectors encoding the C-terminal fragments of MAVS as indicated were translated in vitro in the presence of ³⁵S-methione. Each fragment also contains an N-terminal methionine and a C-terminal HA tag, so that each can serve as a size marker for the C-terminal fragment of MAVS if the cleavage were to occur at Cys435, Cys452, or Cys-508 (see FIG. 22D). (B) HEK293 cells were transfected with expression constructs for NS3/4A and MAVS containing mutations at Cys residues as indicated. Cell lysates were separated into membrane pellet (P) and cytosolic supernatant (S) and then analyzed by immunoblotting.

FIG. 26. (A) MAVS is cleaved directly by NS3/4A in vitro. The His$_6$-NS3/4A protease was expressed in E. coli, and then purified using nickel affinity column. The purified protease was incubated with ³⁵S-labelled MAVS or its C508R mutant at 30° C. for 2 hours, and then analyzed by SDS-PAGE followed by PhosphorImaging. (B) NS3/4A is localized within or proximal to the mitochondrial membrane. The expression vector encoding Flag-NS3/4A was transfected into HeLa cells, and the expressed protein stained with the Flag antibody and then visualized by confocal microscopy. Cells were also stained with Mito Tracker (top) or an antibody against calnexin (bottom) to label the mitochondria or endoplasmic reticulum, respectively.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defamed herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventors recognized that viral infection triggers host innate immune responses through activation of the transcription factors NF-κB and IRF3, which coordinately regulate the expression of type-I interferons such as interferon-β (IFN-β). The present invention includes compositions and methods for the identification, characterization and use, of a novel protein termed Mitochondrial Anti-Viral Signaling (MAVS) that mediates the activation of NF-κB and IRF3 in response to viral infection. Silencing of MAVS expression through RNA interference abolishes the activation of NF-κB and IRF3 by viruses, thereby permitting viral replication. Conversely, overexpression of MAVS induces the expression of IFN-β through activation of NF-κB and IRF3, thus boosting antiviral immunity. Epistasis studies show that MAVS is required for the phosphorylation of IRF3 and IκB, and functions downstream of RIG-I, an intracellular receptor for viral RNA. MAVS contains an N-terminal CARD-like domain and a C-terminal transmembrane domain, both of which are essential for MAVS signaling. The transmembrane domain targets MAVS to the mitochondria, implicating a new role of mitochondria in innate immunity.

As used herein, a "Mitochondrial Anti-Viral Signaling-specific nucleic acid" is used to describe either DNA, RNA, single-stranded or double-stranded and any chemical modifications thereof or protein nucleic acids. Modifications include, but are not limited to, those that provide other chemical groups that incorporate additional charge, polarizability, hydrogen bonding, electrostatic interaction, and fluxionality to the individual nucleic acid bases or to the nucleic acid as a whole.

A sample is any mixture of macromolecules obtained from cells, a cellular supernatant, a tissue (e.g., blood) or a secretion, e.g., from a patient. When obtained from a patient, a sample includes, but is not limited to, blood, plasma, urine, semen, saliva, lymph fluid, meningeal fluid, amniotic fluid, glandular fluid, and cerebrospinal fluid. This also includes experimentally separated fractions of all of the preceding. Sample also includes solutions or mixtures containing homogenized solid material, such as feces, cells, tissues, and biopsy samples. Samples herein include one or more that are obtained at any point in time, including diagnosis, prognosis, and periodic monitoring.

The terms "a sequence essentially as set forth in SEQ ID NO. (1)", "a sequence similar to", "nucleotide sequence" and similar terms, with respect to nucleotides, refers to sequences that substantially correspond to any portion of the sequence identified herein as SEQ ID NO.: 1. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of a Mitochondrial Anti-Viral Signaling activity, such as increased activation of NF-κB and IRF3 in response to viral infection and/or regulation of interferon-β (IFN-β) secretion. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

The inhibition of hybridization of the completely complementary sequence to the target sequence may also be examined using a hybridization assay involving a solid support (e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective. Low stringency conditions are generally conditions equivalent to binding or hybridization at 42 degrees Centigrade in a solution consisting of 5×SSPE (43.8 g/l NaCl, 6.9 g/l NaH$_2$PO$_4$—H$_2$O and 1.85 g/l EDTA, pH 7.4), 0.1% SDS, 5× Denhardt's reagent (50× Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5× SSPE, 0.1% SDS at 42 degrees Centigrade when a probe of about 500 nucleotides in length is employed. The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

An oligonucleotide sequence that is "substantially homologous" to the Mitochondrial Anti-Viral Signaling of SEQ ID NO: 1" is defined herein as an oligonucleotide sequence that exhibits greater than or equal to 75% identity to the sequence of SEQ ID NO: 1 when sequences having a length of 100 bp or larger are compared.

The term "gene" is used to refer to a functional Mitochondrial Anti-Viral Signaling protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer at least a portion of a Mitochondrial Anti-Viral Signaling DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome The term "host cell" refers to cells that have been engineered to contain nucleic acid segments or altered segments, whether archeal, prokaryotic, or eukaryotic. Thus, engineered, or recombinant cells, are distinguishable from naturally occurring cells that do not contain recombinantly introduced genes through the hand of man.

The term "agonist" refers to a molecule that enhances either the strength or the time of an effect of Mitochondrial Anti-Viral Signaling and encompasses small molecules, proteins, nucleic acids, carbohydrates, lipids, or other compounds. The term "antagonist" refers to a molecule that decreases either the strength or the time of an effect of Mitochondrial Anti-Viral Signaling and encompasses small molecules, proteins, nucleic, acids, carbohydrates, lipids, or other compounds.

The term "altered", or "alterations" or "modified" with reference to nucleic acid or polypeptide sequences is meant to include changes such as insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences for the Mitochondrial Anti-Viral Signaling protein, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

As used herein, term "antibody" is used to describe polyclonal and/or monoclonal antibody preparations, as well as preparations including hybrid antibodies, altered antibodies, F(ab')$_2$ fragments, F(ab) fragments, Fv fragments, single domain antibodies, chimeric antibodies, humanized antibodies, and functional fragments thereof which exhibit immunological binding properties against the Mitochondrial Anti-Viral Signaling protein.

As used herein, the term "monoclonal antibody" is used to refer to an antibody composition having a homogeneous antibody population. The term is not limited to a species or source of the antibody, nor is it intended to be limited by the manner in which it is made, e.g., from an animal source or by recombinant methods. The monoclonal antibody encompasses whole immunoglobulins as well as fragments such as Fab, F(ab')$_2$, Fv, and other fragments that exhibit immunological binding properties of the parent monoclonal antibody molecule.

Methods of making polyclonal and monoclonal antibodies are well known in the art and are described hereinbelow. Polyclonal antibodies are generated by immunizing a suitable animal, such as a mouse, rat, rabbit, sheep or goat, with the Mitochondrial Anti-Viral Signaling protein, or fragments thereof. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Rabbits, sheep and goats may be used for the preparation of polyclonal sera when large volumes of sera are desired. These animals are choices because of the availability of labeled anti-rabbit, anti-sheep and anti-goat antibodies. Immunization is generally performed by mixing or emulsifying the MAVS protein with an adjuvant, e.g., Freund's complete adjuvant ("FCA"), and injecting the mixture or emulsion parenterally (e.g., subcutaneously or intramuscularly). A booster immunization if provided in 2-6 weeks internals. Polyclonal antisera is then obtained from the immunized animal.

Monoclonal antibodies are generally prepared using the method of Kohler and Milstein, Nature (1975) 256:495-497, or a modification thereof, relevant portions incorporated herein by reference. Typically, a mouse, hamster or rat is immunized and immune organs are harvested upon the detection of anti-MAVS antisera. Resulting B-cells are fused with myeloma cells to form hybridomas, and are. cultured in a selective medium (e.g., hypoxanthine, aminopterin, thymidine medium, "HAT"). The surviving hybridoma cells are plated by limiting dilution, and each well is assayed for the production of antibodies that bind specifically to MAVS. The selected monoclonal antibody-secreting hybridomas are then cultured either in vitro (e.g., in tissue culture bottles or hollow fiber reactors), or in vivo (e.g., as ascites in mice).

The term Fv is defined to be a covalently or noncovalently-associated heavy and light chain heterodimer without constant domains. Fab's are heterodimers of the variable domain and the first constant domain of an antibody heavy chain, plus the variable domain arid constant domain of an antibody light chain, plus at least one additional amino acid residue at the carboxy terminus of the heavy chain $C_H1$ domain including one or more cysteine residues. F(ab')$_2$ antibody fragments are pairs of Fab' antibody fragments linked by one or more covalent bond(s). The Fab' heavy chain may include a hinge region.

The term Fv-SH or Fab'-SH is defmed herein as an Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

As used herein, the term "humanized antibody: is used to describe an immunoglobulin amino acid sequence variant or fragment thereof that is capable of binding to a predetermined antigen and that includes an FR region having substantially the amino acid sequence of a human immunoglobulin and a CDR having substantially the amino acid sequence of a non-human immunoglobulin or a sequence engineered to bind to the MAVS antigen.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Highly regulated inducible promoters that suppress Fab' polypeptide synthesis at levels below growth-inhibitory amounts while the cell culture is growing and maturing, for example, during the log phase may be used.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. Enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean a nucleic acid sequence that is foreign to the cell, or homologous to the cell but in a position within the host cell nucleic acid in which the element is ordinarily not found.

As used herein, the expressions "cell" and "cell culture" are used interchangeably end all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (Nucleic Acids Res. 1981. 9:6103-6114), and Goeddel et al. (Nucleic Acids Res. 1980. 8:4057).

"Preparation" of DNA from cells is used to describe the isolation of a plasmid DNA from a culture of the host cells. Methods used commonly for DNA preparation are the large and small-scale plasmid preparations described in sections 1.25-1.33 of Sambrook et al., (Molecular Cloning: A Laboratory Manual New York: Cold Spring Harbor Laboratory Press, 1989). DNA preparations are purified by methods well known in the art (see section 1.40 of Sambrook et al., supra).

As used herein, the term "aptamer" refers to an oligonucleotide that has been designed or discovered that is able to specifically bind a target sequence.

As used herein the terms "protein", "polypeptide" or "peptide" refer to compounds comprising amino acids joined via peptide bonds and are used interchangeably.

As used herein, the term "endogenous" refers to a substance the source of which is from within a cell. Endogenous substances are produced by the metabolic activity of a cell. Endogenous substances, however, may nevertheless be produced as a result of manipulation of cellular metabolism to, for example, make the cell express the gene encoding the substance.

As used herein, the term "exogenous" refers to a substance the source of which is external to a cell. An exogenous substance may nevertheless be internalized by a cell by any one of a variety of metabolic or induced means known to those skilled in the art.

The term "gene" is used to refer to a polynucleotide or nucleic acid that encodes at least a portion of a MAVS protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. The term "sequences" as used herein is used to refer to nucleotides or amino acids, whether natural or articifical, e.g., modified nucleic acids or amino acids. When describing "transcribed nucleic acids" those sequence regions located adjacent to the coding region on both the 5', and 3', ends such that the deoxyribonucleotide sequence corresponds to the length of the full-length mRNA for the protein as included. The term "gene" encompasses both cDNA and genomic forms of a gene. A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA I wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed, excised or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

The term "gene of interest" as used here refers to a gene, the finction and/or expression of which is desired to be investigated, or the expression of which is desired to be regulated, by the present invention. In the present disclosure, the MAVS gene of the MAVS protein is an example of a gene of interest and is described herein to illustrate the invention. The present invention may be useful in regard to any gene of any organism, whether of a prokaryotic or eukaryotic organism.

The term "hybridize" as used herein, refers to any process by which a strand of nucleic acid binds with a complementary strand through base pairing. Hybridization and the strength of hybridization (i.e., the strength of the association between the nucleic acid strands) is impacted by such factors as the degree of complementary between the nucleic acids, stringency of the conditions involved, the melting temperature of the formed hybrid, and the G:C (or U:C for RNA) ratio within the nucleic acids.

The terms "complementary" or "complementarity" as used herein, refer to the natural binding of polynucleotides under permissive salt and temperature conditions by base-pairing. For example, for the sequence "A-G-T" binds to the complementary sequence "T-C-A". Complementarity between two single-stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology," as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

When used in reference to a single-stranded nucleic acid sequence, the term "substantially homologous" refers to any probe which can hybridize (i.e., it is the complement of) the single-stranded nucleic acid sequence under conditions of low stringency as described. As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

As used herein, the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less. Low stringency conditions comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA [Fraction V; Sigma]) and 100 µg/ml denatured salmon sperm DNA) followed by washing in a solution comprising 5× SSPE, 01% SDS at 42° C. when a probe of about 500 nucleotides in length is employed. High stringency conditions comprise conditions equivalent to binding or hybridization at 65° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA [Fraction V; Sigma]) and 100 µg/ml denatured salmon sperm DNA) followed by washing in a solution comprising 5× SSPE, 01% SDS at 65° C. when a probe of about 500 nucleotides in length is employed. Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

The term "antisense," as used herein, refers to nucleotide sequences that are complementary to a the MAVS DNA or RNA sequence. The term "antisense strand" is used in reference to a nucleic acid strand that is complementary to tile "sense" strand. Antisense molecules may be produced by any method, including synthesis by ligating the gene(s) of interest in a reverse orientation to a viral promoter which permits the synthesis of a complementary strand. Once introduced into a cell, the transcribed strand combines with natural sequences produced by the cell to form duplexes. These duplexes then block either the further transcription or translation. In this manner, mutant phenotypes may also be generated. The designation "negative" is sometimes used in reference to the antisense strand, and "positive" is sometimes used in reference to the sense strand. The term also is used in reference to RNA sequences that are complementary to a specific RNA sequence (e.g., mRNA). Included within this definition are antisense RNA ("asRNA") molecules involved in genetic regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural MRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation. (−) (i.e., "negative") is sometimes used in reference to the antisense strand with the designation (+) sometimes used in reference to the sense (i.e., "positive") strand.

As used herein, the term "transformation," is used to define a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

The term "transfection" as used herein refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells which transiently express the inserted DNA or RNA for limited periods of time. Thus, the term "transient transfection" or "transiently transfected" refers to the introduction of foreign DNA into a cell where the foreign DNA fails to integrate into the genome of the transfecied cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "selectable marker" refers to the use of a gene that encodes an enzymatic activity and which confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. A review of the use of selectable markers in mammalian cell lines is provided in Sambrook, J., et al., MOLECULAR CLONING: A LABORATORY MANUAL, 2nd ed., Cold Spring Harbor Laboratory Press, New York (1989) pp. 16.9-16.15, relevant portions incorporated herein by reference.

As used herein, the term "reporter gene" refers to a gene that is expressed in a cell upon satisfaction of one or more contingencies and which, upon expression, confers a detectable phenotype to the cell to indicate that the contingencies for expression have been satisfied. For example, the gene for Luciferase, β-galactosides, green fluorescent protein and the like confers a luminescent phenotype to a cell when the gene is expressed inside the cell. In the present invention, the gene for Luciferase may be used as a reporter gene such that the gene is only expressed upon the splicing out of an intron in response to an effector. Those cells in which the effector activates splicing of the intron will express Luciferase and will glow.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted oat from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, relevant portions incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as DCTP or DATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

The word "specific" as commonly used in the art has two somewhat different meanings. The practice is followed herein. "Specific" refers generally to the origin of a nucleic acid sequence or to the pattern with which it will hybridize to a genome, e.g., as part of a staining reagent. For example, isolation and cloning of DNA from a specified chromosome results in a "chromosome-specific library". Shared sequences are not chromosome-specific to the chromosome from which they were derived in their hybridization properties since they will bind to more than the chromosome of origin. A sequence is "locus specific" if it binds only to the desired portion of a genome. Such sequences include single-copy sequences contained in the target or repetitive sequences, in which the copies are contained predominantly in the selected sequence.

As used herein, the term "transgene" is used to describe MAVS genetic material that may be artificially inserted into a mammalian genome, e.g., a mammalian cell of a living animal. The term "transgenic animal is used herein to describe a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A transgene may be an expression construct (e.g., for the production of a "knock-in" transgenic animal) or a heterologous nucleic acid that upon insertion within or adjacent a target gene results in a decrease in target gene expression (e.g., for production of a "knock-out" transgenic animal). As used herein, a "knock-out" is used to describe the alteration of a gene sequence that decreases of function of the target gene, preferably such that target gene expression is undetectable or insignificant. Transgenic knock-out stem cells, cells and animals include a heterozygous knock-out of a target gene, or a homozygous knock-out of a target gene. As used herein, a "Knock-out" may include, e.g., conditional knock-outs, wherein alteration of the target gene can be activated by exposure of the animal to a substance that promotes target gene alteration, introduction of an enzyme that promotes recombination at the target gene site (e.g., Cre in the Cre-lox system), or other method for directing the target gene alteration.

As used herein, "knock-in" refers to of a target gene is used herein to define an alteration in a host cell genome that results in altered expression (e.g., increased or decreased expression) of a target gene, e.g., by introduction of an additional copy of the target gene, or by operatively inserting a regulatory sequence that provides for enhanced expression of an endogenous copy of the target gene. "Knock-in" transgenics include heterozygous knock-in of the target gene or a homozygous knock-in of a target gene and include conditional knock-ins.

As used herein, the term "stem cell" refers to pluripotent stem cells, e.g., embryonic stem cells, and to such pluripotent cells in the very early stages of embryonic development, including but not limited to cells in the blastocyst stage of development.

EXAMPLE 1

Identification and Sequence Analysis of MAVS. To understand the signaling pathways required for the activation of NF-κB and IRF3 by viruses, proteins were identified that include CARD-like domains similar to those of RIG-I and its homologue MDA-5. A BLAST search with the first CARD-like domain of MDA-5 identified an uncharacterized protein KIAA1271, which contains a single CARD-like domain at the N-terminus. Interestingly, this protein was also identified as a putative NF-κB activator in a large-scale screening for proteins that can activate an NF-κB reporter when they are overexpressed (Matsuda et al., 2003). However, there was no further characterization of this protein concerning its domain structure, activity or biological function. The present invention includes the characterization of the function for this protein, and found that in addition to the N-terminal CARD-like domain, which is conserved from pufferfish to human (FIG. 1A-C), KIAA1271 also contains a proline-rich region in the middle and a hydrophobic transmembrane domain at the C-terminus (FIG. 1D). The transmembrane domain was predicted using two different programs: TMpred (http://www.ch.embnet.org/software/TMPRED_form.html; FIG. 1D), and Kyte-Doolittle hydropathy plot (data not shown). As will be shown later (FIG. 7), this transmembrane domain targets KIAA1271 to the mitochondria. This protein was designated as Mitochondrial Anti-Viral Signaling (MAVS) protein. The nucleic acid sequence for MAVS is as follows:

```
                                                      (SEQ ID NO.: 1)
   1 atgccgtttg ctgaagacaa gacctataag tatatctgcc gcaatttcag caattttgc
  61 aatgtggatg ttgtagagat tctgccttac ctgccctgcc tcacagcaag agaccaggat
 121 cgactgcggg ccacctgcac actctcaggg aaccgggaca ccctctggca tctcttcaat
 181 acccttcagc ggcggcccgg ctgggtggag tacttcattg cggcactgag gggctgtgag
 241 ctagttgatc tcgcggacga agtggcctct gtctacgaga gctaccagcc tcggacctcg
 301 gaccgtcccc cagacccact ggagccaccg tcacttcctg ctgagaggcc agggccccc
 361 acacctgctg cggcccacag catcccctac aacagctgca gagagaagga gccaagttac
 421 cccatgcctg tccaggagac ccaggcgcca gagtccccag gagagaattc agagcaagcc
 481 ctgcagacgc tcagccccag agccatccca aggaatccag atggtggccc cctggagtcc
 541 tcctctgacc tggcagccct cagccctctg acctccagcg ggcatcagga gaaggacaca
 601 gaactgggca gtacccacac agcaggtgcg acctccagcc tcacaccatc ccgtgggcct
 661 gtgtctccat ctgtctcctt ccagcccctg gcccgttcca cccccagggc aagccgcttg
 721 cctggaccca cagggtcagt tgtatctact ggcacctcct tctcctcctc atcccctggc
 781 ttggcctctg caggggctgc agagggtaaa cagggtgcag agagtgacca ggccgagcct
 841 atcatctgct ccagtggggc agaggcacct gccaactctc tgccctccaa agtgcctacc
 901 accttgatgc ctgtgaacac agtggccctg aaagtgcctg ccaacccagc atctgtcagc
 961 acagtgccct ccaagttgcc aactagctca aagcccctg gtgcagtgcc ttctaatgcg
1021 ctcaccaatc cagcaccatc caaattgccc atcaactcaa cccgtgctgg catggtgcca
1081 tccaaagtgc ctactagcat ggtgctcacc aaggtgtctg ccagcacagt ccccactgac
1141 gggagcagca gaaatgagga gaccccagca gctccaacac ccgccggcgc cactggaggc
1201 agctcagcct ggctagacag cagctttgag aatagggggcc ttgggtcgga gctgagtaag
1261 cctggcgtgc tggcatccca ggtagacagc ccgttctcgg gctgcttcga ggatcttgcc
1321 atcagtgcca gcacctcctt gggcatgggg ccctgccatg gccagagga gaatgagtat
1381 aagtccgagg gcaccttttgg gatccacgtg gctgagaacc ccagcatcca gctcctggag
1441 ggcaaccctg gccacctgc ggacccggat ggcggcccca ggccacaagc cgaccggaag
1501 ttccaggaga gggaggtgcc atgccacagg ccctcacctg ggctctgtg gctccaggtg
1561 gctgtgacag gggtgctggt agtcacactc ctggtggtgc tgtaccggcg gcgtctgcac
1621 tag;
and
```

Encodes a protein having the amino acid sequence:

(SEQ ID NO.: 2)
MPFAEDKTYKYICRNFSNFCNVDVVEILPYLPCLTARDQDRLRATCTLSG

NRDTLWHLFNTLQRRPGWVEYFIAALRGCELVDLADEVASVYESYQPRTS

DRPPDPLEPPSLPAERPGPPTPAAAHSIPYNSCREKEPSYPMPVQETQAP

ESPGENSEQALQTLSPRAIPRNPDGGPLESSSDLAALSPLTSSGHQEKDT

ELGSTHTAGATSSLTPSRGPVSPSVSFQPLARSTPRASRLPGPTGSVVST

GTSFSSSSPGLASAGAAEGKQGAESDQAEPIICSSGAEAPANSLPSKVPT

TLMPVNTVALKVPANPASVSTVPSKLPTSSKPPGAVPSNALTNPAPSKLP

INSTRAGMVPSKVPTSMVLTKVSASTVPTDGSSRNEETPAAPTPAGATGG

SSAWLDSSFENRGLGSELSKPGVLASQVDSPFSGCFEDLAISASTSLGMG

PCHGPEENEYKSEGTFGIHVAENPSIQLLEGNPGPPADPDGGPRPQADRK

FQEREVPCHRPSPGALWLQVAVTGVLVVTLLVVLYRRRLH.

Protein sequence, see, Nagase, T., et al., Prediction of the coding sequences of unidentified human genes. XV. The complete sequences of 100 new cDNA clones from brain which code for large proteins in vitro, DNA Res. 6 (5), 337-345 (1999); and Homo sapiens KIAA1271 protein, mRNA (cDNA clone MGC:50830 IMAGE:5751684), complete cds. Strausberg, R. L., Generation and initial analysis of more than 15,000 full-length human and mouse cDNA sequences, Proc. Natl. Acad. Sci. U.S.A. 99 (26), 16899-16903 (2002). The GenBank accession number for the human MAVS is DQ 174270 and for the mouse MAVS is DQ 174271.

Figure 2A:
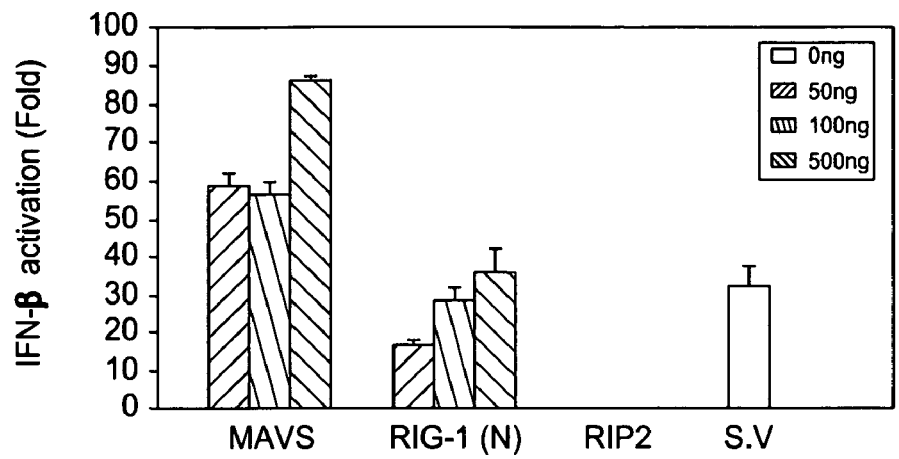
(FIG. 2A) Increasing amounts of expression vectors for MAVS, RIG-I(N), and RIP2 were transfected into HEK293 cells together with an IFNβ-luciferase reporter as well as pCMV-LacZ as an internal control. 36 hours after transfection, the luciferase activity was measured and normalized based on β-galactosidase activity. Each data point was obtained from duplicate studies. S.V: cells transfected with IFNβ-Luc were infected with Sendai virus for 20 hours.
Figure 2B:
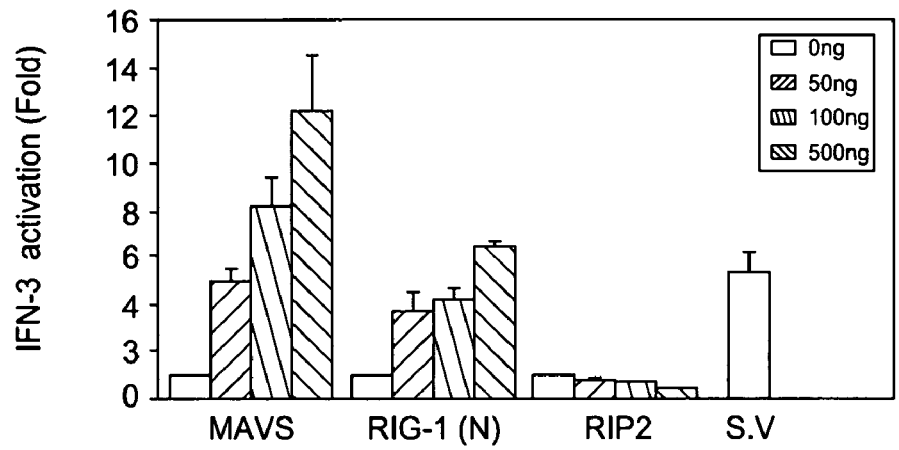
(FIG. 2B) The studies were carried out as in (FIG. 2A), except that Gal4-Luc and Gal4-IRF3 plasmids were co-transfected together in lieu of IFNβ-Luc.
Figure 2C:
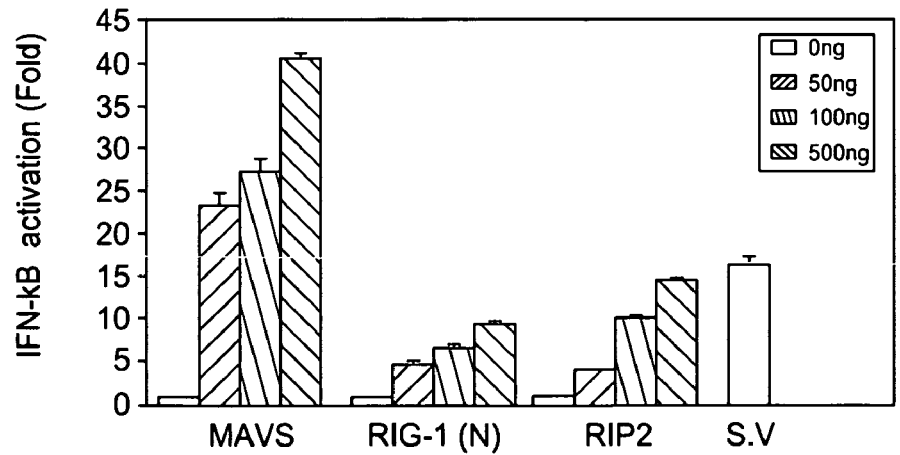
(FIG. 2C) Similar to (FIG. 2A), except that p-κB₃-tk-Luc was transfected in lieu of INFβ-Luc.
Figure 2D:
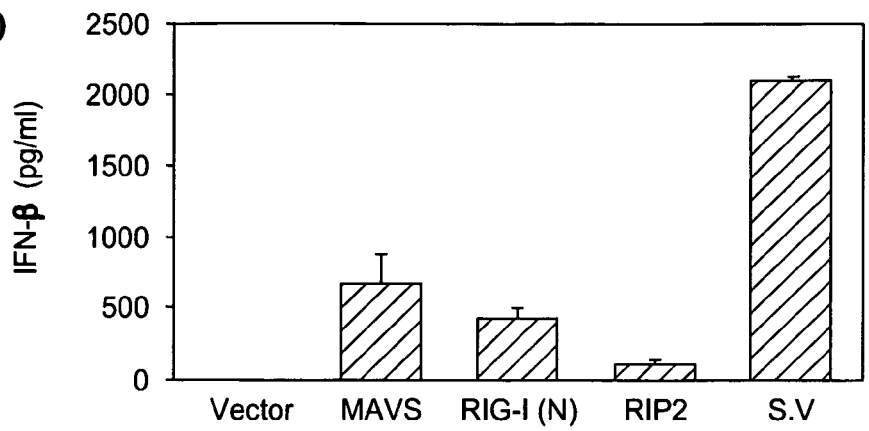
(FIG. 2D) HEK293 cells were transfected with the expression vectors for MAVS (500 ng), RIG-I(N; 200 ng), RIP2 (500 ng), the vector pcDNA3 (500 ng) or infected with Sendai virus (S.V, 50 HA units/ml). 36 hours after transfection or 20 hours after viral infection, the culture supernatant was collected to measure IFN-β production by ELISA.
Figure 2E:
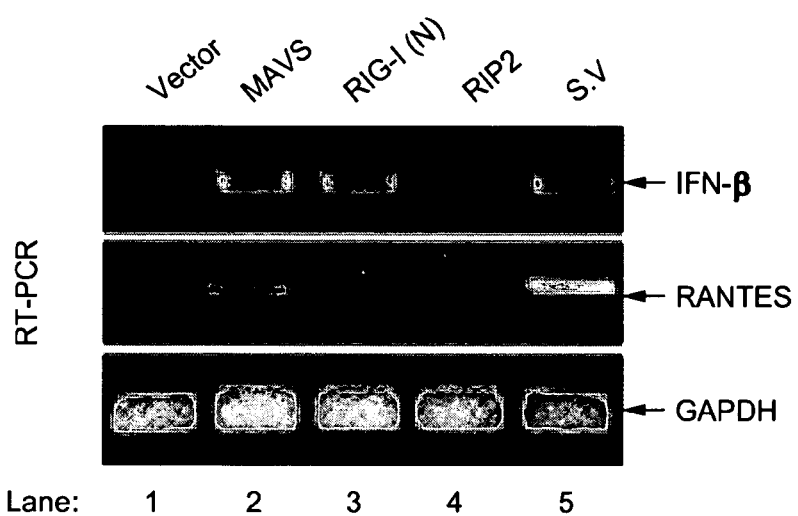
(FIG. 2E) An aliquot of the cell pellet from (FIG. 2D) was lysed to isolate RNA for RT-PCR using primers specific for IFN-β, the chemokine RANTES and GAPDH (as a control).
Figure 2F:
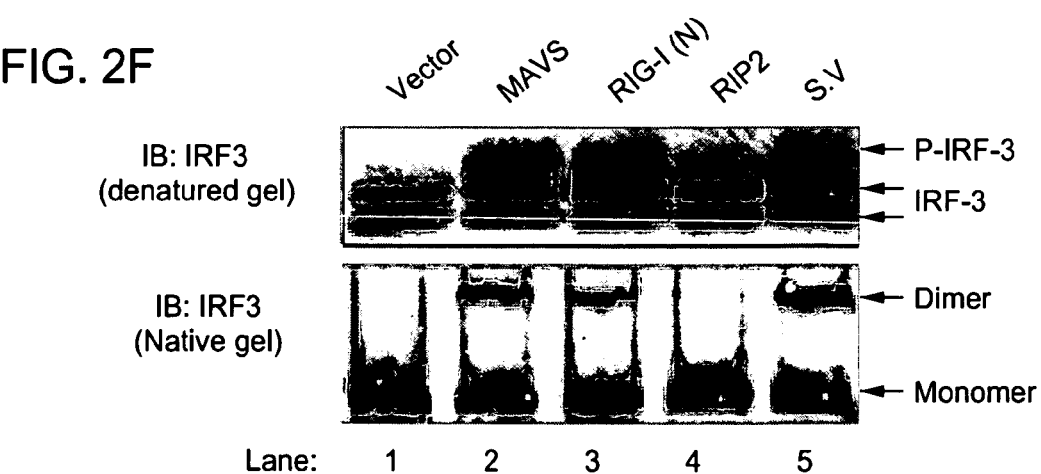
(FIG. 2F) After transfection or viral infection as described in (FIG. 2D), HEK293 cells were lysed to prepare protein extracts, which were then resolved by SDS-PAGE (upper panel) or native gel electrophoresis (lower panel). Phosphorylation or dimerization of IRF3 was detected by immunoblotting (IB) with an IRF3 antibody.
Figure 8A:
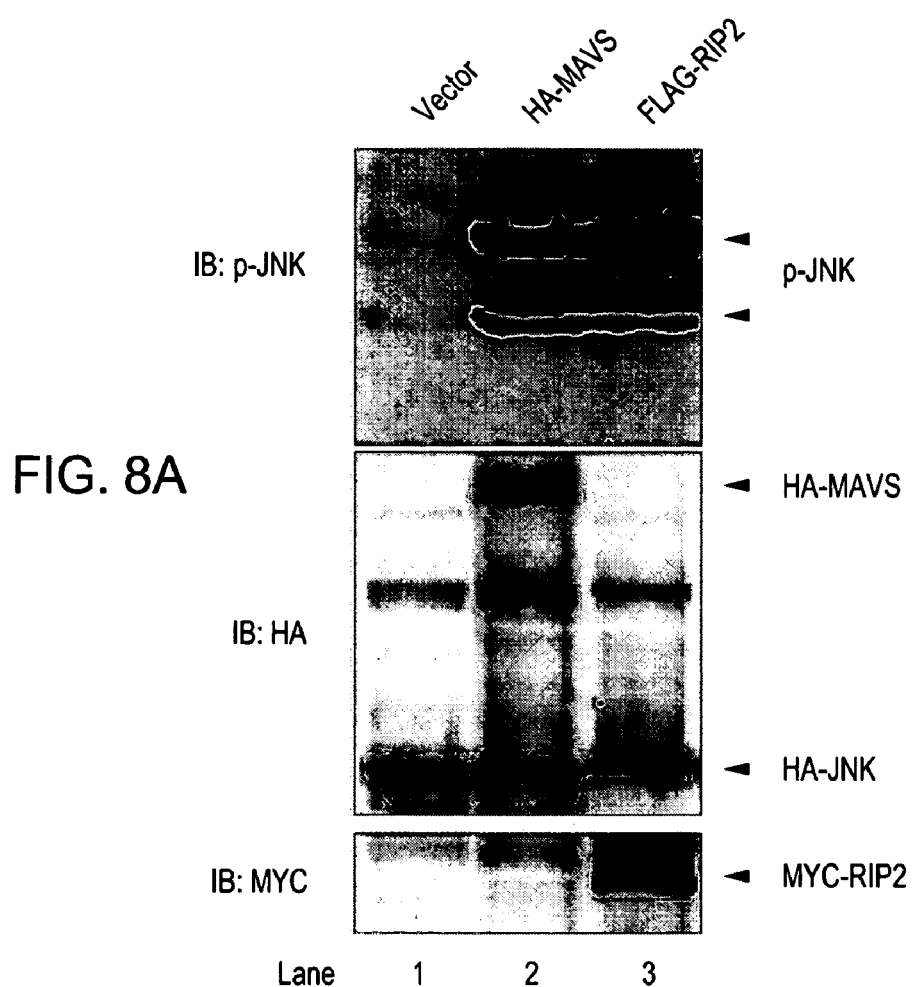
(FIG. 8A) HEK293 cells were transfected with expression vectors encoding HA-JNK together with HA-MAVS, MYC-RIP2 (as a control) or empty vector. 24 hours after transfection, cell lysates were immunoblotted with antibodies against phospho-JNK (p-JNK), HA or MYC.
Figure 8B:
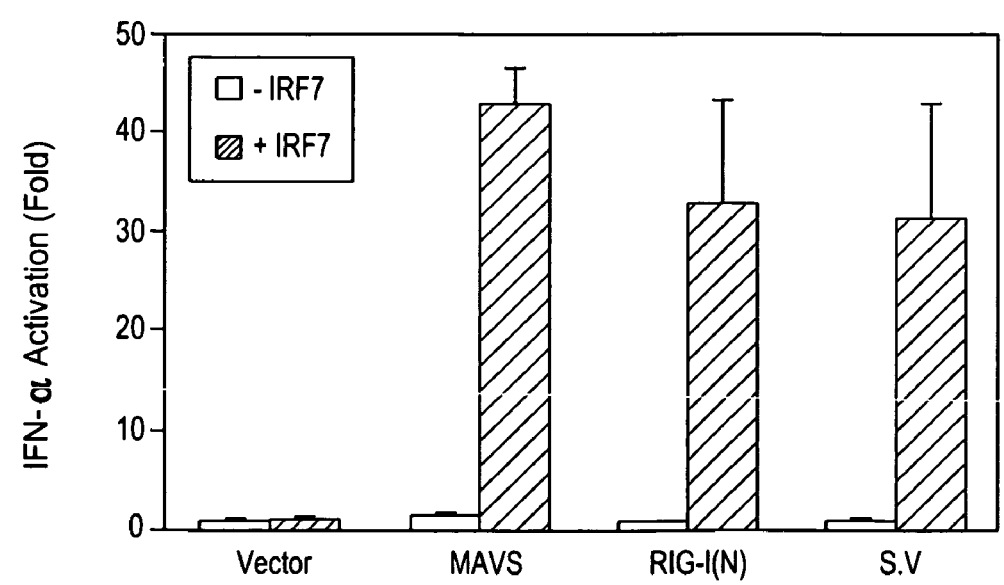
(FIG. 8B) HEK293 cells were transfected with IFNα4-Luc together with expression vectors for IRF7, MAVS or RIG-I(N) as indicated. For Sendai virus infection, 50 HA units of the virus were used to infect cells 24 hours after transfection of the IFNα4-Luc and IRF7 plasmids. Luciferase activity was measured and normalized for transfection efficiency as described herein.

MAVS Activates NF-κB, IRF3 and IRF7 to Induce interferons. Although overexpression of many proteins can activate NF-κB, a much smaller number of proteins can activate both NF-κB and IRF3, which are required for the induction of interferons. Whether MAVS could activate a luciferase reporter that is under the control of the interferon-β (IFN-β) promoter was tested. This promoter contains enhancer elements that bind to several transcription factors including NF-κB, IRF3 and ATF2. The coordinate activation of all of these transcription factors is required for the formation of an enhanceosome that activates IFN-β. Significantly, overexpression of MAVS in HEK293 cells potently activates the IFN-β promoter in a dose-dependent manner (FIG. 2A). In control studies, infection of the same cells with the Sendai virus (SV), an RNA virus of the paramyxoviridae family, leads to the activation of IFN-β. Similarly, overexpression of the tandem N-terminal CARD-like domains of RIG-I [designated as RIG-I(N)] also induces IFN-β. In contrast, overexpression of another CARD domain protein RIP2 (Inohara et al., 1998), which is known to activate NF-κB but not IRF3 in response to intracellular bacterial infection, failed to induce IFN-β. Consistent with the ability of MAVS to induce the assembly of the IFN-β enhanceosome, MAVS activated both IRF3 (FIG. 2B) and NF-κB (FIG. 2C). In the former case, the activation of IRF3 was measured by the phosphorylation and dimerization of a chimeric protein consisting of IRF3 fused to the DNA binding domain of Gal4, which drives the expression of the luciferase reporter gene. In the latter case, NF-κB activation was measured using a luciferase reporter whose expression was driven by three copies of an NF-κB enhancer. Also examined was whether MAVS activates JNK, which is known to phosphorylate and activate ATF2. Similar to RIP2, overexpression of MAVS led to the activation of JNK, as measured by immunoblotting with an antibody specific for phosphorylated JNK (FIG. 8A). Overexpression of MAVS also induced the production of endogenous IFN-β, as determined by ELISA of culture supernatants (FIG. 2D). RT-PCR studies showed that MAVS induced IFN-β and the chemokine RANTES, but not the housekeeping gene GAPDH, at the RNA level (FIG. 2E). Immunoblotting studies showed that MAVS activated IRF3 by inducing the phosphorylation (FIG. 2F, upper panel) and dimerization of IRF3 (FIG. 2F, lower panel). To determine if MAVS also activates IRF7, a master regulator of interferon-α (IFN-α), MAVS was co-transfected, IRF7 and an IFN-α luciferase reporter into HEK293 cells, which do not express endogenous IRF7. Similar to Sendai virus infection, overexpression of MAVS or RIG-I(N) potently induced IFN-α promoter activity (FIG. 8B). Collectively, these results show that MAVS is a potent activator of IRF3, IRF7 and NF-κB, and that its overexpression is sufficient to mimic viral infection to induce cytokines including IFN-α, IFN-β and RANTES.

Figure 3A:
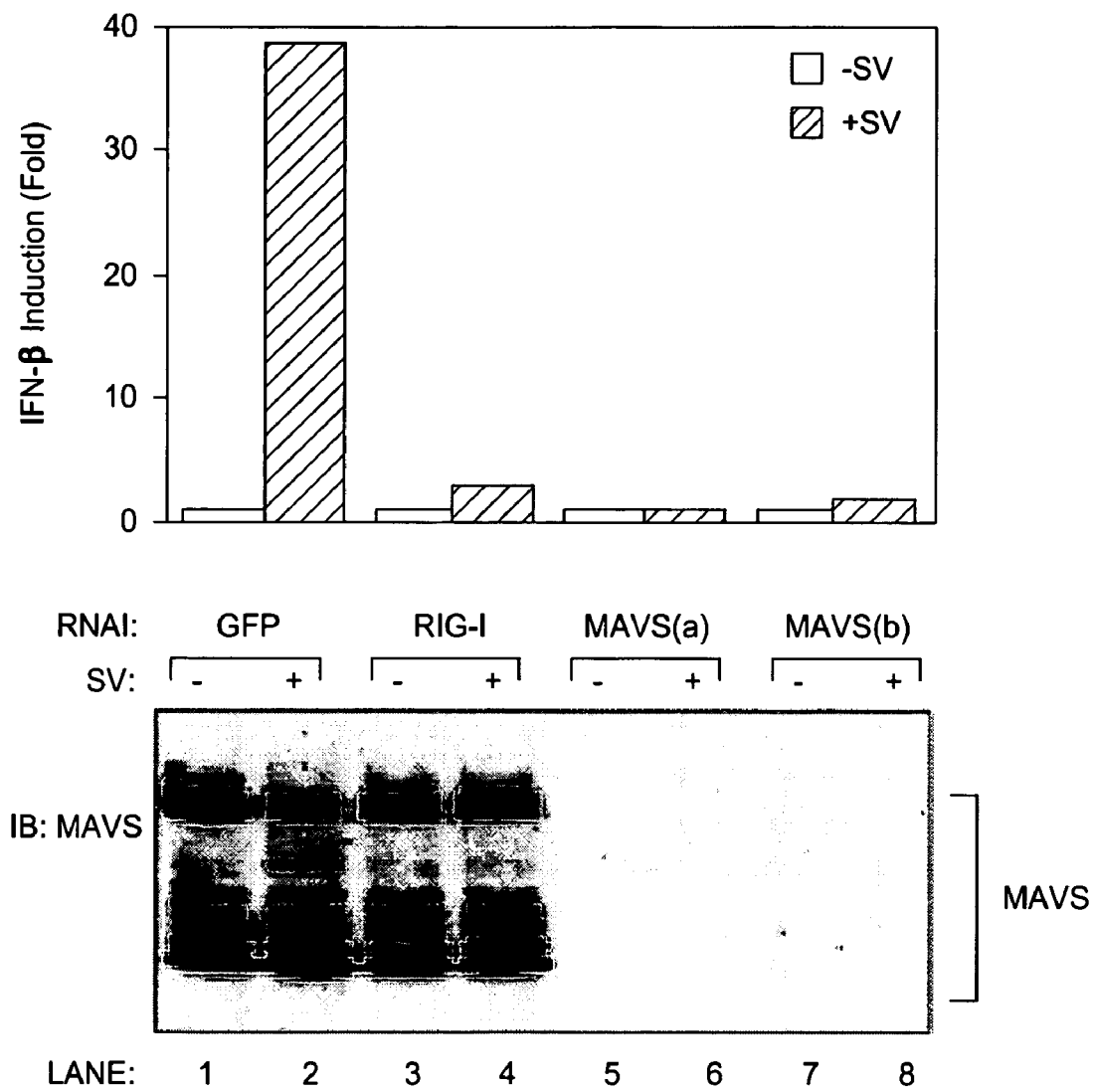
(FIG. 3A) siRNA oligos targeting GFP (control), RIG-I, and two different regions of MAVS (a and b) were transfected into HEK293 cells to silence the expression of endogenous proteins. The efficiency of MAVS RNAi was confirmed by immunoblotting with a MAVS-specific antibody (bottom panel). To measure IFNβ induction, the IFNβ-Luc reporter plasmid was transfected into the RNAi cells, which were then infected with Sendai virus for 20 hours followed by luciferase assays (upper panel).
Figure 9:
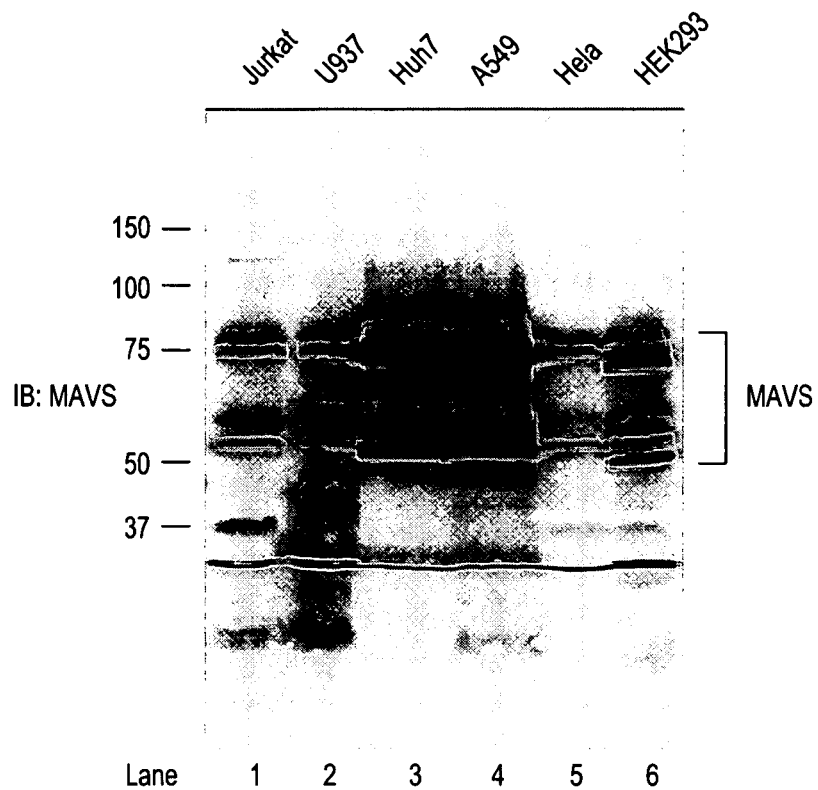
FIG. 9 shows that MAVS is expressed in human cells expected to encounter viruses. Whole cell lysates (20 µg) from the indicated cell lines were immunoblotted with the affinity-purified MAVS antibody. The identity of the immunoreactive bands in HEK293 cells were verified as MAVS based on RNAi studies (FIG. 3A, above). Jurkat: T lymphocyte; U937: monocyte; Huh7: hepatocyte; A549: lung epithelial cell; HeLa: cervical epithelial cell; HEK293: embryonic kidney cell.

MAVS is Required for IKK and IRF3 Activation and IFN-β Induction by Sendai Virus. To determine if MAVS is required for IFN-β induction by viruses, RNAi was used to silence the expression of endogenous MAVS, which was detected with an affinity-purified MAVS antibody against a fragment of MAVS containing amino acids 131-291. This antibody detected multiple bands in whole cell lysates derived from HEK293 cells as well as those transfected with the control GFP siRNA oligos (FIG. 3A, lower panel). These bands disappeared in cells transfected with two different pairs of siRNA oligos targeting distinct regions of MAVS, indicating that the bands detected by the antibody were indeed MAVS proteins. It is not clear why MAVS protein exists as multiple bands on SDS-PAGE, but it is unlikely that they represent different spliced variants, as the same expression pattern was observed when cells were transfected with MAVS cDNA (data not shown). The pattern of these bands did not change when cell extracts were treated with phosphatases or glycosidase (data not shown), suggesting that they are not the phosphorylated or glycosylated forms of MAVS. MAVS modification by ubiquitin or ubiquitin-like proteins such as ISG-15 was not observed. The lower bands may represent the degradation or processing products of MAVS, whereas the upper band is the full-length MAVS protein. The MAVS protein bands were detected by immunoblotting in multiple human cell lines (FIG. 9), including Jurkat (T cell), U937 (monocyte), Huh7 (hepatocyte), A549 (lung epithelial cell) and HeLa (cervical epithelial cell). Thus, MAVS is expressed in many different cell types, especially those that constitute the first line of defense against viruses, such as liver and lung cells.

Figure 3B:
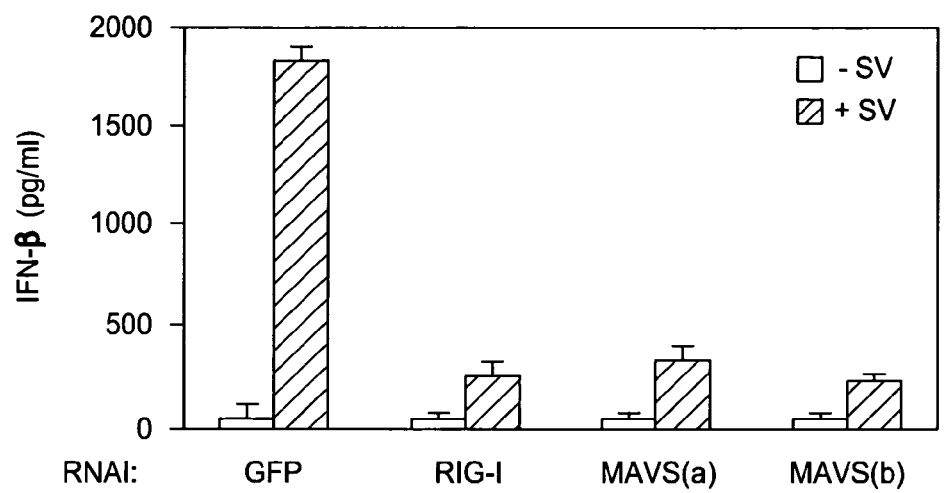
FIG. 3(B) The siRNA transfection into HEK293 cells and viral infection were carried out as in (FIG. 3A), and the supernatant was collected for measurement of IFN-β by ELISA.
Figure 3C:
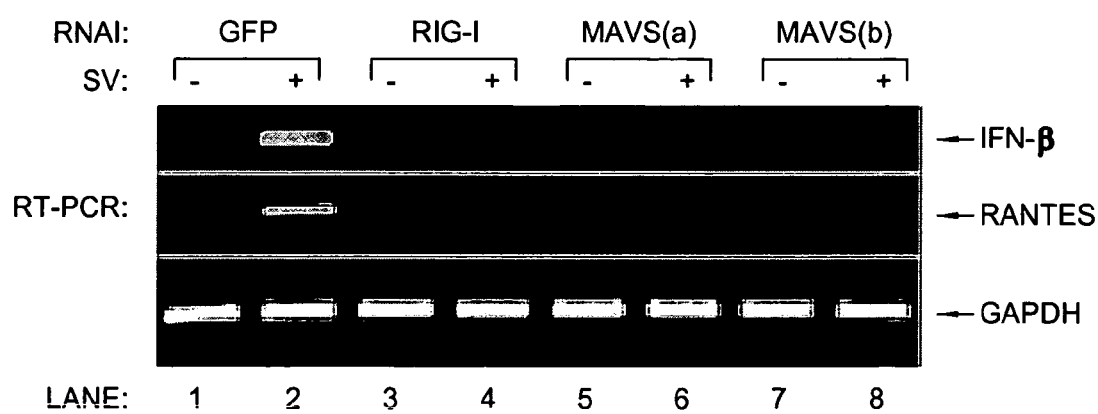
(FIG. 3C) Similar to (FIG. 3B), except that cells were lysed to isolate RNA for RT-PCR.
Figure 3D:
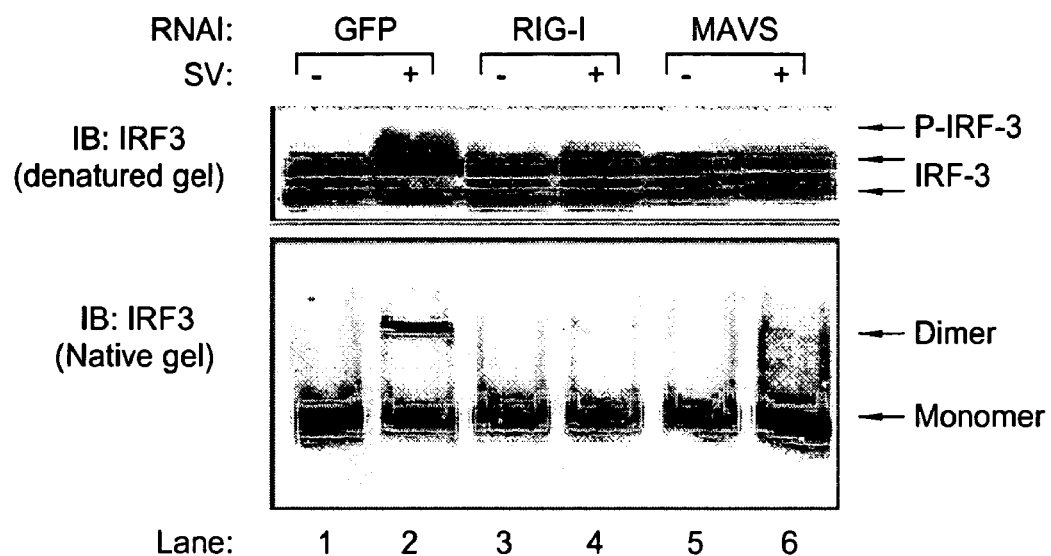
(FIG. 3D) Similar to (FIG. 3B), except that protein extracts were prepared from the cells and analyzed for IRF3 phosphorylation by SDS-PAGE (upper panel) or dimerization by native gel electrophoresis (lower panel).
Figure 3F:
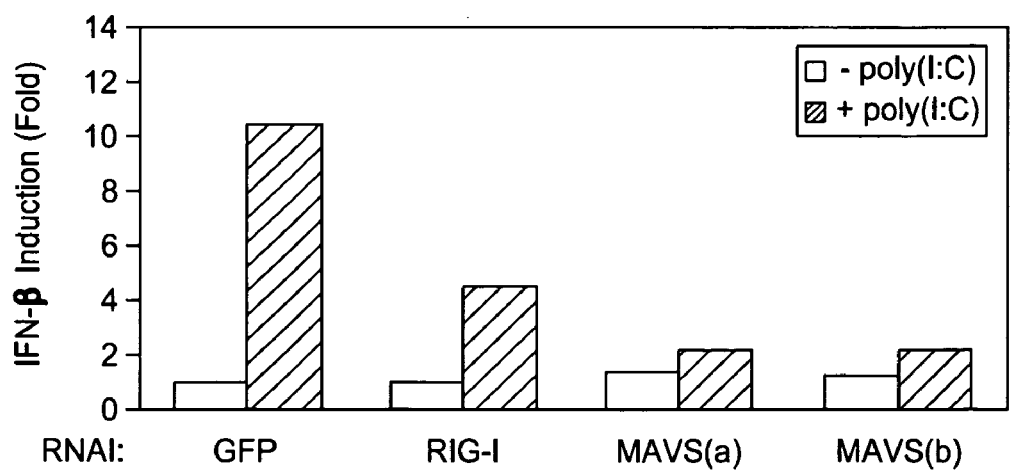
(FIG. 3F) MAVS is required for IFN-β induction by double-stranded RNA. HEK293-RIGI cells were transfected with siRNA oligos targeting GFP, RIG-I or MAVS as described in (FIG. 3A). Subsequently, cells were transfected with 0.5 μg of poly (I:C) or pcDNA3 (as control) together with the IFNβ-Luc and pCMV-LacZ plasmids. Luciferase assays were performed 48 hours after transfection.
Figure 3E:
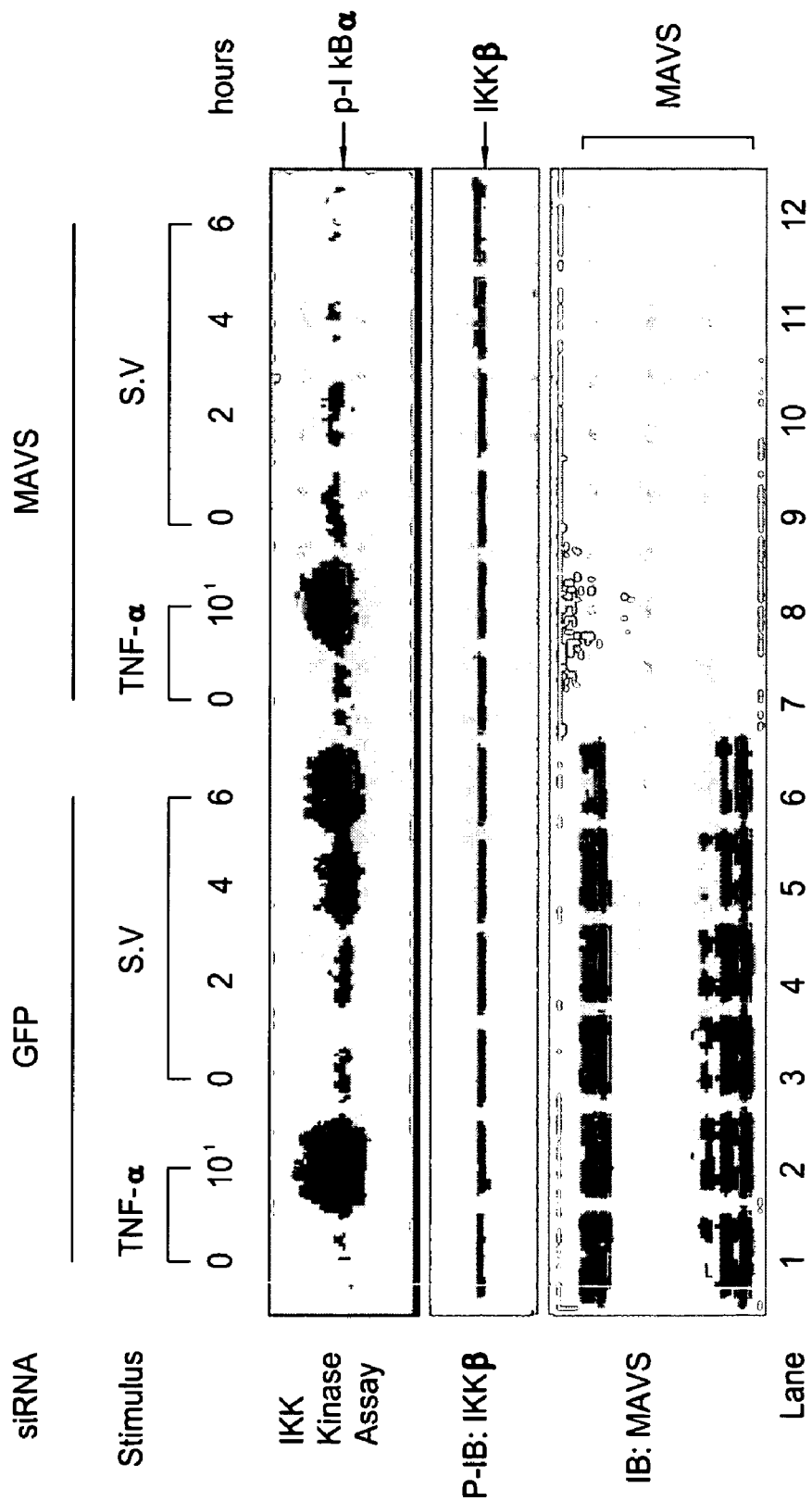
(FIG. 3E) MAVS is required for IKK activation by Sendai virus. HEK293 cells expressing the full-length RIG-I, which facilitates the activation of IKK and IRF3 by Sendai virus, were transfected with siRNA oligos for GFP or MAVS. These cells were then stimulated with TNFα (10 ng/ml) or infected with Sendai virus (50 HA units/ml) for the indicated time before cell lysates were prepared. An aliquot of the cell lysates (20 μg) was immunoblotted with a MAVS antibody (lower panel). 500 μg of the cell lysates were immunoprecipitated with an antibody against NEMO to isolate the IKK complex, whose activity was measured using GST-IκBα and γ-$^{32}$P-ATP as substrates (upper panel). An aliquot of the IKK immunoprecipitate was immunoblotted with an IKKβ antibody (middle panel).

Strikingly, both pairs of MAVS siRNA oligos abolished IFN-β induction by Sendai virus (FIG. 3A, upper panel). Since the sequences of these two pairs of RNA oligos are very different, it is exceedingly unlikely that they silence a common "off-target" gene responsible for IFN-β induction. Further supporting this conclusion, it was found that a MAVS expression vector containing a silent mutation that renders MAVS resistant to RNAi was able to rescue IFN-β induction in the MAVS RNAi cells (data not shown). As controls, RNAi of RIG-I, but not GFP, also blocked viral induction of INF-β (FIG. 3A). Similarly, RNAi of MAVS or RIG-I blocked the production of endogenous IFN-β protein by Sendai virus, as measured by ELISA (FIG. 3B). RT-PCR analyses showed that viral induction of IFN-β and RANTES RNA was abolished in the absence of MAVS or RIG-I (FIG. 3C). Furthermore, RNAi of MAVS or RIG-I prevented the phosphorylation (FIG. 3D, upper panel) and dimerization (FIG. 3D, lower panel) of IRF3 induced by Sendai virus, indicating that both MAVS and RIG-I are required for IRF3 phosphorylation. To determine if MAVS is also required for IKK activation by the virus, an IKK kinase assay was used (FIG. 3E). Since the activation of IKK by Sendai virus is much slower and weaker as compared to TNFα stimulation, HEK293 cell were transfected with an expression construct encoding the full-length RIG-I protein, which potentiated the activation of IKK such that IKK activity was detectable within 4 hours of viral infection (FIG. 3E, lanes 3-6). Importantly, RNAi of MAVS blocked IKK activation by Sendai virus, but not TNFα. To determine if MAVS is required for interferon-β induction by double-stranded RNA (dsRNA), poly (I:C) was transfected into a HEK293 cell line stably expressing the full-length RIG-I protein. The transfected poly (I:C) is known to mimic viral dsRNA to bind to RIG-I and stimulate interferon production. As shown in FIG. 3F, knockdown of MAVS expression with two different pairs of siRNA oligos blocked IFN-β induction by poly (I:C), suggesting that MAVS may be required for immune defense against all RNA viruses that generate dsRNA in their life cycle. Taken together, these results demonstrate that MAVS is essential for viral activation of IKK and IRF3.

Figure 4A:
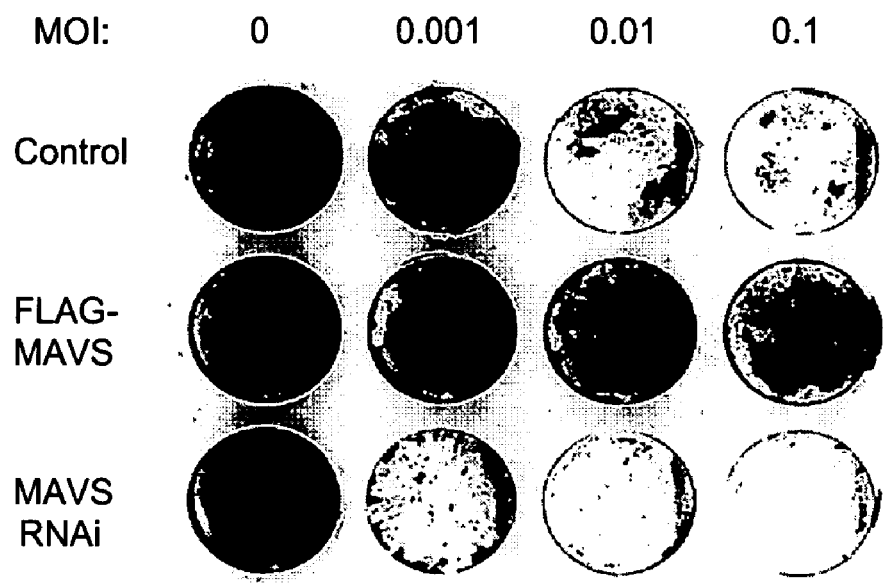
(FIG. 4A) HEK293 cells were transfected with pcDNA3-FLAG-MAVS (0.5 μg) or siRNA oligos (20 nM) targeting MAVS. 48 hours after transfection, cells were infected with VSV at the indicated MOI for 24 hours. After fixing, cells that were not killed by the virus were stained with Amido Black.
Figure 4B:
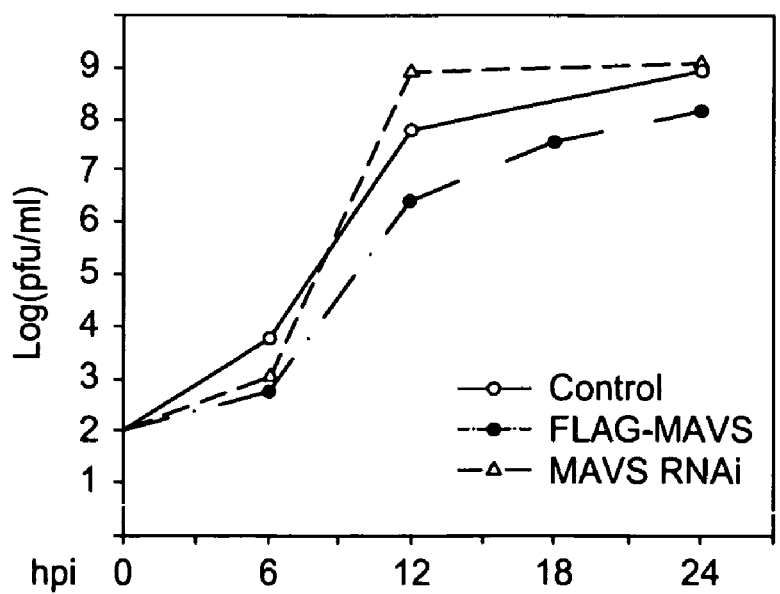
(FIG. 4B) The culture supernatant from cells infected with VSV at the MOI of 0.01 were collected at the indicated time points, and the viral titer was determined by plaque assay.

MAVS is a Potent Antiviral Protein. Since MAVS is both necessary and sufficient for the induction of type-I interferons, whether this protein could mediate immune defense against the vesicular stomatitis virus (VSV), an RNA virus of the rhabdoviridae family was examined. Infection of HEK293 cells by VSV led to nearly complete killing of the cells within 24 hours at a multiplicity of infection (MOI) of 0.01 (FIG. 4A). Transfection of these cells with an expression vector encoding FLAG-MAVS prevented cell killing by VSV even at an MOI of 0.1. Conversely, silencing of the endogenous MAVS expression by RNAi greatly sensitized cell killing by VSV at a much lower MOI (0.001). Measurement of the viral titer showed that overexpression of FLAG-MAVS decreased the viral titer by more than 20 fold as compared to control cells [from $5.5 \times 10^7$ to $2.6 \times 10^6$ plaque forming unit (pfu) at 12 hours after infection]. Conversely, RNAi of MAVS led to an increase of viral titer by 20 fold as compared to control cells (from $5.5 \times 10^7$ to $1.1 \times 10^9$ pfu). These results show that MAVS is a pivotal cellular antiviral protein whose expression level directly determines antiviral immunity.

Figure 5A:
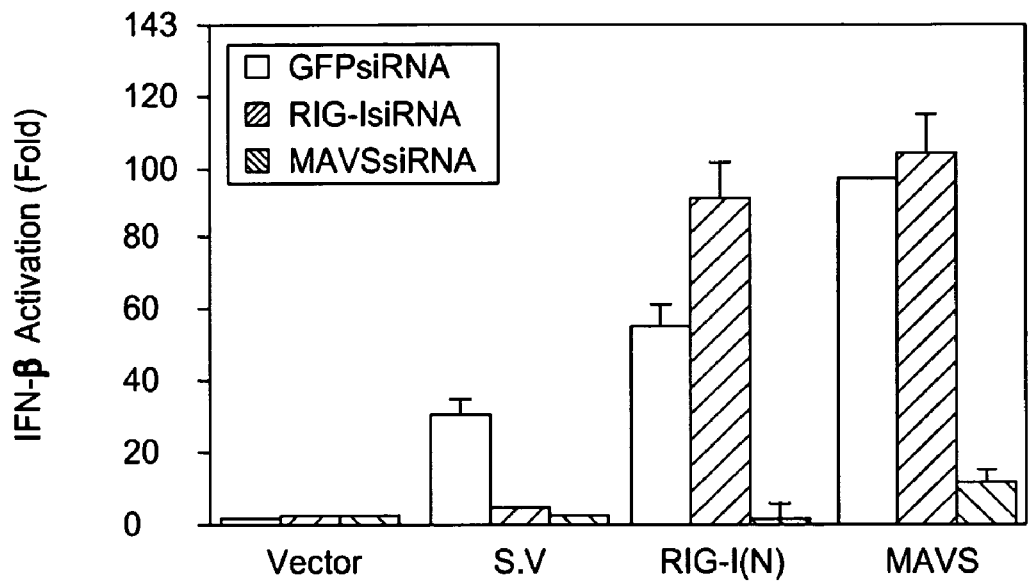
(FIG. 5A) HEK293 cells were transfected with siRNA oligos targeting GFP, RIG-I or MAVS. These cells were subsequently transfected with IFNβ-Luc together with expression vectors (300 ng) encoding the N-terminal fragment of RIG-I [RIG-I(N)], MAVS or empty vector (pcDNA3). As a positive control, cells were infected with Sendai virus (S.V). Twenty hours after viral infection or 24 hours after transfection of the expression plasmids, cells were harvested for luciferase assays.
Figure 5B:
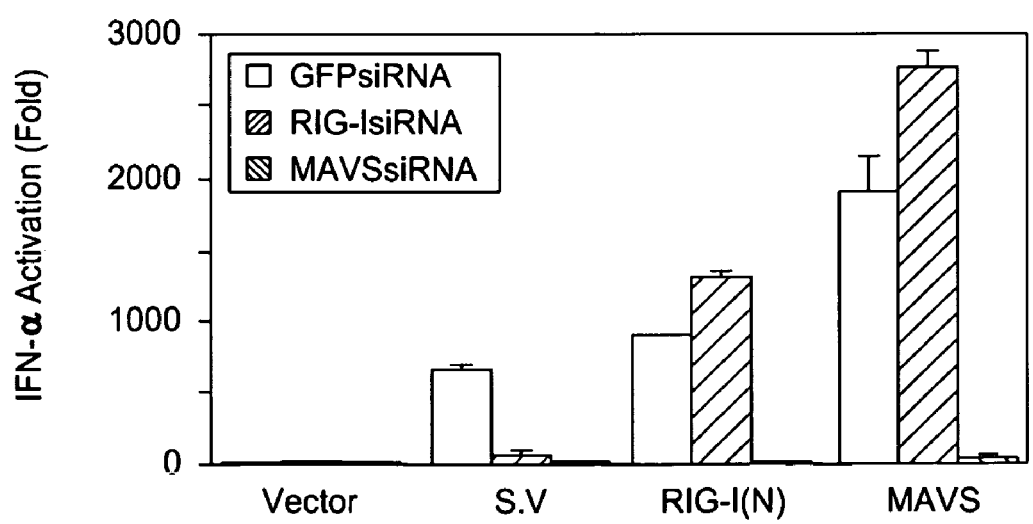
(FIG. 5B) Similar to (FIG. 5A) except that pIFNα4-Luc. (40 ng) and pcDNA3-FLAG-IRF7 (10 ng) were transfected into HEK293 cells to measure the activation of IFNα by IRF7.

MAVS Functions Downstream of RIG-I and Upstream of TBK1. As both RIG-I and MAVS function upstream of IKK and IRF3 activation, the inventors determined the epistatic relationship between these two proteins. As shown in FIG. 5A, RNAi of MAVS blocked IFN-β induction by Sendai virus, or by overexpression of the N-terminal fragment of RIG-I [RIG-I(N)] as well as MAVS itself. In contrast, RNAi of RIG-I did not inhibit IFN-β induction by the overexpression of MAVS. This pair of siRNA oligos blocked INF-β induction by Sendai virus, but not RIG-I(N), because the sequence targeted by the RNA oligos was located at nucleotides 2363-2381, outside the region encoding RIG-I(N). Similar to IFN-β, the IRF7-mediated induction of IFN-α by Sendai virus also required RIG-I and MAVS (FIG. 5B). Furthermore, RNAi of MAVS blocked IFN-α activation by RIG-I(N). In contrast, RNAi of RIG-I did not affect IFN-α induction by MAVS (FIG. 5B). Thus, MAVS functions downstream of RIG-I in the antiviral signaling pathway.

Figure 5C:
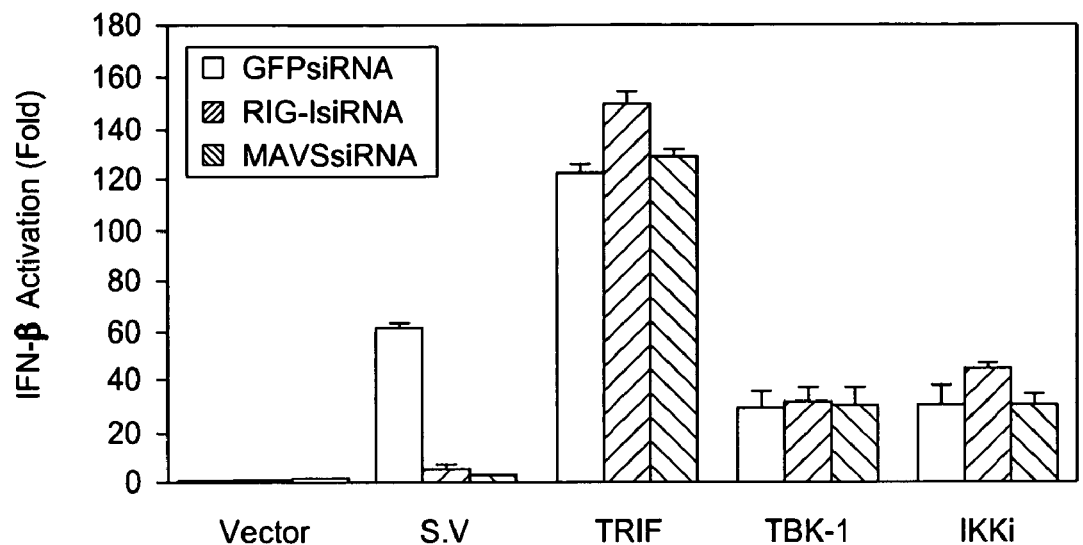
(FIG. 5C) Similar to (FIG. 5A) except that expression vectors (300 ng) for TRIF, TBK-1 and IKKε were used.
Figure 5D:
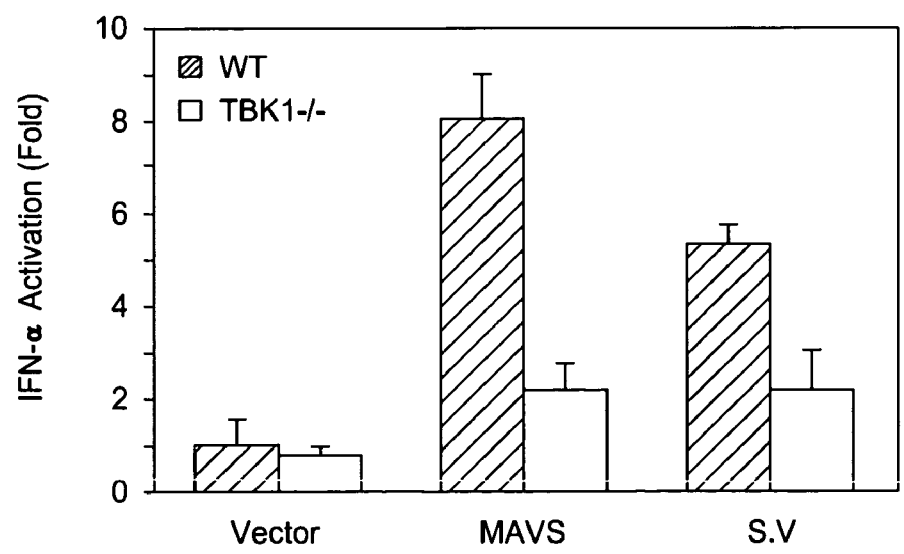
(FIG. 5D) Wild type or TBK1−/− MEF cells were transfected with pIFNα4-Luc (300 ng) and pcDNA3-FLAG-IRF7 (50 ng) together with pEF-HA-MAVS (100 ng) or control vector. For Sendai virus infection, MEF cells transfected with the luciferase reporter plasmids were infected with 50 HA units/ml of the virus.
Figure 5E:
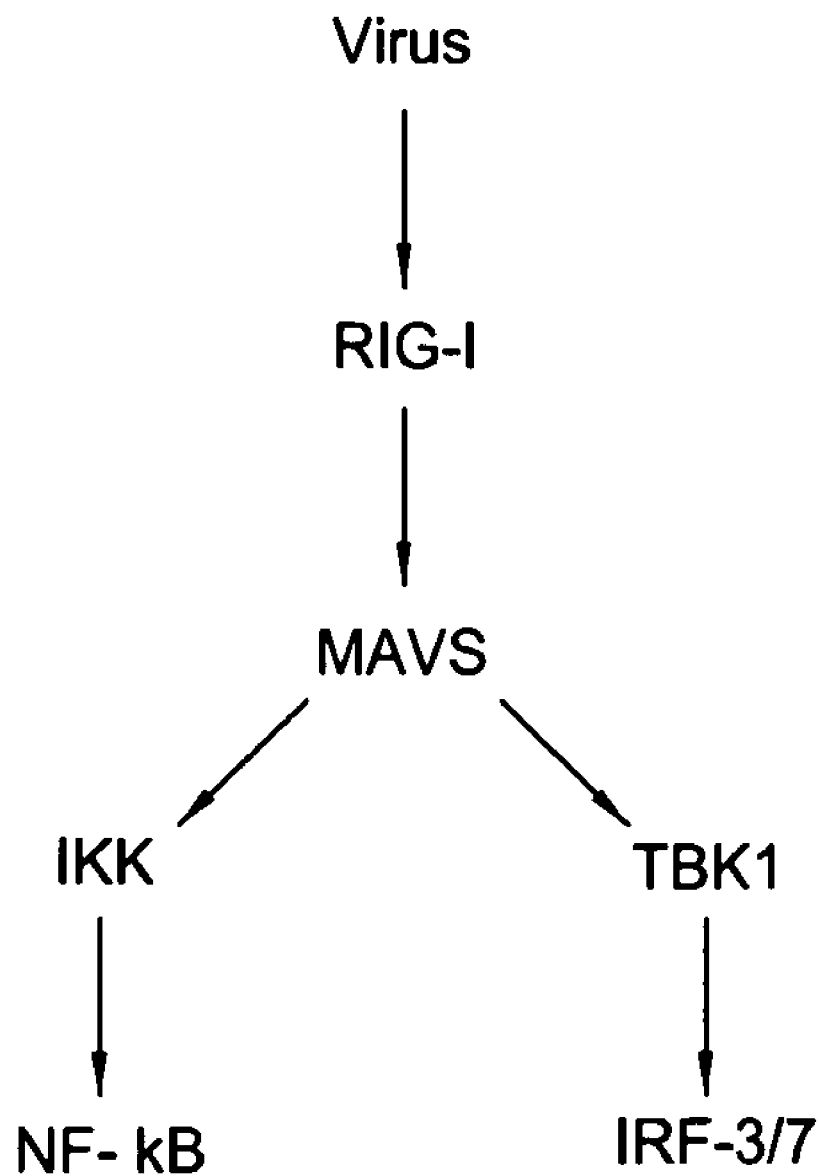
(FIG. 5E) A proposed antiviral signaling pathway. In this pathway, MAVS functions downstream of RIG-I, and upstream of IKK and TBK1.

Recent studies have shown that overexpression of TRIF, TBK1 or IKKε is sufficient to activate IFN-β, and that TBK1 and IKKε are the kinases that phosphorylate IRF3 at the C-terminus. Therefore the relationship between MAVS and TRIF, TBK1 and IKKε was investigated. While RNAi of MAVS abolished IFN-β induction by Sendai virus, it had no effect on the activation of IFN-β by TRIF, TBK1 or IKKε (FIG. 5C). Consistent with previous reports, RNAi of RIG-I did not affect IFN-β induction by TRIF, TBK1 or IKKε (Yoneyama et al., 2004). These results indicate that RIG-I and MAVS do not function downstream of TBK1 or IKKε. To determine if TBK1 or IKKε functions downstream of MAVS, the expression of TBK1 and IKKε by RNAi in HEK293 cells was knocked-down. Nine different pairs of TBK1 and five different pairs of IKKε siRNA oligos individually or in combination were used. Unexpectedly, none of the TBK1 and/or IKKε siRNA oligos blocked IFN-β induction by MAVS or Sendai virus (data not shown). The RNAi studies did not result in sufficient knock down of TBK1 or IKKε protein, thus TBK1-deficient MEF cells were used, which are known to be defective in producing interferons in response to Sendai virus infection. As shown in FIG. 5D, infection of Sendai virus or overexpression of MAVS induced IFN-α in the wild type MEF cells. In contrast, the IFN-α induction was greatly reduced in TBK1-deficient cells. Collectively, the results shown in FIGS. 3D, E, and FIG. 5 delineate a signaling pathway in which MAVS functions downstream of RIG-I and upstream of IKK and TBK1 (FIG. 5E).

Figure 6A:
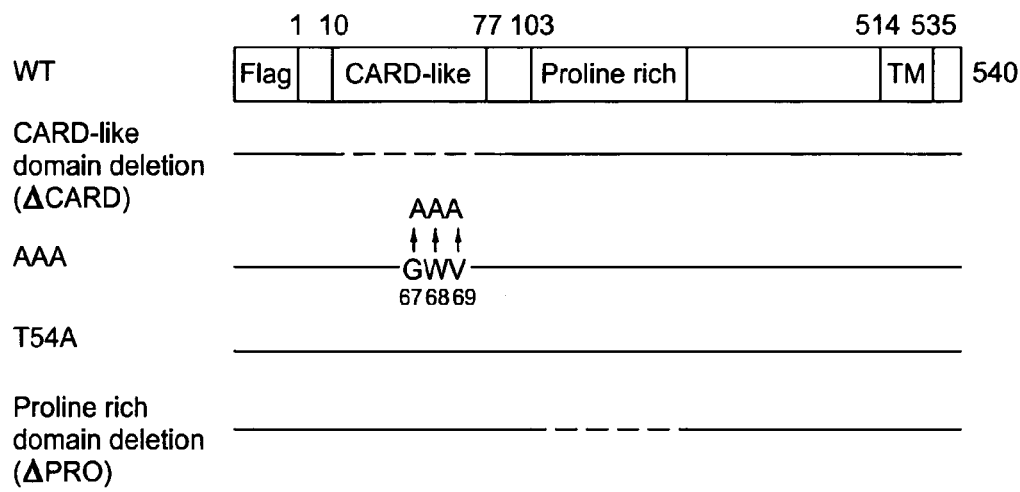
(FIG. 6A) A diagram illustrating the MAVS mutants. ΔCARD: lacking residues 10-77; ΔPRO: lacking residues 103-152; AAA: G67A/W68A/V69A.
Figure 6B:
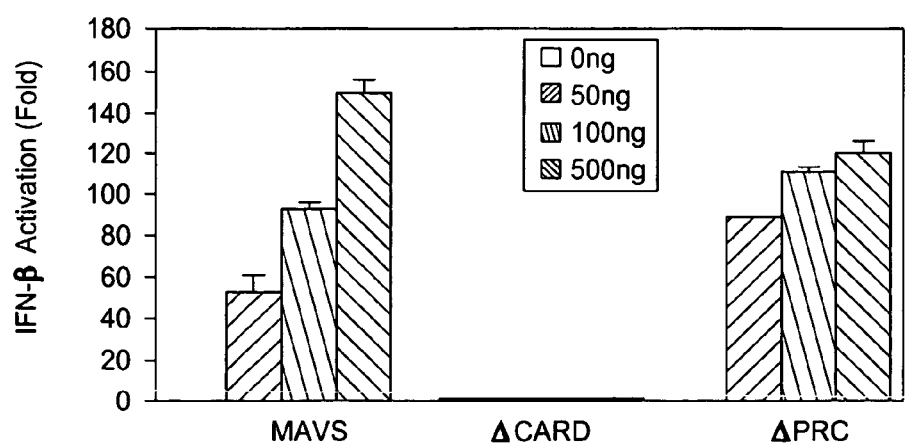
(FIG. 6B-FIG. 6D) HEK293 cells were transfected with IFNβ-Luc or κB3-Luc together with expression vectors for MAVS and its mutants as indicated.
Figure 6C:
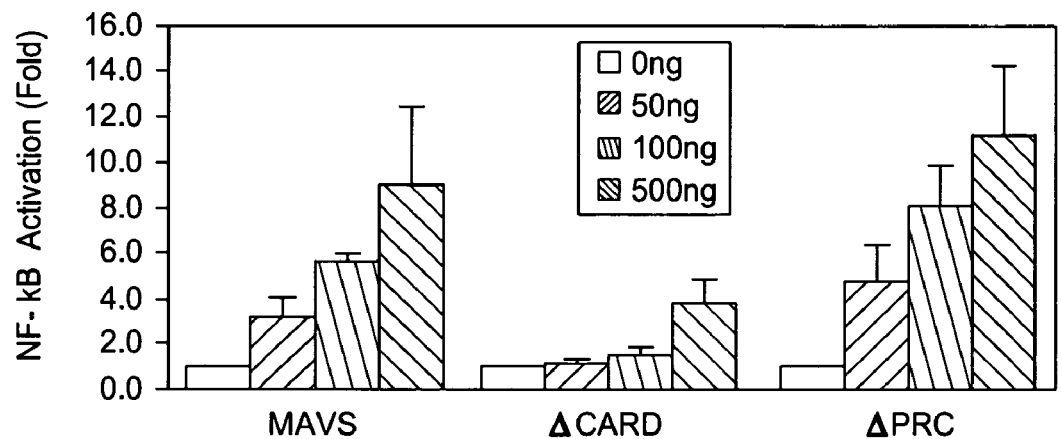
Figure 6D:
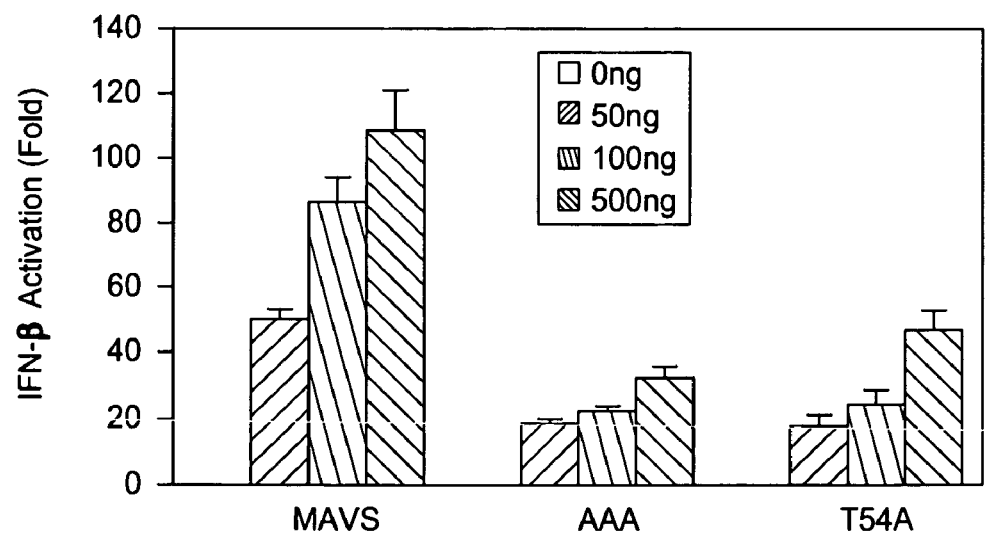
Figure 6E:
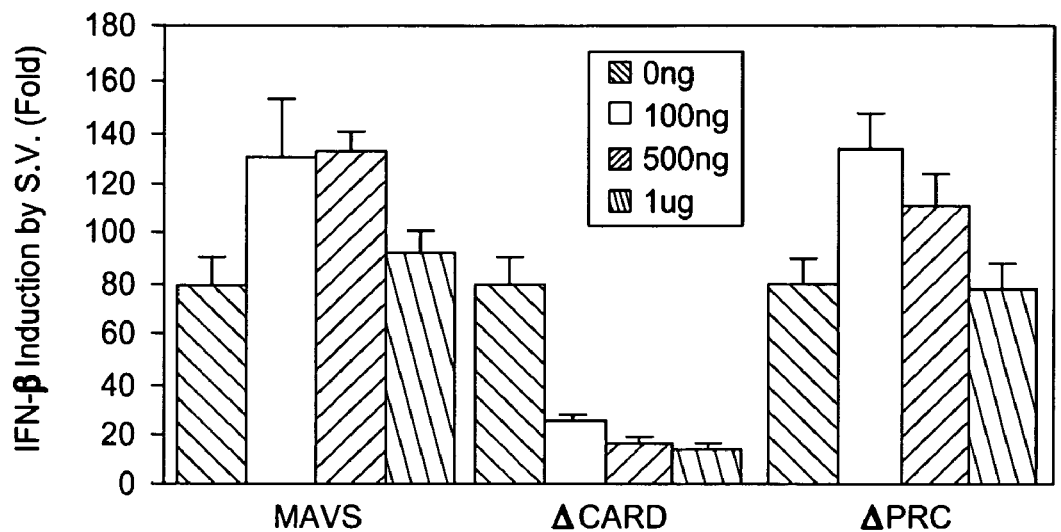
(FIG. 6E) The ΔCARD mutant of MAVS is a dominant negative inhibitor of IFN-β induction by Sendai virus. HEK293 cells were transfected with IFNβ-Luc together with expression vectors for MAVS or its mutants. The cells were then infected with Sendai virus for 20 hours followed by measurement of luciferase activity.
Figure 6F:
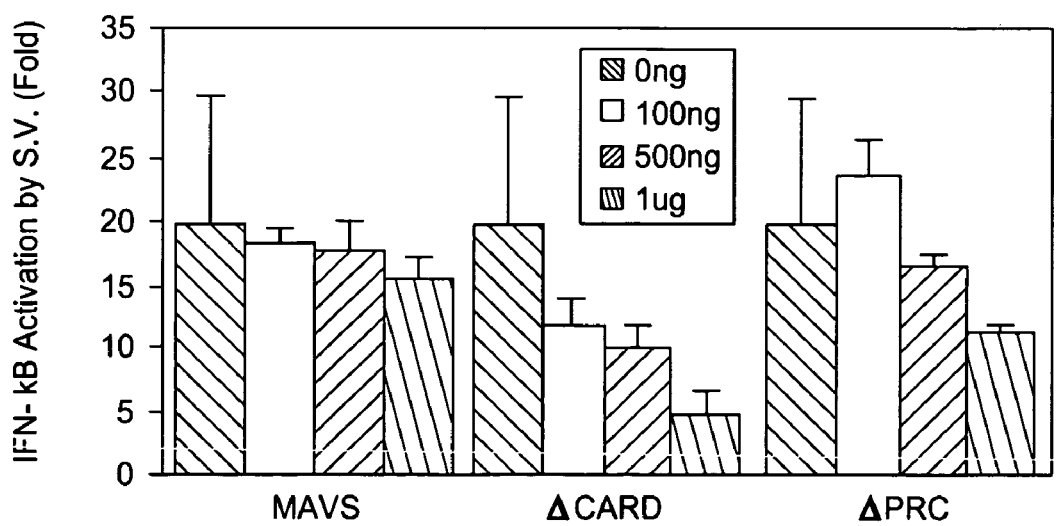
(FIG. 6F) Similar to (FIG. 6E), except that κB3-Luc was used instead of IFNβ-Luc.
Figure 10:
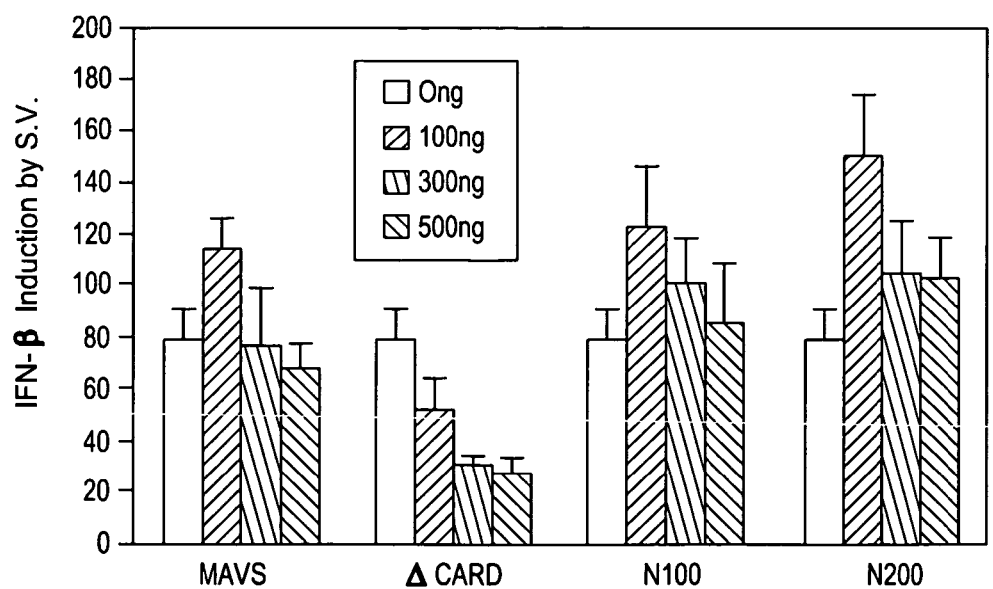
FIG. 10 shows that the CARD-like domain of MAVS does not inhibit IFN-β induction by Sendai virus. Expression vectors encoding the indicated proteins were transfected into HEK293 cells together with IFNβ-Luc. 24 hours after transfection, cells were infected with Sendai virus (50 HA units) to induce interferon-β. ΔCARD: MAVS lacking the N-terminal CARD-like domain. N100: N-terminal 100 residues of MAVS containing the CARD-like domain. N200: N-terminal 200 residues of MAVS containing the CARD-like domain and a portion of the PRO domain.

The CARD-like Domain is Essential for MAVS Signaling. The N-terminal CARD-like domain of MAVS is evolutionarily conserved (FIG. 1C). In addition, MAVS contains a proline-rich domain in the middle (FIG. 1A). To investigate the functions of these domains, expression constructs were engineered encoding MAVS mutant proteins lacking either the CARD-like domain (ΔCARD) or the proline-rich domain (ΔPRO; FIG. 6A). As shown in FIG. 6B and C, deletion of the CARD-like domain, but not the proline-rich domain, abolished the ability of MAVS to activate IFN-β or NF-κB. Furthermore, a point mutation of a conserved threonine residue to alanine (T54A), or simultaneous mutations of three conserved residues in the CARD-like domain to alanine (G67A/W68A/V69A; abbreviated as AAA), severely impaired the ability of MAVS to activate IFN-β (FIG. 6D). These results indicate that an intact CARD-like domain is essential for MAVS signaling. This conclusion was further supported by FIGS. 6E & F, which showed that MAVS-ΔCARD, but not MAVS-ΔPRO, functioned as a dominant negative mutant that inhibited the activation of IFN-β and NF-κB promoters by Sendai virus. The CARD-like domain alone did not function as a dominant negative mutant (FIG. 10), suggesting that when the CARD-like domain is not tethered to the rest of MAVS protein such as the membrane domain, it may not interact effectively with other proteins in the pathway.

Figure 7A:
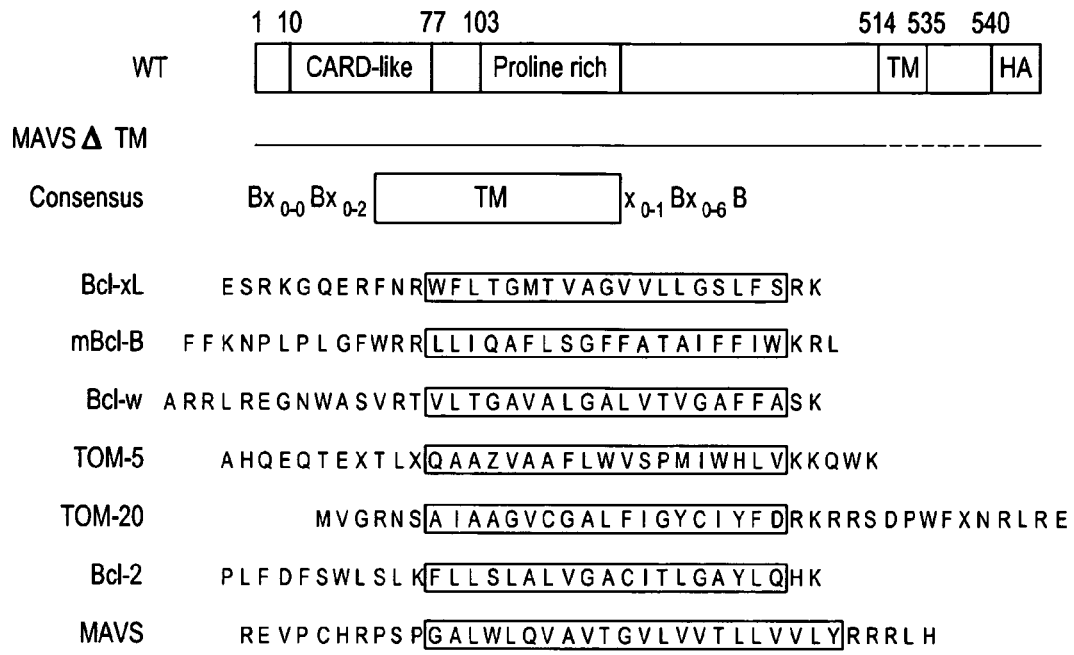
(FIG. 7A) MAVS contains a mitochondrial membrane targeting sequence that is essential for signaling. The left panel shows the alignment of the MAVS transmembrane (TM) sequence with those of known mitochondrial membrane proteins, including proteins of the Bcl-2 family. The MAVS mutant lacking the C-terminal 30 residues (ΔTM) is illustrated. This mutant or wild type (WT) MAVS was transfected into HEK293 cells together with IFNβ-Luc to measure IFN-β induction (right panel).
Figure 7A:
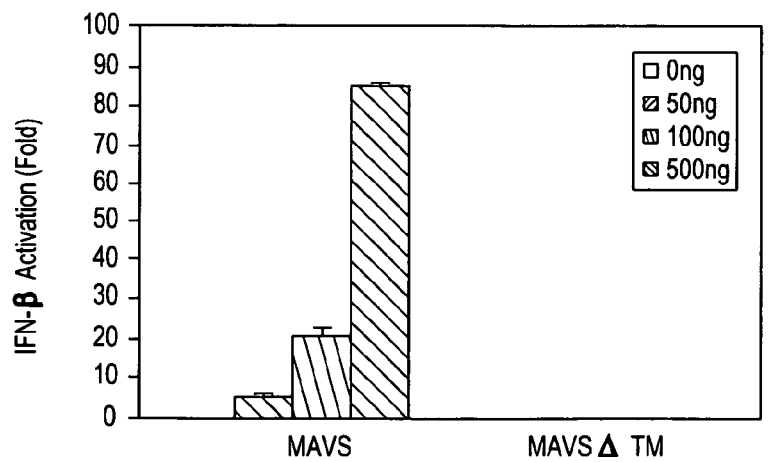
Figure 7B:
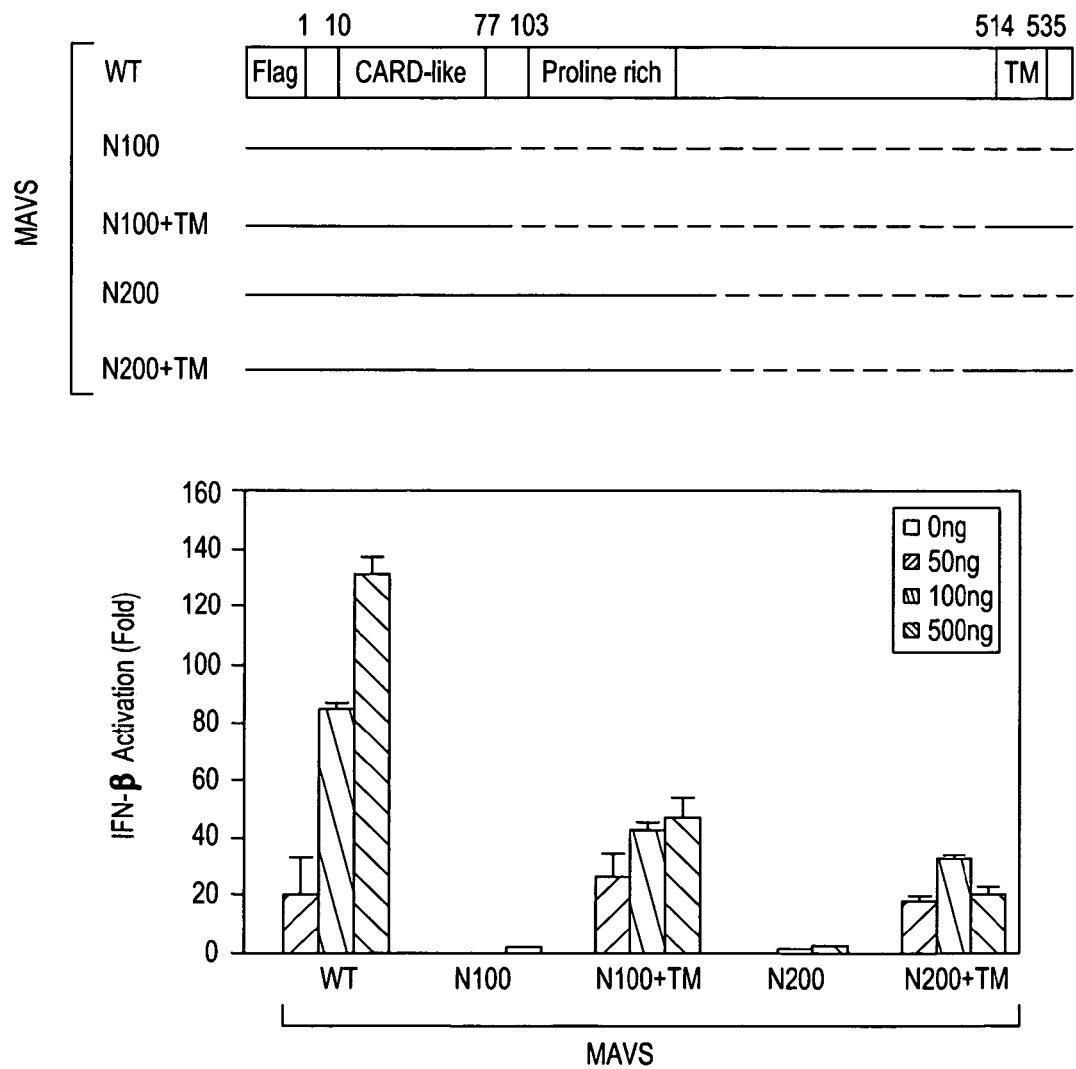
(FIG. 7B) A MAVS mutant containing the caspase activation and recruitment domains (CARD) and TM domain is sufficient to activate IFN-β. The MAVS mutants are illustrated on the left panel. These mutants were transfected into HEK293 cells together with IFNβ-Luc to measure IFN-β induction (right panel).

The C-terminal Transmembrane (TM) Domain of MAVS is Essential for its Function. Notably, the C-terminus of MAVS includes a conserved hydrophobic transmembrane (TM) domain, which resembles the TM domain of several tail-anchored mitochondrial proteins, including the proteins of the Bcl-2 family that protect cells from undergoing apoptosis (FIG. 7A, left panel; Kaufmann et al., 2003). To determine the function of this domain, a MAVS mutant protein lacking the C-terminal TM domain was made (MAVS-ΔTM). This mutant protein completely lost its ability to activate IFN-β (FIG. 7A, right panel). Immunoblotting studies showed that MAVS-ΔTM was abundantly expressed and became a soluble cytosolic protein, whereas the full-length MAVS was present in membrane pellets (data not shown; also see FIG. 7C for confocal image).

The CARD-like and TM Domains of MAVS are Sufficient to Induce IFN-β. Since the most conserved regions of MAVS are the N-terminal CARD-like domain and the C-terminal TM domain, and each of these domains is necessary for MAVS signaling, whether these two domains are sufficient to activate IFN-β expression was examined. Remarkably, the MAVS mutant with only the CARD-like and TM domains (N100+TM) was sufficient to induce IFN-β (FIG. 7B), whereas the mutants with only the CARD-like domain were inactive. Thus, the CARD-like and TM domains are both necessary and sufficient for MAVS signaling.

Figure 7C:
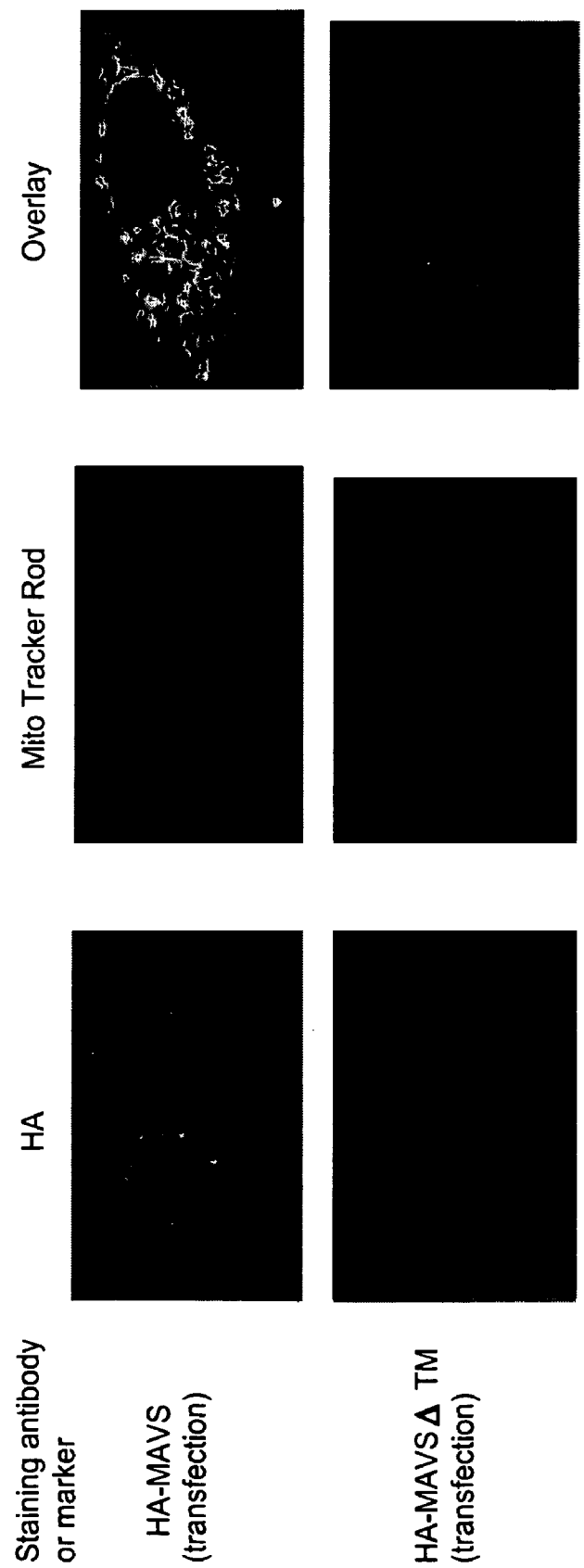
(FIG. 7C) MAVS is a mitochondrial protein. pEF-HA-MAVS was transfected into HeLa cells, which was then stained with an HA antibody and imaged by confocal microscopy. The mitochondria were stained with Mito Tracker. The yellow staining in the overlay image indicates co-localization of MAVS and Mito Tracker.
Figure 11A:
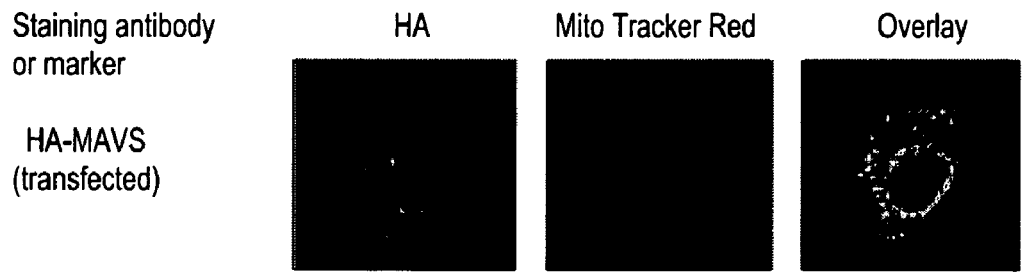
(FIG. 11A) MAVS is localized to mitochondria, not ER. The HA-MAVS expression construct was transfected into HeLa cells, which are then stained with an HA antibody and visualized by confocal microscopy. The mitochondria and ER were marked by staining with the Mito Tracker Red and calnexin antibody, respectively.
Figure 11A:
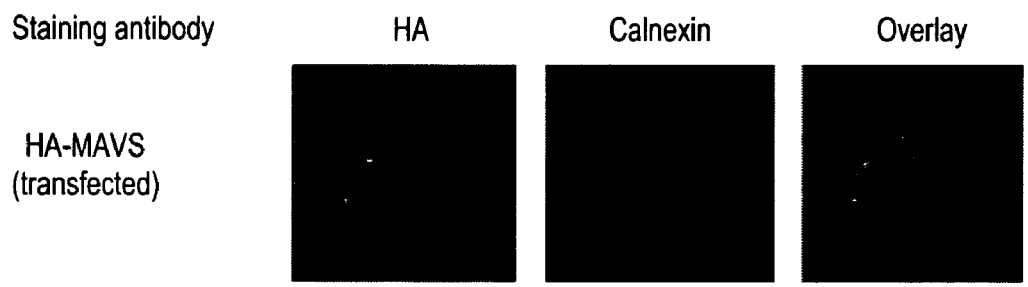
Figure 11B:
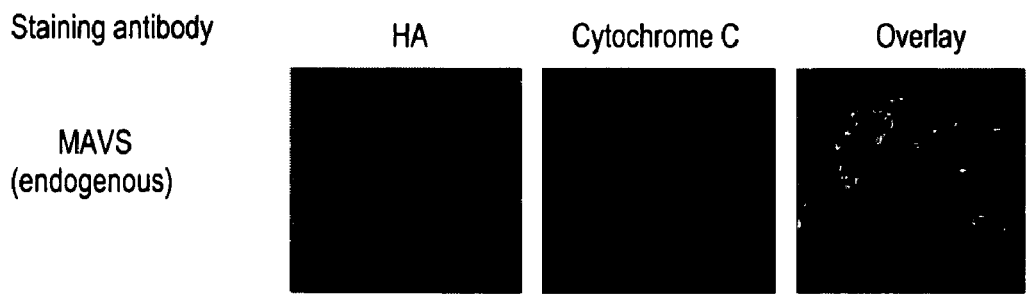
(FIG. 11B) Confocal microscopy of the endogenous MAVS protein. HeLa cells were permeabilized and stained with an antibody against MAVS or cytochrome c.

MAVS is a Mitochondrial Membrane Protein. To determine the subcellular localization of MAVS, confocal microscopy to image HeLa cells transfected with an expression vector encoding HA-tagged. MAVS was used (FIG. 7C, upper panel). Fluorescent immunostaining with an HA-specific antibody showed a punctate pattern of MAVS localization that overlapped with the staining pattern of Mito Tracker, a fluorescent marker taken up specifically by mitochondria. It was found by confocal microscopy that MAVS lacking the C-terminal transmembrane domain (MAVS-ΔTM) was a cytosolic protein that no longer overlapped with Mito Tracker staining (FIG. 7C, lower panel). As the C-terminal TM domain of MAVS is similar to that of Bcl-2, which is localized to both endoplasmic reticulum (ER) and mitochondria, whether a fraction of MAVS might be localized to ER was examined. As shown in FIG. 11A, the staining pattern of MAVS did not overlap with that of the ER marker calnexin, indicating that MAVS is predominantly not an ER protein. To localize the endogenous MAVS protein, the affinity-purified MAVS antibody for imaging was used (FIG. 11B). Similar to the transfected HA-MAVS, the endogenous MAVS also showed a punctate staining pattern that overlapped with the staining of cytochrome c, a well-known mitochondrial protein. Although the resolution of confocal microscopy did not allow for the precise localization of MAVS at the ultra-structural level within the mitochondria, these studies clearly show that MAVS is localized to the mitochondria.

Figure 7D:
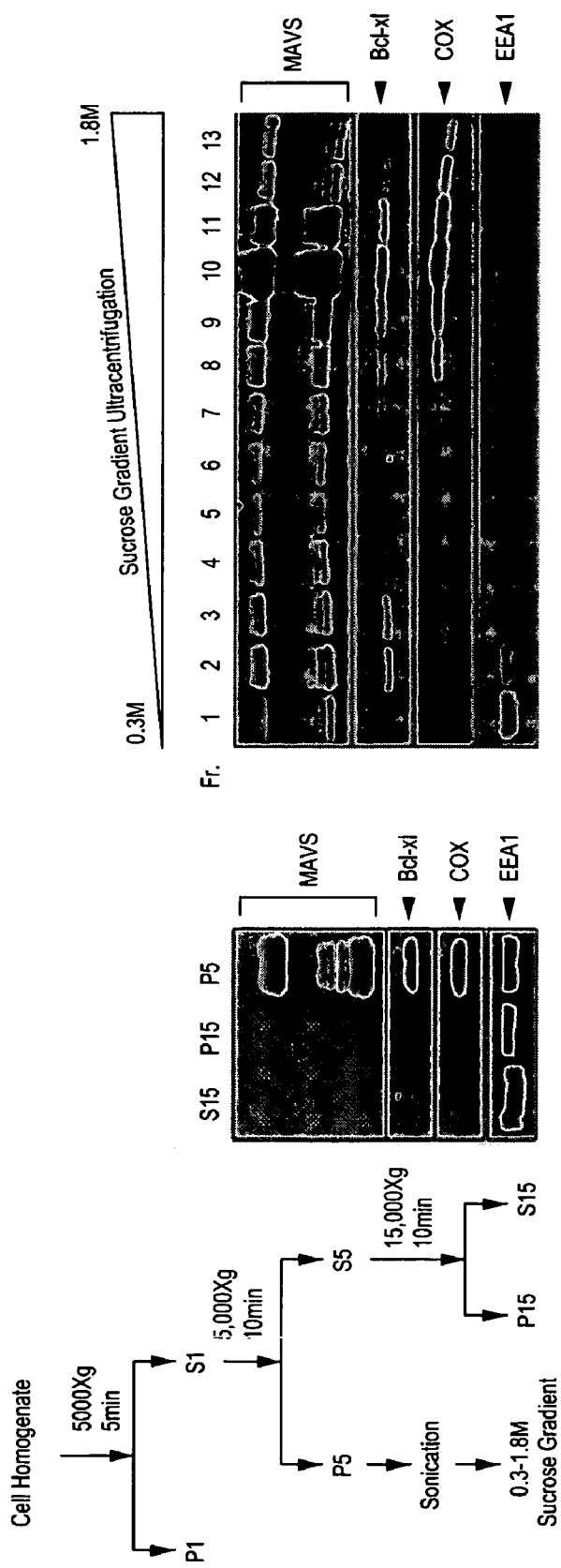
(FIG. 7D) Subcellular fractionation of MAVS. HEK293 cells were homogenized in an isotonic buffer and then subjected to differential centrifugation as shown in the diagram. Different fractions as indicated were analyzed by immunoblotting with antibodies against MAVS, Bcl-xL (outer mitochondrial membrane), COX (inner mitochondrial membrane), and EEA1 (endosome marker). On the right panel, the crude mitochondrial fraction (P5) was sonicated to disrupt the outer mitochondrial membrane and then fractionated by sucrose gradient ultracentrifugation. The fractions were inmunoblotted with the indicated antibodies.

To further determine if MAVS is localized to the mitochondrial membrane, subcellular fractionation studies were carried out. HEK293 cells were homogenized in an isotonic buffer that preserved mitochondria and other organelles, and the cell lysates were then subjected to differential centrifugation to separate nuclei, mitochondria, and other organelles as well as cytosol (FIG. 7D). MAVS was found in the 5,000×g pellet (P5), together with other mitochondrial proteins including Bcl-xL and cytochrome-c oxidase (COX). Immunoblotting with an antibody against the endosomal protein EEA-1 showed that the distribution of this protein did not correlate with that of MAVS. Similarly the markers of endoplasmic reticulum (BiP) and lysosome (LAMP-1) did not co-segregate with MAVS (data not shown).

To determine whether MAVS is localized in the outer or inner mitochondrial membrane, the mitochondrial fraction (P5) was sonicated to partially rupture the outer mitochondrial membrane and then fractionated by sucrose gradient ultracentrifugation (FIG. 7D). The sonication released cytochrome c from the intermitochondrial membrane space, and resulted in a small fraction of outer mitochondrial membrane floating on the top of the sucrose gradient, as indicated by immunoblotting with an antibody against Bcl-xL, which is predominantly located in the outer mitochondrial membrane. Under the same condition, the inner mitochondrial membrane protein COX remained largely in the dense fractions of the sucrose gradient. Interestingly, a small fraction of MAVS co-migrated with Bcl-xL to the lighter membrane fractions, suggesting that MAVS co-localizes with Bcl-xL in the outer mitochondrial membrane. This conclusion was further supported by the observation that MAVS and Bcl-xL could be extracted from the mitochondrial membrane with the same concentration of Triton X-100 (0.1%), whereas the extraction of COX requires higher Triton X-100 concentration (0.2%, data not shown).

Figure 7E:
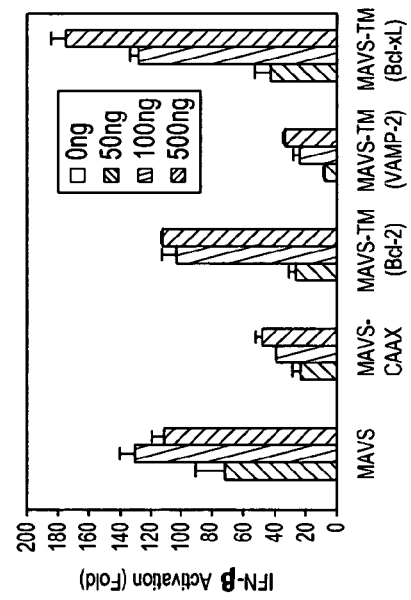
(FIG. 7E) Mislocalization of MAVS impairs its function. Expression vectors for the MAVS fusion proteins as indicated on the left panel were transfected into HEK293 cells together with IFNβ-Luc to measure IFN-β induction (right panel). The expression levels and subcellular localization of the MAVS fusion proteins are shown in FIGS. 11C & D (below).
Figure 7F:
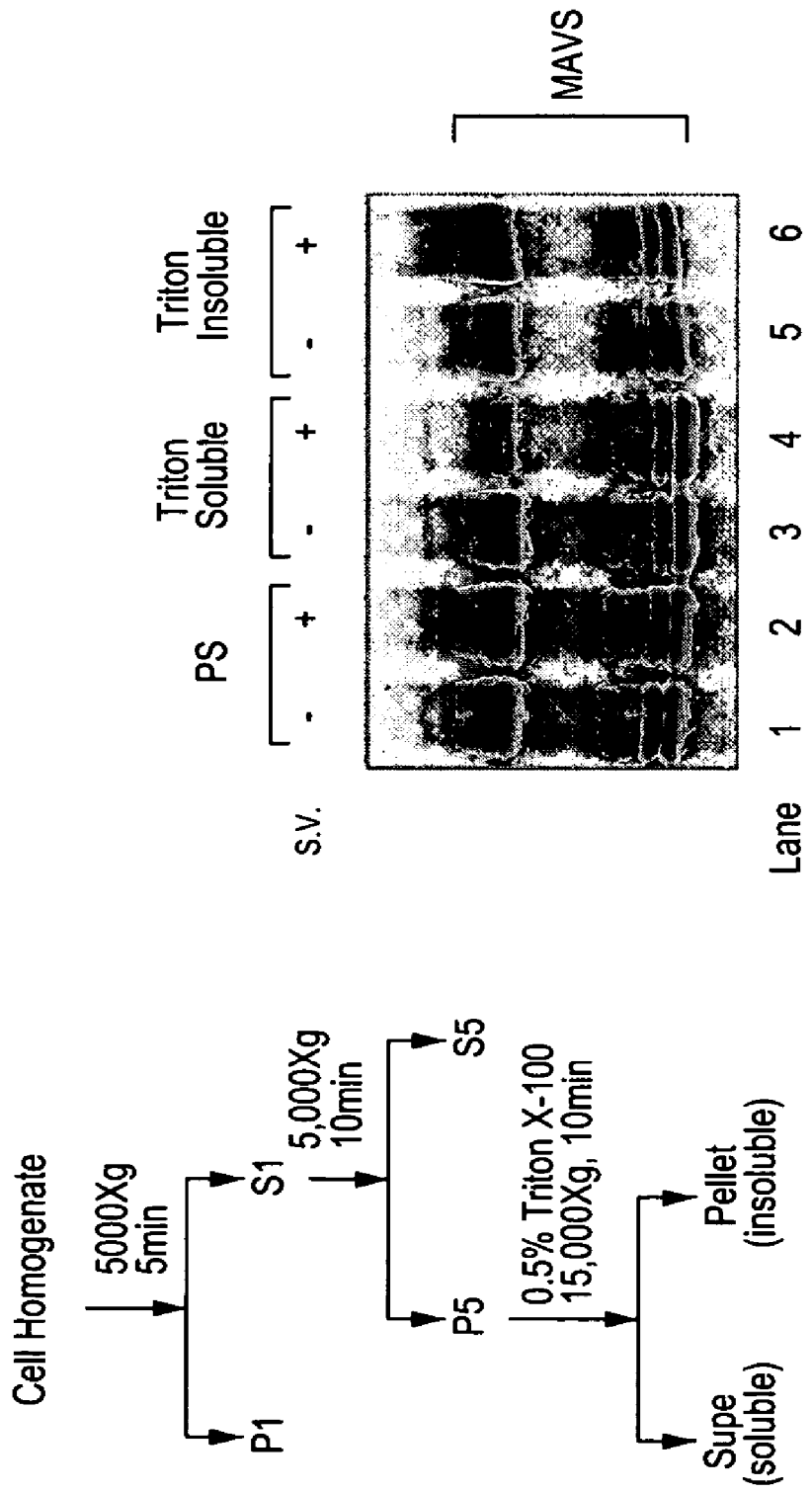
(FIG. 7F) MAVS translocates to a detergent insoluble membrane domain following viral infection. The mitochondrial fraction (P5) isolated from mock or viral infected HEK293 cells was resuspended in a buffer containing 0.5% Triton X-100, and the detergent soluble and insoluble materials were then analyzed by immunoblotting for the presence of MAVS.
Figure 11C:
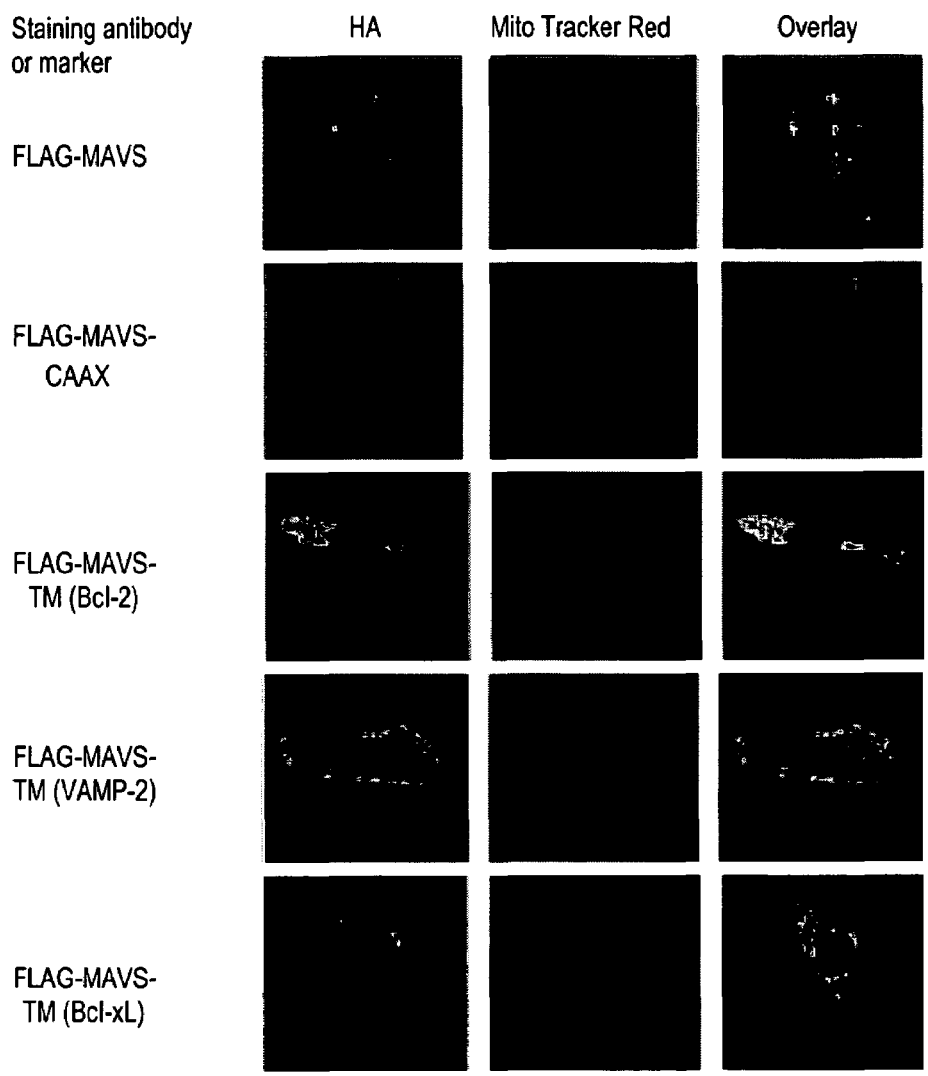
(FIG. 11C) Subcellular localization of MAVS fusion proteins containing different membrane targeting sequences. The MAVS fusion protein as depicted in FIG. 7E were transfected into HeLa cells and visualized by immunostaining with the FLAG antibody followed by confocal microscopy. Mito Tracker Red was used in the same cells to stain mitochondria. Note that the staining pattern of MAVS is indistinguishable from that of MAVS-TM (Bcl-XL; compare top and bottom panels). The VAMP-2 fusion protein is also distributed in other endomembranes that presumably originate from ER.
Figure 11D:
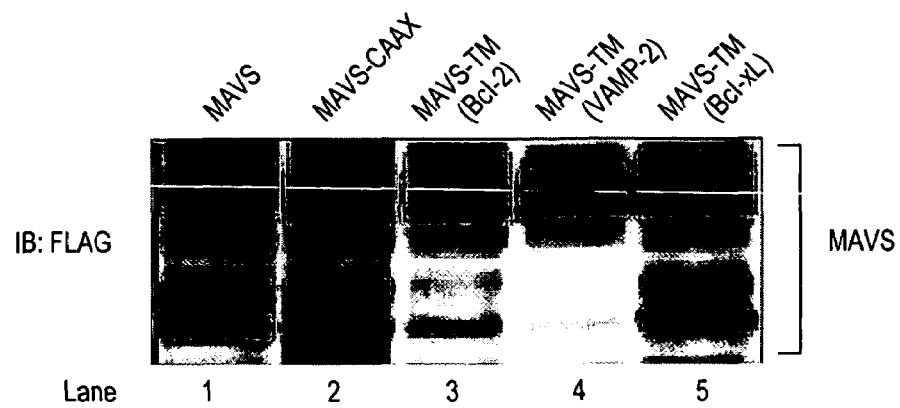
(FIG. 11D) Expression of MAVS fusion proteins in HEK293 cells. Membrane pellets containing the MAVS fusion proteins as depicted in FIG. 7E, above, were resuspended in SDS sample buffer and immunoblotted with the FLAG antibody.

Mislocalization of MAVS Impairs Its Function. MAVS is predominantly localized to the mitochondrial membrane (FIGS. 7C & D), and that removal of the mitochondrial targeting sequence abolishes its activity (FIGS. 7A & B). To further examine the importance of mitochondrial localization for MAVS function, the C-terminal TM domain of MAVS with peptide sequences that target MAVS to different membrane locations was replaced. These sequences include the CAAX motif from Rac1 that is known to target fusion proteins predominantly to the plasma membrane (Michaelson et al., 2001); the ER targeting sequence from VAMP-2 (vesicle associated membrane protein-2), which is predominantly an ER membrane protein (Kim et al., 1999); the TM sequence from Bcl-2, which is localized in both ER and mitochondria (Kaufmann et al., 2003); and the TM sequence from Bcl-xL, which is predominantly in the mitochondrial outer membrane (Kaufmann et al., 2003). As shown in FIG. 7E, replacement of the TM domain of MAVS with the analogous domain from Bcl-2 or Bcl-xL did not impair the ability of MAVS to induce IFN-β. In contrast, the mislocalization of MAVS to the plasma membrane (CAAX) or ER (VAMP-2) markedly reduced the activity of MAVS. Confocal microscopy studies confirmed that the majority of MAVS fusion proteins with the CAAX or VAMP-2 targeting sequences were no longer present in the mitochondria, whereas the fusion proteins containing the Bcl-2 or Bcl-xL targeting sequences were predominantly in the mitochondria (FIG. 11C). The residual activity (20-30% of the wild type MAVS) may be due to incomplete mislocalization of the overexpressed MAVS proteins. Taken together, these results demonstrate the importance of mitochondrial localization for the signaling function of MAVS.

MAVS is Resistant to Detergent Extraction From Membranes Following Viral Infection. Since there were no difference detected for the MAVS protein at the level of expression or modification after viral infection, the localization of MAVS changes in response to viral infection was determined. It was found that Sendai virus did not cause the translocation of MAVS from mitochondria to cytosol (data not shown). However, when the mitochondrial fraction (P5) was further extracted with 0.5% Triton X-100, the majority of MAVS was extracted from mitochondrial membranes isolated from mock-infected cells, but not from viral infected cells. In fact, MAVS was even resistant to extraction with 1% Triton X-100 following viral infection (data not shown). These results suggest that MAVS translocates to a detergent resistant membrane domain or particle following viral infection.

The present inventors have identified and characterized MAVS as a novel cellular protein essential for innate immune defense against viruses. It is shown that the overexpression of MAVS is sufficient to activate the NF-κB, IRF3 and IRF7 pathways to induce type-I interferons including IFN-α and IFN-β, which inhibit viral replication. Conversely, silencing of endogenous MAVS expression by RNAi abolishes the activation of NF-κB, IRF3 and IRF7, thus blocking the production of interferons and permitting viral infection. Epistasis studies show that MAVS functions downstream of the viral RNA receptor RIG-I and upstream of IκB and IRF3 phosphorylation. MAVS contains an N-terminal CARD-like domain and a C-terminal mitochondrial membrane targeting domain, both of which are essential for MAVS signaling. The mitochondrial localization of MAVS is particularly interesting, as this is the first example of a mitochondrial protein playing a pivotal role in innate immunity. MAVS is also the first mitochondrial protein known to activate NF-κB and IRF transcription factors.

Figure 12A:
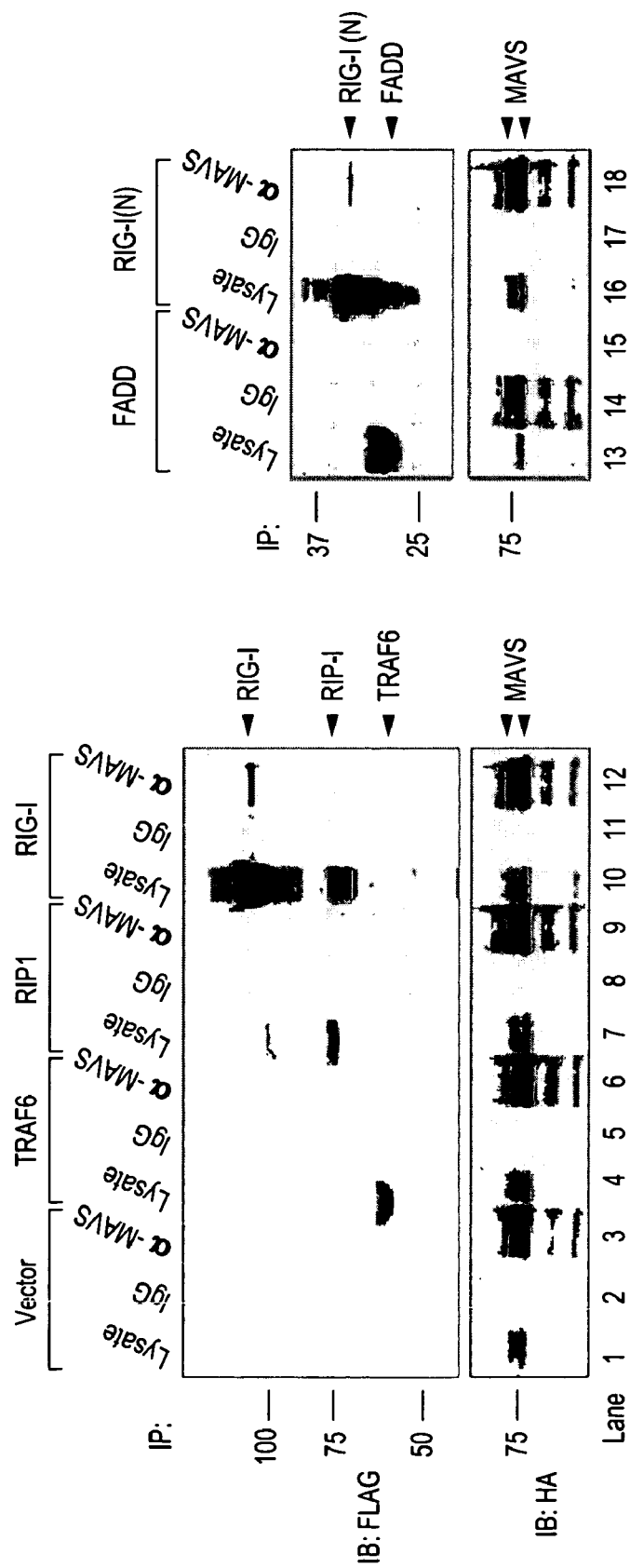
(FIG. 12A) Expression vectors encoding HA-MAVS and the indicated FLAG-tagged proteins were co-transfected into HEK293 cells. 36 hours after transfection, cells were lysed in a buffer containing 0.5% Triton-X100 and 150 mM NaCl, and the proteins associated with MAVS were co-immunoprecipitated with the polyclonal antibodies against MAVS or control IgG. After washing three times with a buffer containing 0.1% Triton-X100 and 150 mM NaCl, the immunoprecipitated beads were resuspended in SDS sample buffer, and the eluted proteins immunoblotted with an antibody against FLAG or HA as indicated. Lysate represents 10% of the starting materials used for immunoprecipitation.

The N-terminal CARD-like domain of MAVS likely mediates interaction with other CARD-containing proteins. The logical candidates of MAVS interacting protein include the CARD-like domain proteins RIG-I and MDA-5. Indeed, weak but reproducible binding was detected between MAVS and RIG-I in co-immunoprecipitation studies when these proteins were overexpressed together (FIG. 12A). However, it was not possible to detect any direct interaction between endogenous MAVS and RIG-I in the presence or absence of viral infection, nor was translocation of RIG-I to the mitochondria observed following viral infection. Both RIG-I and MDA-5 contain two CARD-like domains, which may interact with each other intra-molecularly, thus preventing their interaction with other CARD domain proteins. The binding of viral RNA to the C-terminal RNA helicase domain of RIG-I may induce a conformational change that allows the tandem CARD domains of RIG-I to interact with MAVS directly or indirectly. More extensive studies are required to determine the validity and functional significance of interaction between RIG-I and MAVS.

Figure 12B:
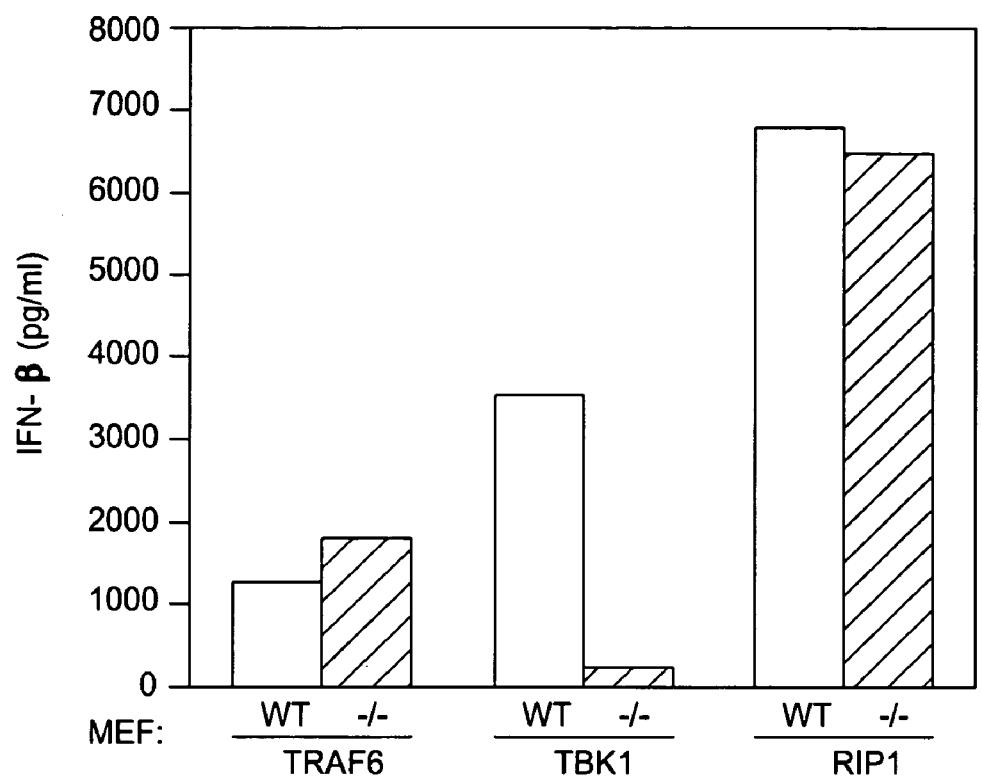
(FIG. 12B) Normal induction of interferon-β in MEF cells lacking TRAF6 or RIP1. The indicated knockout MEF cell lines and paired wild type controls were infected with Sendai virus (50 HA units/ml) for 24 hours. The cultured media were used to measure the production of endogenous IFN-β by ELISA.

How MAVS activates NF-κB and IRF3 is currently unknown. The NF-κB pathway is primarily regulated by the activation of IKK, which integrates signals from multiple pathways. The mechanisms of IKK activation by extracellular ligands such as TNFα and IL-1β have been extensively studied (Sun and Chen, 2004). In these pathways, several proteins including TRAF2, TRAF6, RIPI, TAK1 and TAB2 have been shown to be important for IKK activation. The potential interaction of these proteins with MAVS was examined, and found that only TRAF6 could weakly associate with MAVS (FIG. 12A), presumably through a putative TRAF6-binding sequence in the proline rich region of MAVS (PGENSE, residues 153-158;. (Ye et al., 2002). However, deletion of this region had no effect on the ability of MAVS to induce IFN-β (FIG. 6B) or NF-κB (FIG. 6C). Furthermore, IFN-β induction by Sendai virus was not impaired in TRAF6-deficient MEF cells (FIG. 12B). Recently, it has been shown that RIP1 and FADD are involved in viral induction of IFN-β (Balachandran et al., 2004), raising the possibility that these proteins mediate signaling by MAVS. However, there was no interaction between MAVS and RIP1 or FADD (FIG. 12A) detcted. Furthermore, the RIP1-deficient MEF cells were fully capable of producing IFN-β in response to Sendai virus infection (FIG. 12B). Nor was there any detectable, direct interaction between MAVS and any subunit of the IKK complex, including IKKα, IKKβ and NEMO. Thus, it appears that none of the proteins known to be involved in the classical pathways of IKK activation is a direct link between MAVS and IKK activation.

The localization of MAVS to the mitochondria provides a strategic position to detect viral replication, which often occurs in intracellular organelles such as endoplasmic reticulum (ER). For example, the replication of hepatitis C virus (HCV) RNA occurs in a membranous web that connects ER and mitochondria (Rehermann and Nascimbeni, 2005). The HCV core protein has also been found to reside in the mitochondrial membrane (Schwer et al., 2004). The dsRNA, which is present in the viral RNA-protein particles, may recruit the RNA helicase RIG-I and MDA-5 to the membranous web, allowing these proteins to interact with MAVS directly or indirectly. The signal of viral replication may then be transmitted to the mitochondria, which triggers antiviral responses through activation of NF-κB and IRF3.

Figure 13:
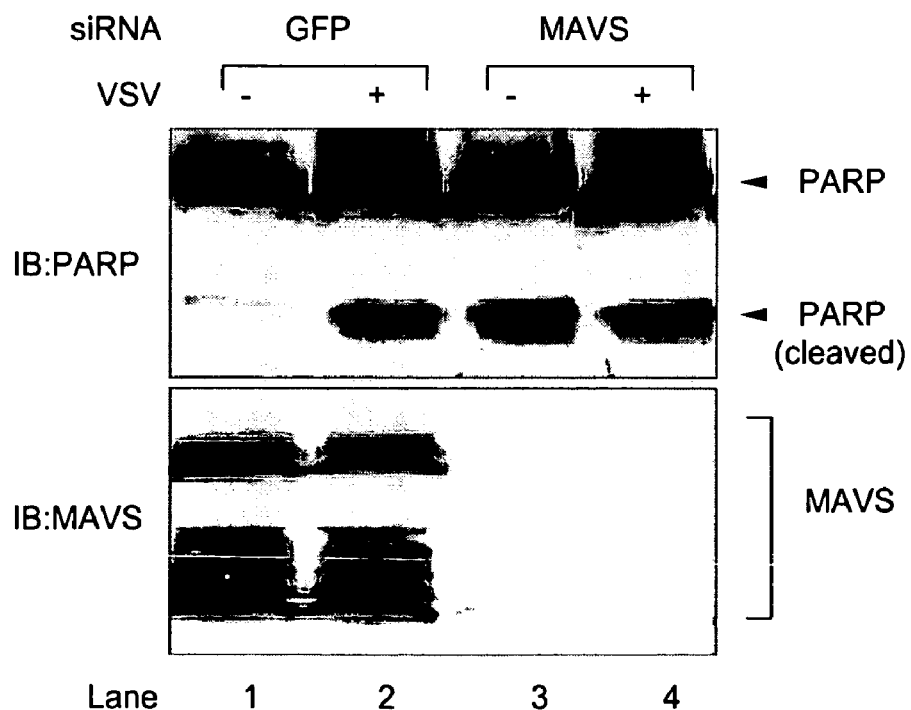
FIG. 13 shows that MAVS protects cells from apoptosis. HEK293 cells were transfected with siRNA targeting GFP (control) or MAVS. 48 hr after transfection, cells were infected with VSV for 24 hours before lysates were prepared and immunoblotted with an antibody against PARP.

Mitochondria represent the best example of harmonious symbiosis between the ancient bacteria and eukaryotic cells. From this bacterial origin, mitochondria have further evolved as a sentinel of intrinsic and extrinsic stress or insults to the cell. The role of mitochondria in apoptosis is an excellent example of how mitochondria govern the homeostasis and wellness of an organism by regulating cell death in response to stress signals (Wang, 2001). Several apoptotic and anti-apoptotic proteins are localized to the mitochondria. The first mitochondrial protein known to be involved in apoptosis is the proto-oncogene Bcl-2 (Hockenbery et al., 1990), which has a C-terminal-mitochondrial transmembrane domain similar to that of MAVS. In normal cells, the Bcl-2 family of proteins prevents the release of pro-apoptotic molecules such as cytochrome c and SMAC/DIABLO from the mitochondria to the cytoplasm. In response to an apoptotic stimulus such as DNA damage, cytochrome c and SMAC are released to the cytosol to initiate a caspase cascade leading to cell death. It is not clear whether MAVS activates NF-κB and IRF3 by mobilizing other mitochondrial components or through direct interaction with proteins functioning in the NF-κB and IRF3 pathways. Although much more work is required in order to elucidate the biochemical mechanism of MAVS signaling, our studies have uncovered a new role of mitochondria in innate immunity against pathogenic insults such as viral infection. Thus, mitochondria may have a central role in integrating signals from pathogenic challenge and orchestrating an immune or apoptotic response depending on the challenge. In this regard, members in several families of proteins involved in cell death have recently been shown to function in the immunity pathways. Examples of these proteins include caspase-8/Dredd, IAPs, and paracaspase (e.g., MALT1; van Oers and Chen, 2005). The CARD domain proteins, including APAF1, NOD1, NOD2, RIP2, RIG-I and now MAVS, represent another example of proteins that have pivotal functions in apoptosis as well as immunity. MAVS is particularly unique in that it is a CARD domain protein localized in the mitochondrial membrane, suggesting that it may also be involved in apoptosis. Indeed, our preliminary studies suggest that RNAi of MAVS in HEK293 cells led to a partial cleavage of PARP [POLY (ADP-ribose) polymerase; FIG. 13], an early marker of apoptosis, suggesting that MAVS may protect cells from apoptosis. Thus, unlike other antiviral mechanisms that trigger the apoptosis of infected cells to limit viral spread, MAVS may help the survival of infected cells while mounting a potent interferon response to clear viral infection.

It was also shown that higher expression of MAVS endows cells with stronger immunity to viral infection, whereas the loss of MAVS expression renders cells vulnerable to viral killing. These results raise the possibility that variations in the expression levels of MAVS may endow different individuals with differential immunity against viral diseases. As many viruses have evolved to acquire strategies to evade host immunity, it is quite possible that some viruses may target MAVS in order to achieve successful infection. In these cases, therapies that enhance MAVS expression or activity may be a viable option for achieving beneficial immune responses against viral diseases.

Plasmids and Cell Lines. MAVS sequence was amplified by PCR using the IMAGE clone 5751684 (ATCC) as a template. PCR primers were based on GenBank accession number BC044952. The open reading frame of MAVS was cloned into the XhoI and MluI sites of the mammalian expression vector pEF-IRES-Puro such that N-terminal HA-tagged MAVS can be expressed under the control of EF1α promoter. pcDNA3-FLAG-MAVS was constructed by cloning MAVS into the XhoI and XbaI sites of pcDNA3. Truncated forms of MAVS lacking either the CARD-like domain (residues 10-77) or the proline rich region (residues 103-152) were cloned into pcDNA3 using overlap extension PCR. A similar PCR strategy was used to generate MAVS mutants lacking the intervening sequence between the CARD and TM domains (N100+TM and N200+TM). To replace the TM domain of MAVS with another domain that targets the fusion protein to distinct membrane locations, the following sequences were used: CAAX (residues 128-148 of Rac1); VAMP-2 (residues 84-116); Bcl-2 (residues 208-239) and Bcl-xL (residues 202-233). These sequences were fused to the C-terminus of MAVS (residues 1-500) using overlap extension PCR. Point mutations within the CARD-like domain of MAVS were introduced using the QuickChange kit (Strategene). pEF-BOS-FLAG-RIG-I and RIG-I(N) were kindly provided by Dr. Takashi Fujita (Tokyo Metropolitan Institute of Medical Science). cDNA encoding amino acids 1-242 of RIG-I was amplified by PCR and cloned into the XhoI and MluI sites of the baculoviral expression vector pFastBac (Invitrogen). For the expression of a MAVS protein fragment containing residues 131-291, the cDNA encoding this fragment was inserted into the NdeI and BamHI sites of pET14b (Novagen). The reporter gene IFNβ-Luc was constructed by subcloning 110 base pairs of the interferon-β promoter into a luciferase expression vector. All constructs were verified by automated DNA sequencing. Plasmids for p-KB$_3$-TK-Luc and pCMV-LacZ have been described previously (Deng et al., 2000). Plasmids for Gal4-Luc, Gal4-IRF3, Flag-TRIF, Flag-TBK1 and Flag-IKKε were provided by Dr. Kate Fitzgerald (University of Massachusetts at Worcester) and Dr. Tom Maniatis (Harvard). The IRF7 and IFN-α4-Luc plasmids were from Dr. John Hiscott (McGill University), and pcDNA3-myc-RIP2 was from Dr. Gabriel Nunez (University of Michigan). The MEF cell lines deficient in TRAF6, RIP1 and TBK1 were provided by Drs. Jun-Ichiro Inoue (University of Tokyo), Michelle Kelliher (University of Massachusetts at Worcester) and Wen-Chen Yeh (University of Toronto), respectively.

Antibodies and Proteins. The antibodies against RIG-I and MAVS were generated by immunizing rabbits with the recombinant proteins His$_6$-RIG-I (1-242) produced in Sf9 cells, and His$_6$-MAVS (131-291) produced in E. coli, respectively. Both antibodies were affinity purified using the respective RIG-I and MAVS antigen column. Rabbit polyclonal antibody against IRF3 (SC-9082) and NEMO (SC-8330) were purchased from Santa Cruz Biotechnology. Monoclonal antibody against IKKβ (BD Bioscience), FLAG (M2; Sigma), HA.11 (Covance), Calnexin (Stressgen), phospho-JNK and PARP (Cell Signaling) were purchased from the indicated suppliers.

RNAi. siRNA oligos at a final concentration of 20 nM were transfected into HEK293 cells using the calcium phosphate precipitation method. This transfection procedure was repeated on the second day to increase RNAi efficiency. On the third day, cells were transfected with indicated expression plasmids using Lipofectamine 2000 reagent (Invitrogen), and harvested 24 hours later. The sequences of the siRNA oligos are as follows (only the sense strands are shown): GFP (471-489):GCAGAAGAACGGCAUCAAG (SEQ ID NO.: 3); RIG-I (2363-2381): AAUUCAUCAGAGAUAGUCA (SEQ ID NO.: 4); MAVSa (899-917): CCACCUUGAUGCCUGUGAA (SEQ ID NO.: 5); MAVSb (1364-1382): CAGAGGAGAAUGAGUAUAA (SEQ ID NO.: 6). These RNA oligos were synthesized at the UT. Southwestern Center for Biomedical Invention (CBI) facility.

Confocal Imaging. HeLa cells were transfected with Polyfect reagent (Qiagen). 24 hours later cells were trypsinized and plated onto cover slips in 24-well plates. After allowing the cells to adhere for 12-18 hours, cells were incubated with 250 nM Mito Tracker Red (Molecular Probes) for 30 minutes at 37° C. Cells on the cover slips were then washed once with PBS and fixed in 3.7% formaldehyde in PBS for 15 minutes. Cells were permeabilized and blocked for 30 minutes at room temperature in a staining buffer containing Triton-X100 (0.2%) and BSA (3%), and then incubated with a primary antibody in the staining buffer lacking Triton-X100 for 1 hour. After washing three times in the staining buffer lacking Triton-X100, cells were incubated in secondary antibody for 1 hour. The cover slips, which were washed extensively, were dipped once in water and mounted onto slides using mounting media (VectaShield; Vector Laboratories). Imaging of the cells was carried out using Zeiss LSM510 META laser scanning confocal microscopy.

Cell culture, transfection, luciferase assay and ELISA. Human embryonic kidney (HEK) 293 cells and HeLa cells were cultured in DMEM supplemented with 10% calf serum and antibiotics. Transient transfection was carried out using the calcium phosphate precipitation method. For luciferase reporter assays, cells were seeded in 12-well plates at a cell density of $2 \times 10^5$ cells per well. On the second day, cells were co-transfected with 20 ng of a luciferase reporter gene, 20 ng of pCMV-LacZ as an internal control for transfection efficiency and the indicated expression vectors. For the IRF-3 activation assay, 40 ng of Gal4-IRF3 and 40 ng of Gal4-Luc constructs were co-transfected. Each study was carried out in duplicates. Cells were harvested 36 hours after transfection and lysed in the passive lysis buffer (Promega). Luciferase activity was measured with a luminometer (Rosys Anthos Lucy2) using luciferin as a substrate, and β-galactosidase activity was measured with a Thermo Labsystems microplate reader at the wavelength of 405 nm using o-nitrophenyl-β-D-galactopyranoside (ONPG) as a substrate. For the IFN-α4 luciferase reporter assay in MEF cells, $1 \times 10^5$ of wild type or mutant MEF cells were seeded in a 12-well plate. On the following day, pcDNA3-FLAG-MAVS (100 ng) or control vector was co-transfected with pcDNA3-FLAG-IRF-7 (50 ng), IFNα4-luc reporter (300 ng) and CMV-Renilla (100 ng) using lipofectamine 2000 (Invitrogen). 48 hours after transfection, cells were harvested to measure the expression of luciferase using the dual luciferase assay kit (Promega). IFN-β production by HEK 293 and MEF cells was measured using human and mouse IFN-β ELISA kits (PBL Biomedical Laboratories), respectively, following the manufacturer's instructions. Briefly, culture supernatant were collected and cleared by centrifugation, and 100 μl of supernatant from each sample was used for ELISA.

Viral infection and plaque assay. Sendai virus infection: Cells were infected with Sendai virus (Cantell strain; Charles River laboratories) for 20 hours at 50 hemagglutinating (HA) units/ml culture media. Briefly, cells in 12-well plates were washed once with 1× PBS and incubated with 0.5 ml of Sendai virus diluted in serum free DMEM. One hour later, an equal volume of DMEM supplemented with 20% calf serum and antibiotics was added to the cells. Cells were returned to the 37° C. incubator to continue culture for 19 hours.

VSV infection and plaque assay: For overexpression of MAVS, HEK293 cells in.12-well plates were transfected with 0.5 μg of pCDNA3-Flag-MAVS or empty vector. To silence the expression of MAVS, HEK293 cells were transfected with 20 nM of MAVS or GFP (control) siRNA oligos. These cells were infected with VSV (kindly provided by Dr. Michael Gale, UT Southwestern) at 0.001, 0.01, and 0.1 MOI for 24 hours. Cells were rinsed with PBS, fixed in 2% formaldehyde in PBS, and stained with 0.1% Amido Black in 10% acetic acid. For plaque assay, aliquots of culture media taken at 6, 12, 18, and 24 hours were used to infect HEK293 cells. Briefly, 293 cells in 6-well plates were infected with serial dilutions of the recovered viruses for 1 hour. Cells were overlaid with 0.5% soft agar in DMEM and incubated for 24 hours. Plates were stained with 0.01% neutral red in DMEM for 4 hours to display plaques, which were then quantitated.

RT-PCR. Total RNA was isolated from HEK293 cells using Trizol reagent (Gibco-BRL) and subjected to reverse-transcription polymerase chain reaction (RT-PCR) analysis to measure expression of IFN-β, RANTES, and GAPDH (as a control). Gene-specific primer sequences were as follows: IFNβ: CACGACAGCTCTTTCCATGA (SEQ ID NO.: 7) (forward); AGCCAGTGCTCGATGAATCT (SEQ ID NO.: 8) (reverse); RANTES: ATGAAGGTCTCCGCG-GCACGCCT (SEQ ID NO.: 9) (forward); CTAGCT-CATCTCCAAAGAGTTG (SEQ ID NO.: 10) (reverse); GAPDH: AAAATCAAGTGGGGCGATGCT (SEQ ID NO.: 11) (forward); GGGCAGAGATGATGACCCTTT (SEQ ID NO.: 12) (reverse). Reverse transcriptase (RT) reaction was performed with 2 μg RNA, 50 pmol random primer (9-mer), and 25 units of StrataScript Reverse Transcriptase (Stratagene) at 42° C. for 1 hour followed by PCR.

Protein extraction, Immunoprecipitation, JNK and IKK Kinase Assay. Cells were lysed in Buffer A (20 mM Tris-HCl, pH 7.5, 150 mM NaCl, 1.5 mM $MgCl_2$, 20 mM β-glycerophosphate, 1 mM sodium orthovanadate, 10% Glycerol, 0.5mM EGTA, 0.2% NP40, 1 mM PMSF, 1 mM DTT and 10 μg/μl leupeptin). After incubation on ice for 10 minutes, soluble extract was collected after centrifugation at 20,000×g for 15 minutes at 4° C. 20 μg of lysate was boiled in 2× SDS sample buffer followed by SDS-PAGE. Native gel electrophoresis and IRF3 dimerization assays were carried out as described previously (Iwamura et al., 2001). Immunoblotting was carried out by standard procedures and immuno-reactive proteins were visualized by colorimetric detection of an alkaline phosphatase substrate.

For detection of MAVS in different cell lines, cells were lysed in RIPA buffer (50 mM Tris-HCl, pH 8.0, 150 mM sodium chloride, 1% Triton X-100, 0.1% SDS and 0.5% sodium deoxycholate). Lysates were cleared by centrifugation at 14,000 rpm for 15 minutes and then resolved by SDS-PAGE and immunoblotted with a MAVS antibody.

To measure the activation of JNK by MAVS in vivo, pCMV-HA-JNK1 (1 μg) was transfected into HEK293 cells along with 1 μg of pEF-HA-MAVS, pcDNA3-myc-RIP2, or control vector using calcium phosphate transfection method. 24 hours after transfection, the cells were lysed in Buffer B (20 mM Tris-HCl, pH 7.5, 150 mM NaCl, 10% glycerol, 1% Triton X-100, 1 mM DTT, 1 mM PMSF and 10 μg/μl leupeptin). After centrifugation at 20,000×g for 10 min at 4° C., cleared lysates were resolved by SDS-PAGE and immunoblotted with an antibody specific for phosphorylated JNK.

For IKK kinase assay, cells were lysed in Buffer B, and the lysates cleared at 20,000×g for 15 minutes at 4° C. 500 μg of lysate was incubated with anti-NEMO antibody at 4° C. for immunoprecipitation. After 1 hour, 10 μl of protein A/G bead slurry was added. Immunoprecipitation was carried out for another hour. The beads were washed twice with Buffer B and then three times with Buffer C (20 mM HEPES, pH 7.6, 50 mM NaCl, 20 mM β-glycerophosphate, 1 mM sodium orthovanadate, 10 mM $MgCl_2$ and 1 mM DTT). The beads containing the immunoprecipitated IKK complex were incubated in 20 μl of the kinase reaction buffer (Buffer C) containing GST-IκBα-NT (100 μg/ml; N-terminal 36 residues of IκBα), ATP (100 μM) and $\gamma$-$^{32}$P-ATP (5 μCi) for 30 minutes. After SDS-PAGE, the phosphorylation of IκBα was analyzed by PhosphorImaging.

Subcellular Fractionation. HEK293 cells were washed with cold PBS and lysed by douncing for 20 times in Homogenization buffer (Buffer D: 10 mM Tris-HCl, pH7.5, 2 mM MgCl2, 10 mM KCl, 250 mM Sucrose, Protease Inhibitor cocktail, 0.5 mM DTT). The homogenate was centrifuged at 500×g for 5 minutes, and the pellet (P1) was saved as crude nuclei. The supernatant (S1) was centrifuged at 5,000×g for 10 minutes to precipitate crude mitochondria (P5). The supernatant (S5) was further centrifuged at 15,000×g for 10 minutes to generate S15 and P15. Each pellet was resuspended in Buffer D for later studies. To further purify mitochondria, P5 was homogenized gently in Buffer D, and 800 μl of the resuspension was laid on top of a continuous sucrose gradient from 0.3-1.8M in 10 ml. After centrifugation at 100,000×g for 90 minutes in a Beckman 41Ti ultracentrifuge, 800 μl fractions were collected from the top. In some studies (to demonstrate the membrane localization of MAVS), the mitochondrial fraction (P5) was sonicated before it was subjected to ultracentrifugation.

EXAMPLE 2

The Specific and Essential Role of MAVS in Antiviral Innate Immune Responses. The mitochondrial antiviral signaling protein (MAVS) mediates the activation of NF-κB and IRFs and the induction of interferons in response to viral infection. In vitro studies have also suggested that MAVS is required for interferon induction by cytosolic DNA, but the in vivo evidence is lacking. By generating MAVS-deficient mice, it is shown herein that loss of MAVS abolished viral induction of interferons and prevented the activation of NF-κB and IRF3 in multiple cell types, except plasmacytoid dendritic cells. However, MAVS was not required for interferon induction by cytosolic DNA or by Listeria monocytogenes. Mice lacking MAVS were viable and fertile, but they failed to induce interferons in response to poly(I:C) stimulation and were severely compromised in immune defense against viral infection. These results provide the in vivo evidence that the cytosolic viral signaling pathway through MAVS is specifically required for innate immune responses against viral infection.

Innate immunity is the first line of defense against microbial pathogens, including viruses. Viral infection triggers the induction of type-I interferons (e.g., IFN-α and IFN-β) and other proinflammatory cytokines through two distinct signaling pathways (Honda et al., 2005; Kawai and Akira, 2006; McWhirter et al., 2005; Seth et al., 2006). One of these pathways utilizes a subfamily of Toll-like receptors (TLR3, 7, 8, and 9) to detect viral nucleic acids in the endosome following the endocytosis of viral particles. These TLRs are localized in the endosomal membranes of specialized cell types, such as plasmacytoid dendritic cells (pDC; reviewed by Liu, 2001), and they recruit the adaptor protein MyD88 or TRIF to activate protein kinases including IκB kinase complex (consisting of IKKα, IKKβ and NEMO/IKKγ) and the IKK-related kinases (TBK1 and IKKε). The IKK complex phosphorylates the NF-κB inhibitor IκB, and targets IκB for degradation by the ubiquitin-proteasome pathway, thereby allowing NF-κB to enter the nucleus to induce a large array of genes involved in immune and inflammatory responses (Silverman and Maniatis, 2001). TBK1 and IKKε phosphorylate another transcription factor IRF3 or IRF7, resulting in its dimerization and nuclear translocation (Fitzgerald et al., 2003; Sharma et al., 2003). The nuclear IRFs, NF-κB and other transcription factors form an enhanceosome complex to activate the expression of interferons (Maniatis et al., 1998), which are then secreted to bind to their receptors on viral-infected as well as neighboring non-infected cells. The engagement of the interferon receptors activates the JAK- STAT signaling pathway to induce interferon-stimulated genes (ISGs), which suppress viral replication and assembly (Darnell et al., 1994).

The other viral signaling pathway utilizes the retinoic acid inducible gene I (RIG-I) to detect viral double-stranded RNA (dsRNA) in the cytosol (Yoneyama et al., 2004). RIG-I binds to viral dsRNA through its C-terminal RNA helicase domain, and mediates the activation of IKK and TBK1/IKKε through its N-terminal caspase activation and recruitment domains (CARD). For unknown reasons, RIG-I knockout mice are embryonic lethal, suggesting that RIG-I has unexpected functions related to animal development (Kato et al., 2005). Although the inability to obtain viable RIG-I knockout mice precludes the study of the role of RIG-I in vivo, studies using cells derived from these mice show that RIG-I is essential for innate immune responses to several RNA viruses in different cell types. However, in plasmacytoid dendritic cells, loss of RIG-I had no effect on viral induction of interferons, whereas TLR7 and MyD88 are required for the immune response in these cells (Diebold et al., 2004; Heil et al., 2004; Kato et al., 2005; Lund et al., 2004).

The adaptor protein that links RIG-I to IKK and TBK1/IKKε activation is the recently identified mitochondrial antiviral signaling protein [MAVS (Seth et al., 2005), also known as IPS-1 (Kawai et al., 2005), VISA (Xu et al., 2005) or CARDIF (Meylan et al., 2005)]. MAVS contains an N-terminal CARD domain that interacts with the tandem CARD domains of RIG-I, and a C-terminal transmembrane domain that localizes it to the mitochondrial outer membrane (Seth et al., 2005). The mitochondrial localization of MAVS is essential for its signaling function, and this property is exploited by hepatitis C virus, which deploys the NS3/4A serine protease to cleave MAVS off the mitochondria to evade the host innate immune responses (Freundt and Lenardo, 2005; Li et al., 2005; Meylan et al., 2005). Recent studies have shown that cytosolic B-form DNA and the bacterium *Listeria* monocytogenes can also induce interferons (Ishii et al., 2006; Okabe et al., 2005; Perry et al., 2005; Stetson and Medzhitov, 2006). Cell culture studies have suggested that MAVS/IPS-1 is required for interferon induction by cytosolic DNA (Ishii et al., 2006); however, the in vivo evidence is lacking.

MAVS-deficient cells were used to demonstrate that MAVS is essential for viral induction of interferons and activation of NF-κB and IRF3 in multiple cell types, including fibroblasts, macrophages and conventional dendritic cells. However, in plasmacytoid dendritic cells, MAVS is not required for viral induction of interferons and cytokines. Contrary to previous reports, the inventors found that loss of MAVS did not affect interferon induction by cytosolic DNA or *Listeria* monocytogenes. Furthermore, it was found that MAVS-deficient mice failed to induce interferons in response to poly(I:C) stimulation. Interestingly, the MAVS-deficient mice produced normal amounts of interferons in the sera when they were infected with vesicular stomatitis virus (VSV), but they were nevertheless more susceptible to viral-induced killing. Taken together, these results demonstrate the specific and essential role of MAVS in antiviral innate immunity.

Figure 14E:
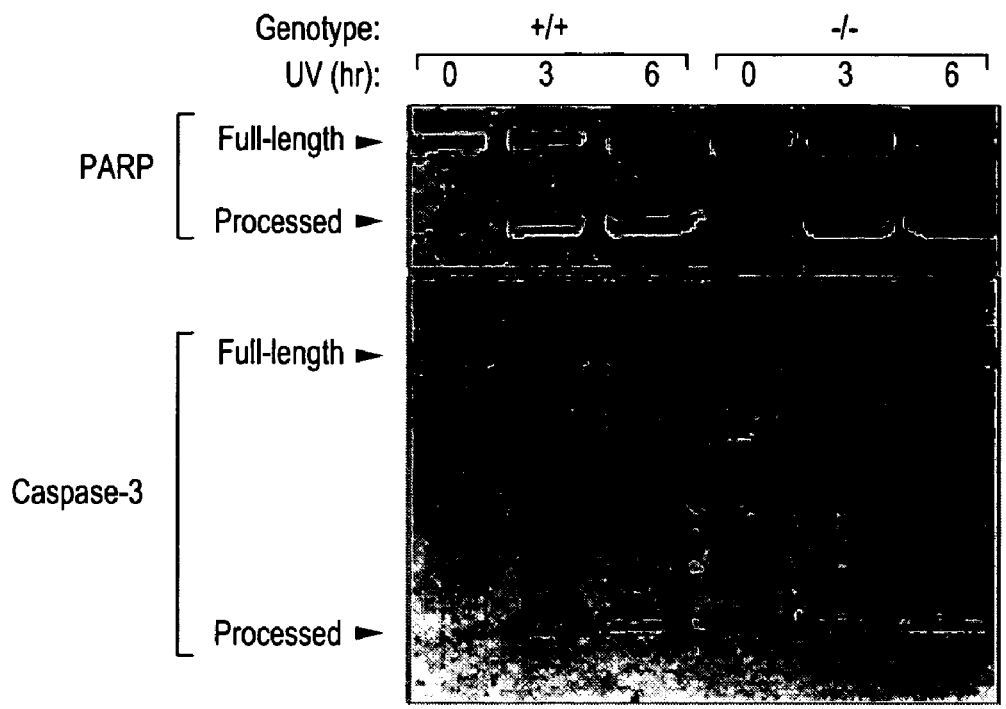
FIG. 14. Generation of Mavs$^{-/-}$ mice. (A) Targeting strategy for deleting exon 2 from the ATG start codon to exon 3 of the Mavs locus by homologous recombination. DTA: diphtheria toxin A. (B) Southern blotting analysis of BamH1-digested genomic DNA from the mouse tails using the 5'-probe as indicated in (A). (C) Immunoblot analysis of protein extracts from MEF cells of different genotypes using an antibody against mouse MAVS. N.S: non-specific. (D) Offspring from the breeding of Mavs$^{+/-}$ mice. (E) MAVS is not involved in UV-induced apoptosis. (E) Wild type and Mavs–/– MEF cells were irradiated with UV (100 mj/cm2) and then incubated for the indicated time periods. Cell lysates were immunoblotted with an antibody against PARP (upper panel) or caspase-3 (lower panel). (F) Similar to (E), except that UV irradiation was carried out at various doses as indicated and then cells were cultured for 16 hours before harvest.
Figure 14F:
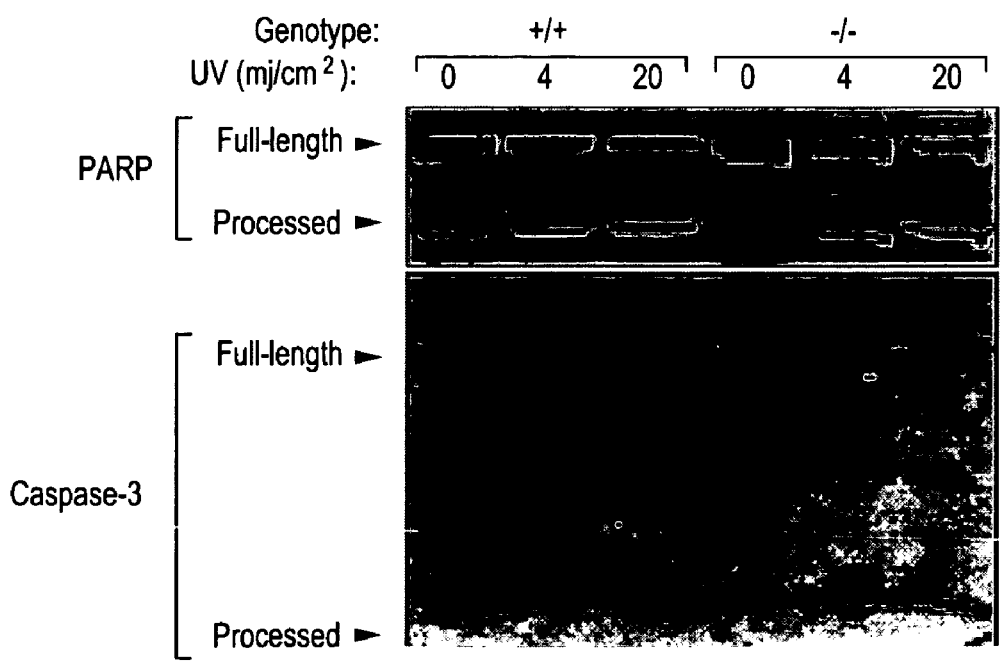

Generation of Mavs$^{-/-}$ Mice. To elucidate the role of MAVS in vivo Mavs-deficient (Mavs$^{-/-}$) mice were generated by homologous recombination in ES cells (FIG. 14A). The deletion of Mavs was verified by Southern and Western blotting (FIGS. 14B & 14C). The mutant mice were born at the Mendelian ratio (FIG. 14D), and they developed and bred normally. These mice displayed no apparent abnormality at the ages of up to 8 months. The inventors have previously shown that MAVS is localized in the mitochondrial outer membrane and that it contains a C-terminal transmembrane domain resembling those of anti-apoptotic mitochondrial proteins such as Bcl-2 and Bcl-xL (Seth et al., 2005). To examine the potential role of MAVS in apoptosis, embryonic fibroblasts (MEF) from the wild type and mutant mice and irradiated these cells with UV were isolated (FIG. 14E). Immunoblotting studies showed that there was no apparent difference in the UV-induced cleavage of poly (ADP-ribose) polymerase (PARP) or caspase-3 between the wild type and Mavs$^{-/-}$ cells. Thus, MAVS is not essential for mouse development or survival.

Figure 15A:
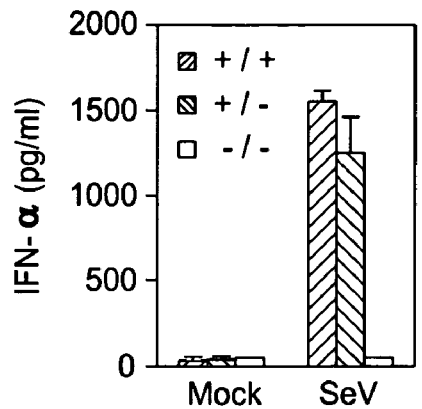
FIG. 15. MAVS is required for antiviral innate immune responses in MEF cells. (A, B & C) MEF cells were incubated with Sendai virus (SeV), LPS or poly(I:C) for 16 hours, and the culture supernatants were harvested for ELISA analyses to measure the production of IFN-α, IFN-β and IL-6 as indicated. (D) MEF cells were infected with Sendai virus for the indicated times, and then cell lysates were separated on 9% polyacrylamide gels under non-denaturing conditions. The IRF3 dimer and monomer were detected by immunoblotting. hpi: hours post infection. (E & F) Electrophoretic mobility shift assays (EMSA) for NF-κB DNA binding using whole cell extracts from MEF cells infected with Sendai virus or stimulated with LPS for the indicated times. *: non-specific. (G) MEF cells were transfected with poly(I:C) for the indicated times and then cell extracts were prepared for analyses of IRF3 dimerization by native gel electrophoresis. (H) MEF cells were incubated with VSV-GFP at the indicated multiplicity of infection (MOI) for 24 hours, and infection of cells was visualized by fluorescent microscopy. Nomarski microscopy showed that less Mavs$^{-/-}$ cells were detected following VSV-GFP infection, an indication that these cells were more susceptible to viral killing. MEF cells were transfected with 10 µg/ml of poly(dl:dC), poly(dA:dT), and poly(I:C) with lipofectamine 2000 (LF2000). In studies without LF2000, the nucleic acids or Sendai virus were added to the culture media. 16 hours later, culture media were harvested for ELISA to measure the concentrations of IFN-α (I), IFN-β (J) and IL-6 (K).
Figure 15B:
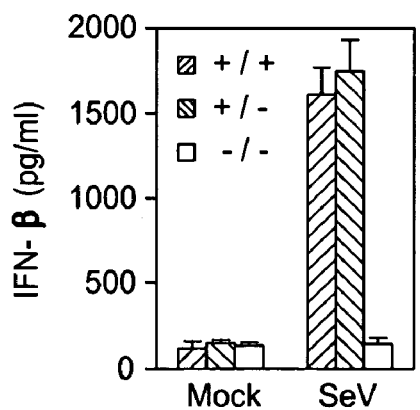
Figure 15C:
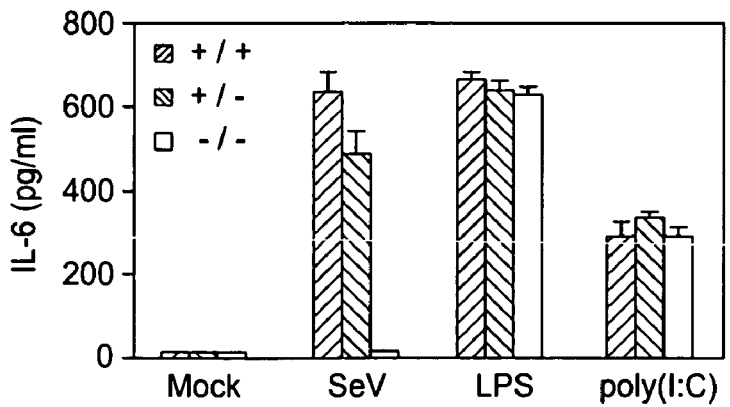
Figure 15D:
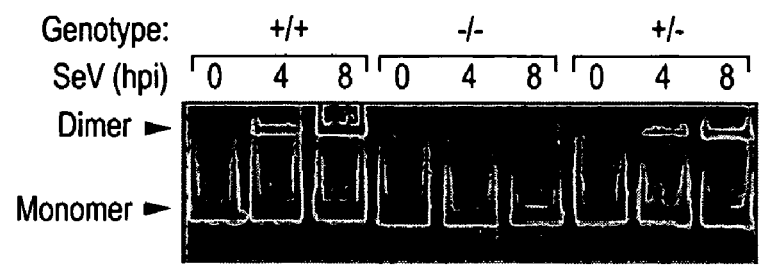
Figure 15E:
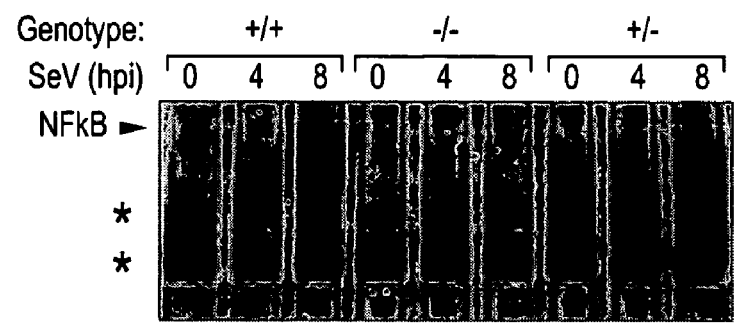
Figure 15F:
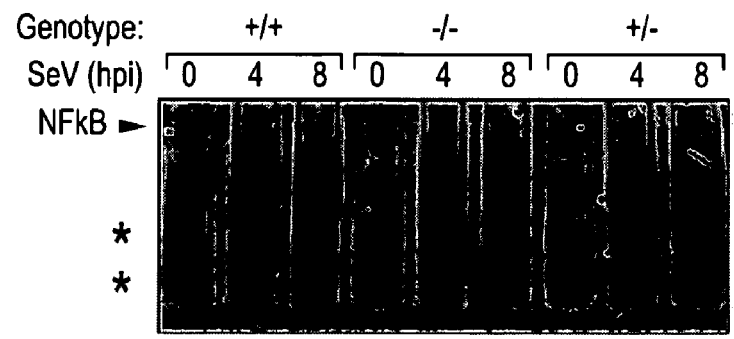
Figure 15G:
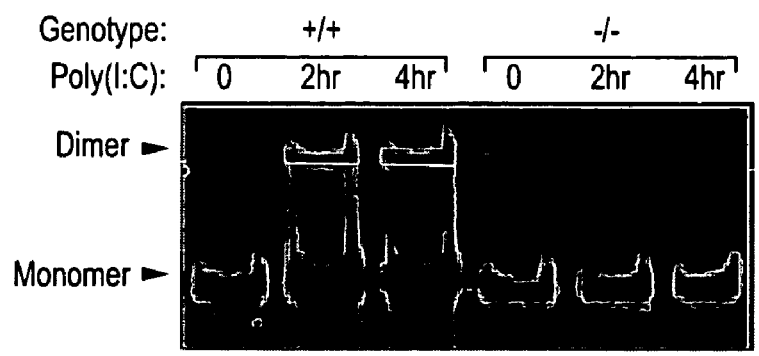
Figure 15H:
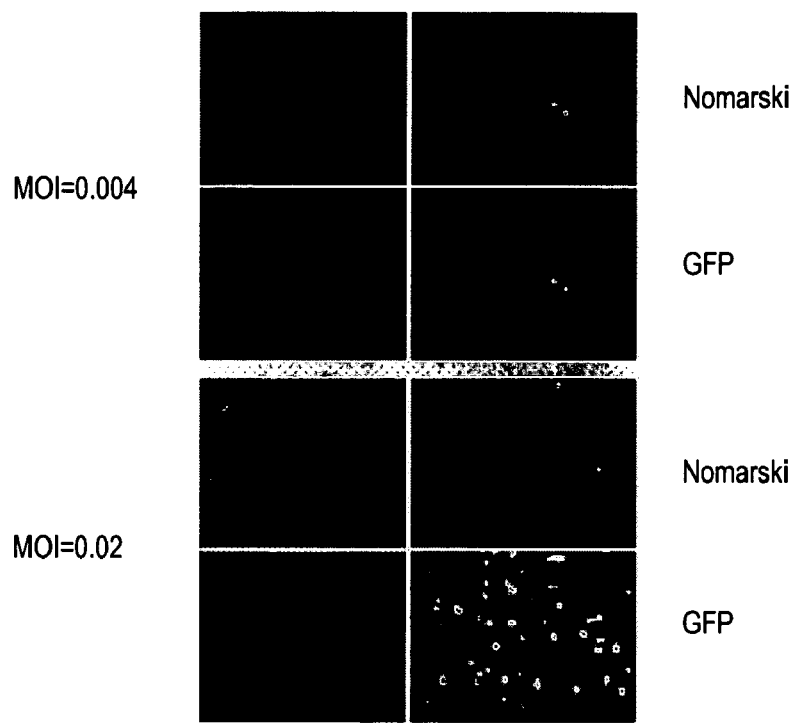
Figure 15I:
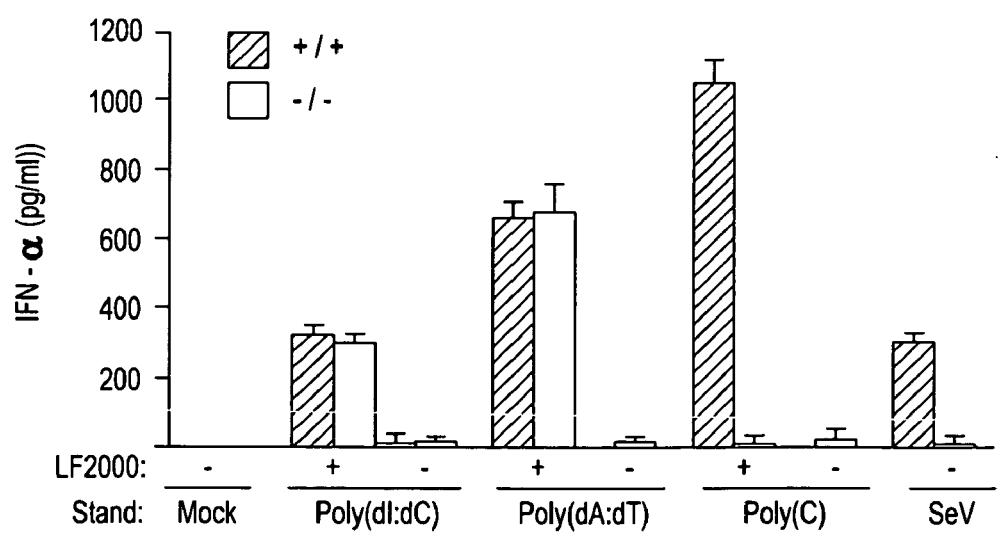
Figure 15J:
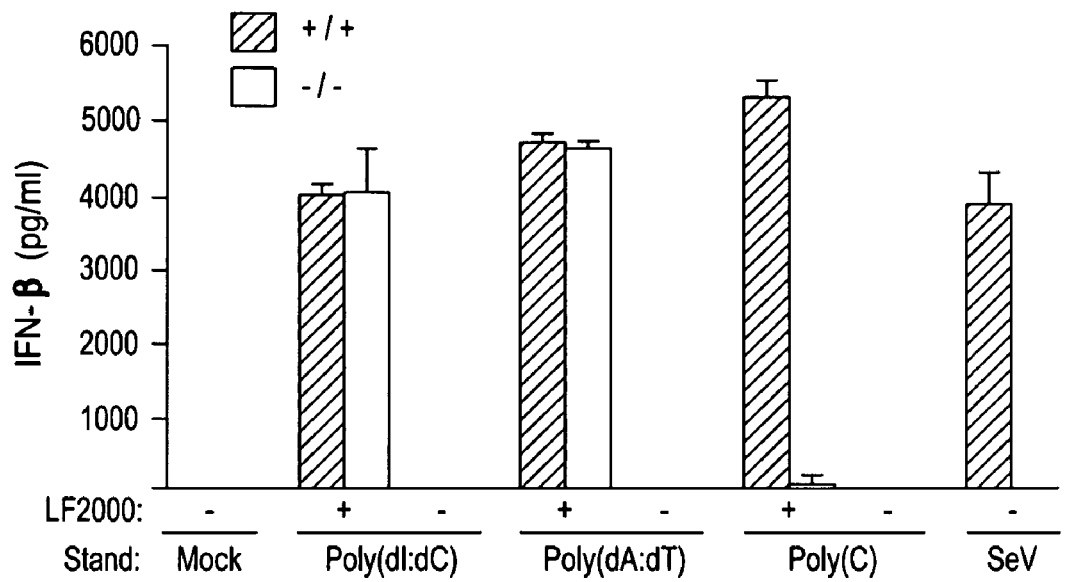
Figure 15K:
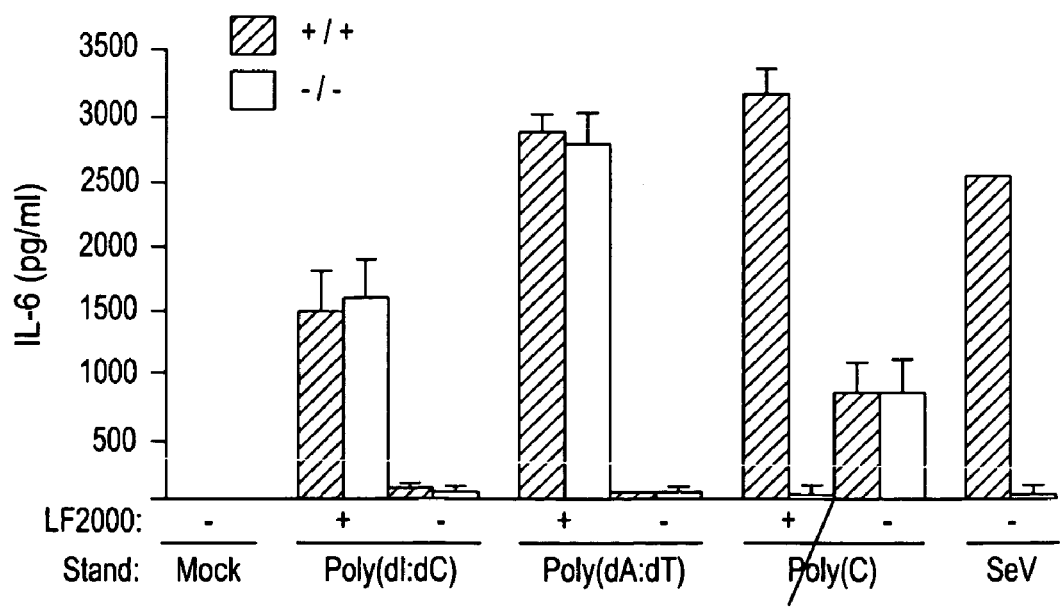

Mavs$^{-/-}$ Embryonic Fibroblasts are Defective in Antiviral Innate Immune Responses. To investigate the role of MAVS in antiviral immunity, MEF cells were infected from the wild type and mutant mice with Sendai virus (SeV), an RNA virus of the paramyxoviridae family, and then measured interferon production by ELISA. MEF cells from Mavs$^{-/-}$ mice were completely defective in the production of IFN-α and IFN-β following viral infection (FIGS. 15A & 15B). The induction of the proinflammatory cytokine IL-6 by Sendai virus was also abolished in Mavs$^{-/-}$ cells, but this response was unaffected when the cells were stimulated with lipopolysaccharides (LPS) or double-stranded RNA poly(I:C), which activates TLR4 or TLR3, respectively (FIG. 15C). The activation of IRF3 and NF-κB was also examined using gel shift assays, which measure the dimerization of IRF3 and DNA-binding of NF-κB on native gels, respectively. Viral infection led to the dimerization and nuclear translocation of IRF3 in the wild type and heterozygous cells, but not in Mavs$^{-/-}$ cells (FIG. 15D, and data not shown). Similarly, the loss of Mavs abolished NF-κB activation by Sendai virus (FIG. 15E), but not by LPS (FIG. 1SF). As most viruses produce double-stranded RNA that is detected by the host innate immune system, the role of MAVS in the cytosolic dsRNA signaling pathway was examined. As shown in FIG. 15G, transfection of poly(I:C) in MEF cells led to the dimerization of IRF3 in the wild type cells, but not in Mavs$^{-/-}$ cells. Furthermore, the induction of IFN-α, IFN-β, and IL-6 by poly(I:C) was abolished in Mavs$^{-/-}$ cells (FIG. 15I). In contrast to poly(I:C) transfection, which introduced the RNA into the cytosol, addition of poly (I:C) to the media, which is known to stimulate TLR3, did not induce IFN-α or IFN-β in MEF cells, but induced IL-6 through a MAVS-independent manner (FIG. 15I, and FIG. 15A-15C). Taken together, these results indicate that MAVS is required for signaling by Sendai virus and cytosolic dsRNA in general, but is not required for signaling by TLR3 and TLR4.

Figure 16A:
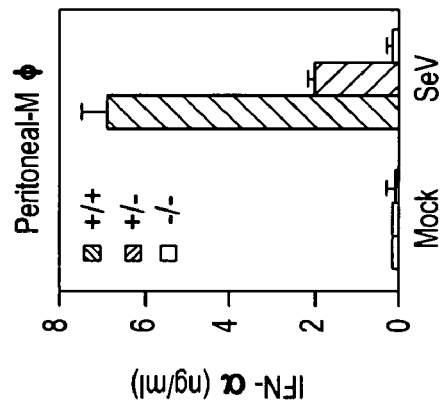
FIG. 16. MAVS is essential for antiviral innate immune responses in macrophages. (A-F) Bone marrow derived macrophages (BMDM) or peritoneal macrophages (MΦ) were incubated with Sendai virus (SeV), LPS, or poly(I:C) for 16 hours, and then cell extracts were collected for measurement of IFN-α, IFN-β or IL-6 by ELISA as indicated. *: not detectable. (G) Cell extracts from bone marrow derived macrophages (BMDM) infected with Sendai virus for the indicated times were resolved by native gel electrophoresis and then analyzed by immunoblotting with an IRF3-specific antibody. (H) Cell extracts as described in (G) were incubated with γ-$^{32}$P-ATP labeled NF-κB oligos and then resolved by native gel electrophoresis (EMSA). N.S: non-specific. Enhanced susceptibility to viral infection and killing in Mavs-deficient cells. Wild type and Mavs–/– MEF cells were infected with VSV-GFP at the indicated MOI for 20 hours, and then the cells were stained with Annexin V-APC and analyzed by FACS using two channels that detect GFP and Annexin V-APC simultaneously. The percentage of GFP-positive cells indicates viral infection (1), whereas the percentage of Annexin V positive cells is a measure of cell death (J).
Figure 16B:
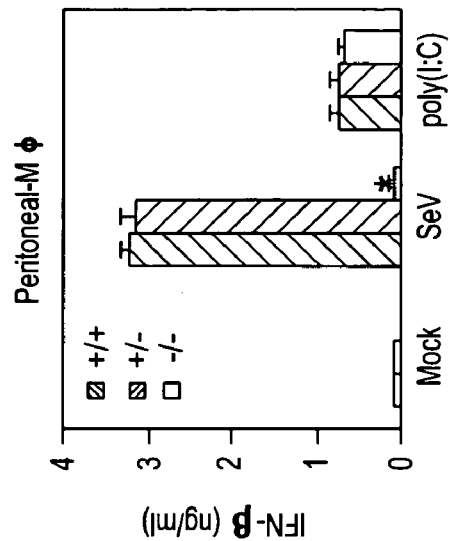
Figure 16C:
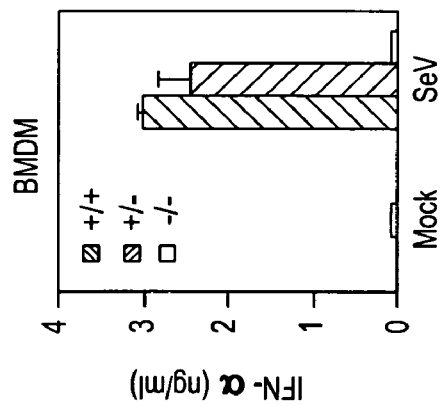
Figure 16D:
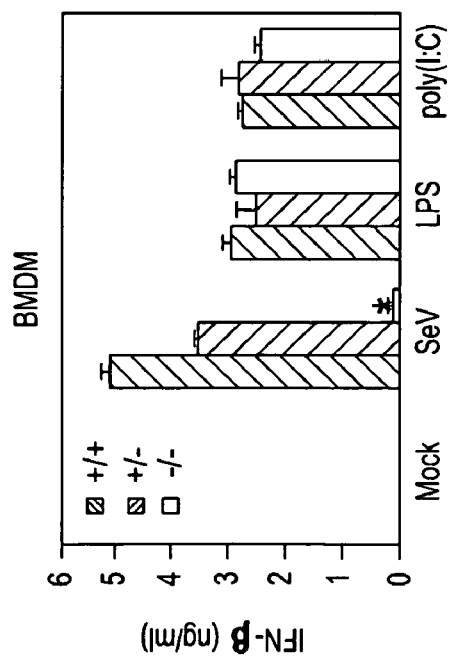
Figure 16E:
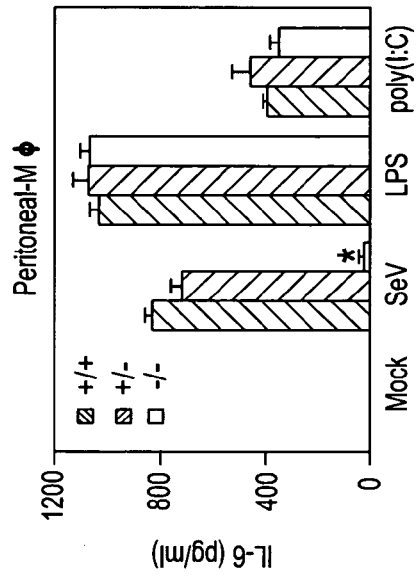
Figure 16F:
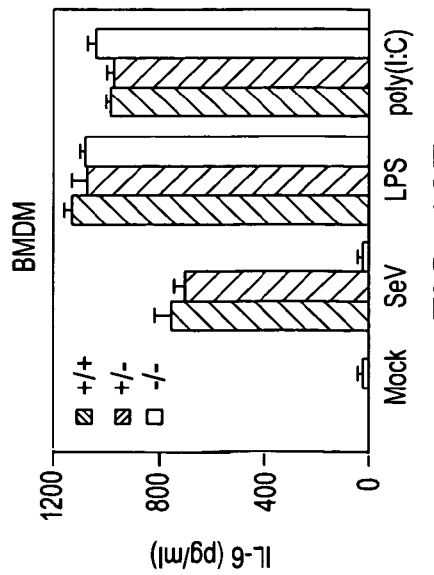
Figure 16G:
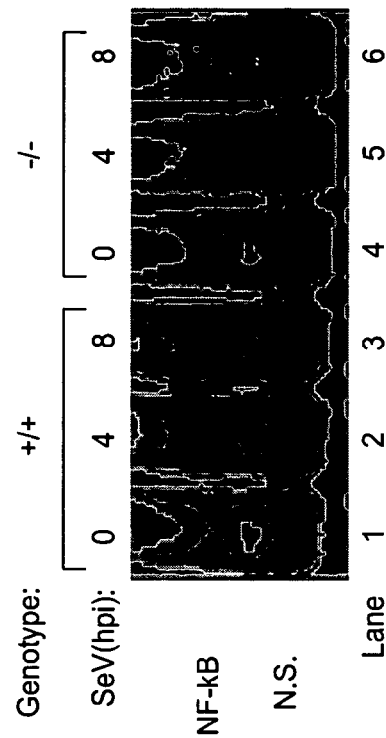
Figure 16H:
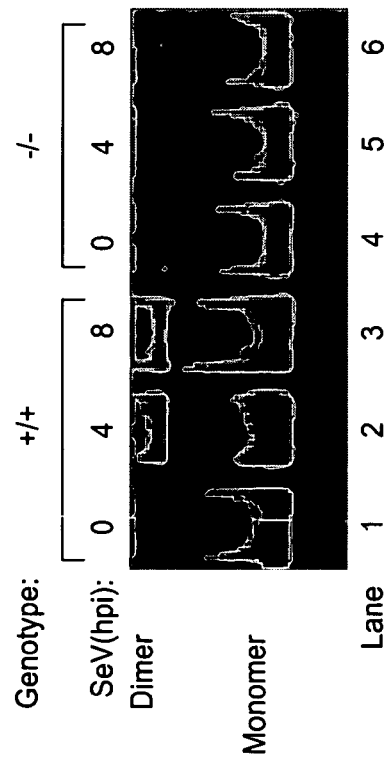
Figure 16I:
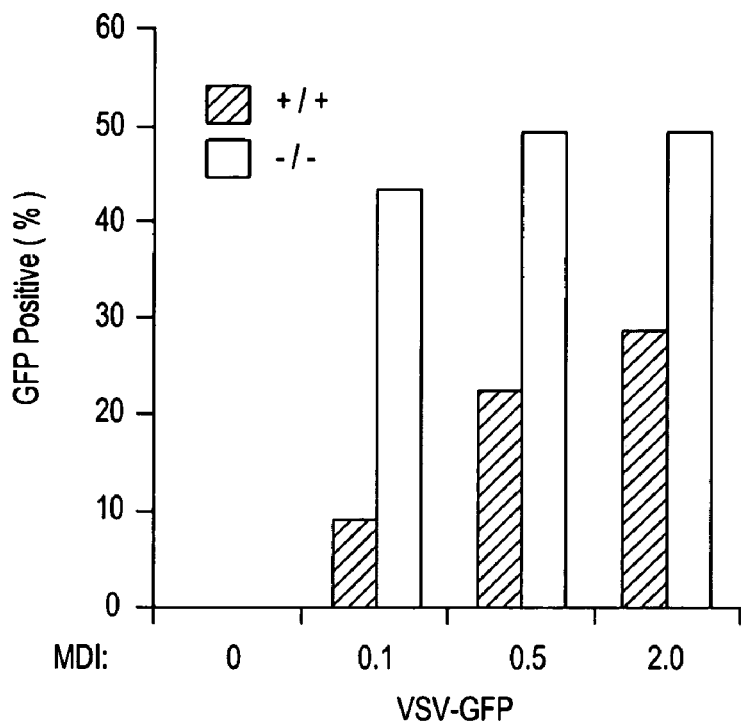
Figure 16J:
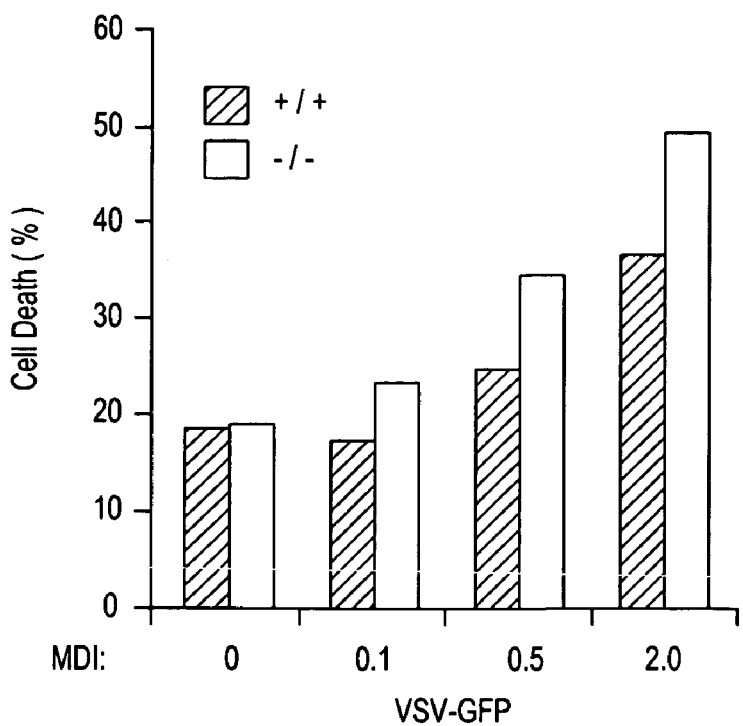

To examine the role of MAVS in viral replication and survival of host cells, MEF cells were infected with vesicular stomatitis virus (VSV), an RNA virus of the rhabdoviridae family. The VSV contains a GFP fused to the cytoplasmic domain of the envelope glycoprotein (G) of the virus, allowing direct visualization of viral replication (Dalton and Rose, 2001). As shown in FIG. 15H, Mavs$^{-/-}$ cells were much more permissible to viral replication (GFP fluorescence) and susceptible to viral killing (Normarski microscopy) as compared to wild type cells. To quantify viral infection and killing, fluorescent activated cell sorting (FACS) was used to measure the numbers of GFP positive cells as well as apoptotic cells that can be stained by Annexin V (FIG. 16I). After infection with VSV-GFP, the percentages of both GFP- and Annexin V-positive cells were significantly increased in Mavs$^{-/-}$ cells as compared to the wild type cells. Thus, MAVS is essential for immune defense against viral infection and killing.

MAVS is Required for Antiviral Innate Immune Responses in Macrophages. It was determined whether MAVS is required for interferon induction in macrophages. Bone marrow-derived macrophages (BMDM) and peritoneal macrophages were isolated and infected these cells with Sendai virus. The viral induction of IFN-α, IFN-β and IL-6 was completely abolished in Mavs$^{-/-}$ macrophages (FIG. 16A-F). Furthermore, Mavs$^{-/-}$ macrophages failed to activate IRF3 or NF-κB in response to Sendai virus (FIGS. 16G & 16H). In contrast, the induction of IFN-β and IL-6 by LPS or poly(I:C) was normal in Mavs$^{-/-}$ macrophages (FIG. 16C-16F). Therefore, MAVS is specifically required for antiviral responses in macrophages.

Figure 17A:
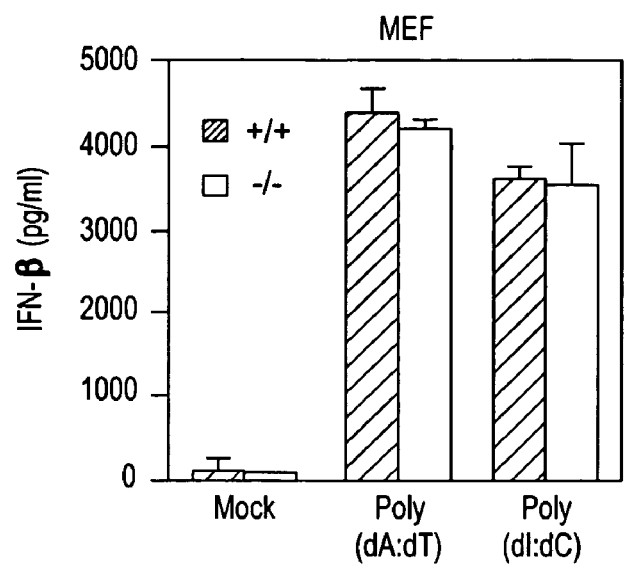
FIG. 17. MAVS is not required for interferon induction by cytosolic DNA or Listeria Monocytogenes (L.M.) (A) MEF cells were transfected with poly(dA:dT) or poly(dI:dC) for 16 hours, and then culture supernatants were harvested for measurement of IFN-β by ELISA. (B) MEF cells were transfected with 10 µg/ml of poly(dA:dT) DNA, and the cell lysates were resolved by native gel electrophoresis followed by immunoblotting with an IRF3 antibody (upper panel). The same cell lysates were also analyzed for NF-κB DNA binding by EMSA (bottom panel). N.S: non-specific (C) Similar to (B), except that poly(dI:dC) was used to stimulate cells. (D & E). Bone marrow derived macrophages (BMDM) were infected with Listeria Monocytogenes (L.M. ) for 16 hours, and the culture supernatants were harvested for measurement of IFN-β and IL-6 by ELISA. (F & G) MEF cells or peritoneal macrophages were infected with Listeria Monocytogenes (L.M.) for 16 hours, and the induction of IL-6 was measured by ELISA. (H) Cell lysates from MEF cells infected with Listeria Monocytogenes (L.M.) or Sendai virus (SeV) were resolved by native gel electrophoresis and then immunoblotted with an antibody against IRF3. Isolation of pDC, cDC and peritoneal macrophages. (I) Bone marrow cells were cultured in the presence of Flt-3L for 6 days and then sorted by FACS after staining with antibodies against CD11c and B220. Aliquots of the sorted cells (Postsort) were analyzed again by FACS to determine the purity of pDC and cDC. (J) Peritoneal macrophages isolated as described in the materials and methods were stained with an antibody against CD11b and then analyzed by FACS.
Figure 17B:
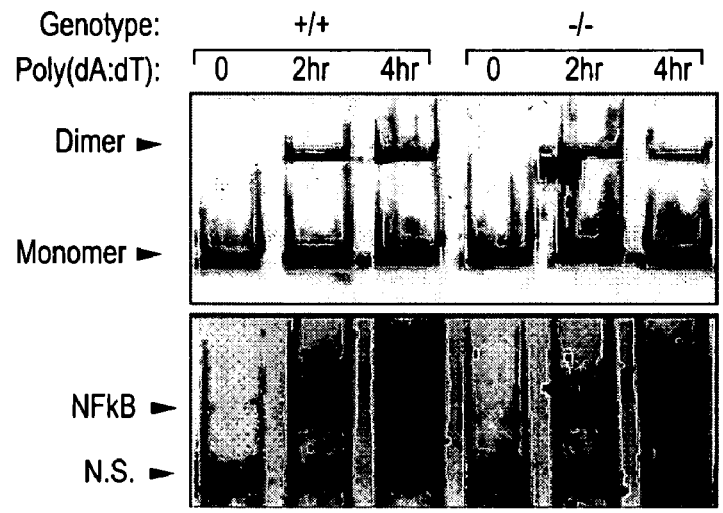
Figure 17C:
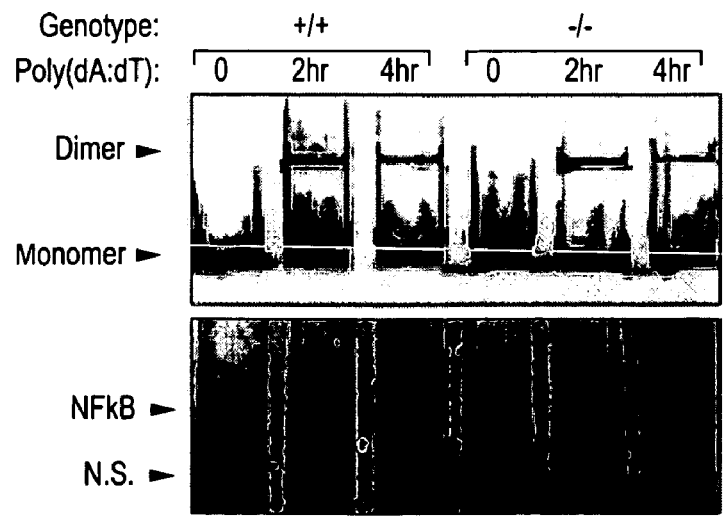

MAVS is not Required for Interferon Induction by Cytosolic DNA or *Listeria monocytogenes*. Recently, it was reported that cytosolic B-form DNA could elicit the induction of interferons (Ishii et al., 2006; Okabe et al., 2005; Stetson and Medzhitov, 2006), through a mechanism dependent on MAVS/IPS-1 (Ishii et al., 2006). To investigate whether MAVS is required for IFN induction by cytosolic DNA, MEF cells were transfected with double-stranded DNA poly(dA:dT) or poly(dI:dC). Both wild type and Mavs$^{-/-}$ cells had a robust induction of IFN-β following DNA transfection (FIG. 17A). Similarly, the induction of IFN-α and IL-6 by cytosolic DNA was intact in Mavs$^{-/-}$ cells (FIG. 15I). No cytokine induction was detected when the dsDNA was added to culture media directly without transfection, indicating that there were no contaminating TLR ligands in the DNA preparations. Native gel analyses showed that cytosolic DNA-induced activation of NF-κB and dimerization of IRF3 was not affected by Mavs deficiency (FIGS. 17B & 17C). Thus, MAVS is not required for the induction of interferons or the activation of NF-κB and IRF3 by cytosolic DNA.

Figure 17D:
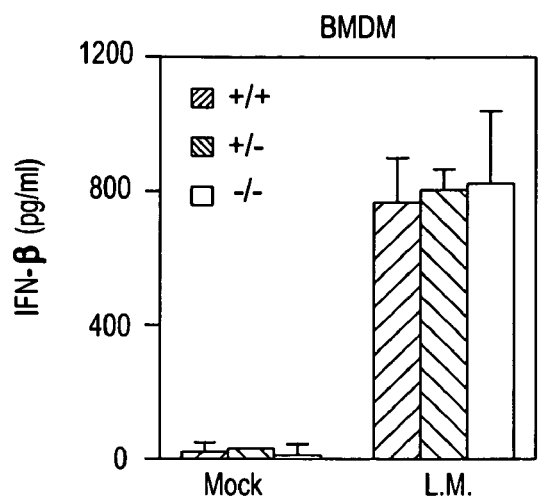
Figure 17E:
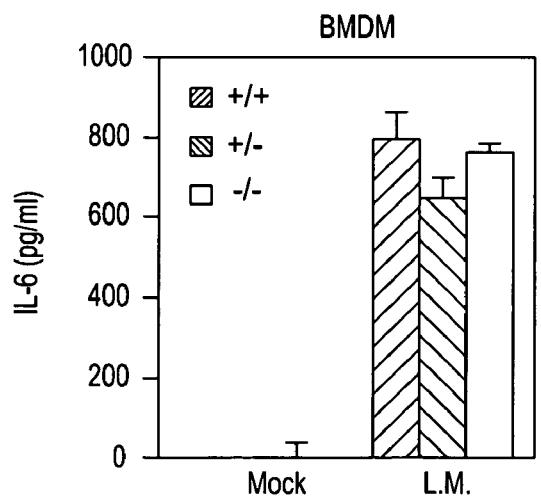
Figure 17F:
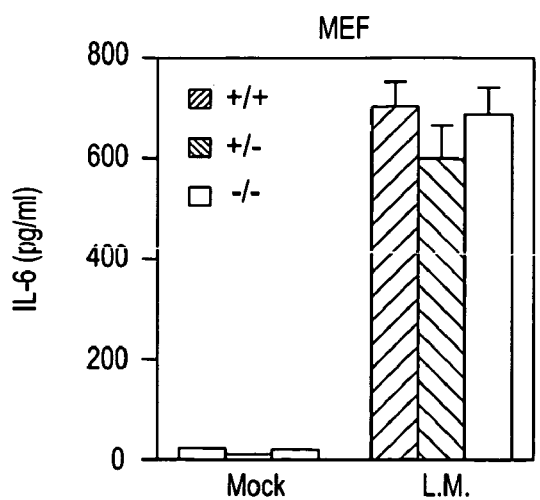
Figure 17G:
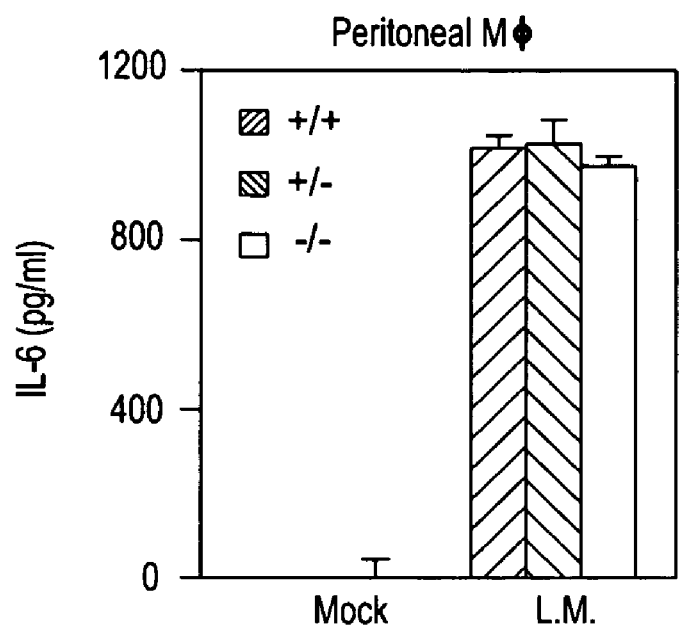
Figure 17H:
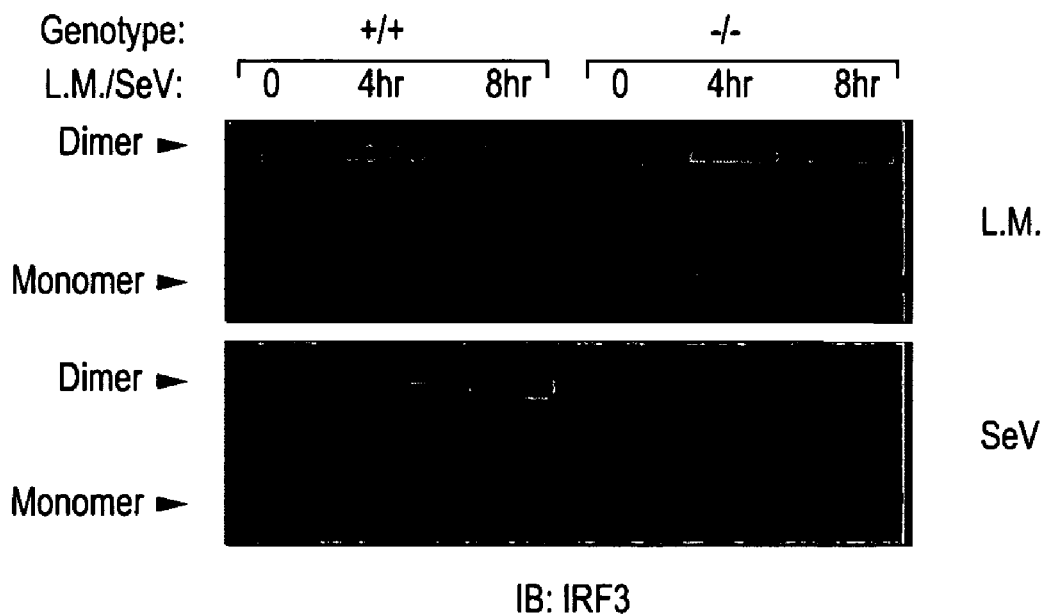

*Listeria monocytogenes* is an intracellular bacterium that can induce interferon production through a pathway that depends on TBK1 and IRF3 (O'Connell et al., 2005; Stockinger et al., 2004). Recent studies have shown that Listeria induces interferons by releasing bacterial DNA into the cytosol (Stetson and Medzhitov, 2006), but the signaling pathway that links Listeria infection to IRF3 activation is not understood. To determine if MAVS is involved in the induction of interferons by *Listeria*, BMDM were infected with *Listeria* and found that comparable amounts of IFN-β and IL-6 were produced in wild type and Mavs$^{-/-}$ macrophages (FIGS. 17D & 17E). The loss of MAVS also did not affect IL-6 induction by Listeria in MEF and peritoneal macrophages (FIGS. 17F & 17G), nor did it affect the dimerization of IRF3 (FIG. 17H). Taken together, these results indicate that MAVS is dispensable for interferon induction and IRF3 activation by Listeria, further reinforcing the conclusion that MAVS is not required for interferon induction by cytosolic DNA.

Figure 17I:
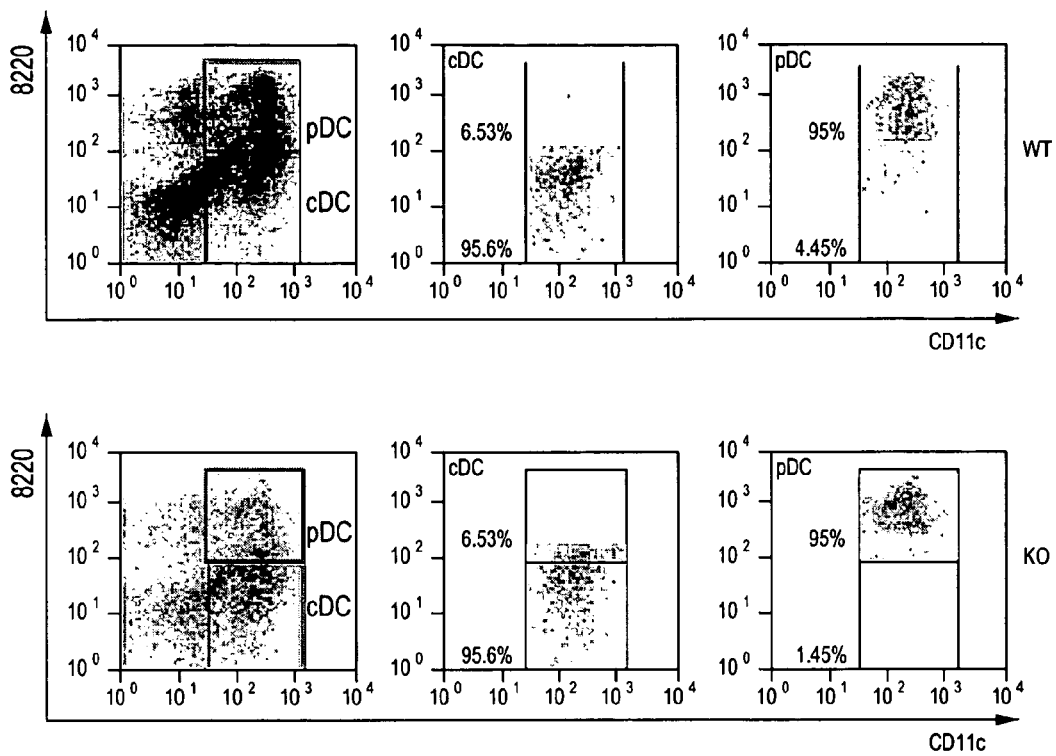
Figure 17J:
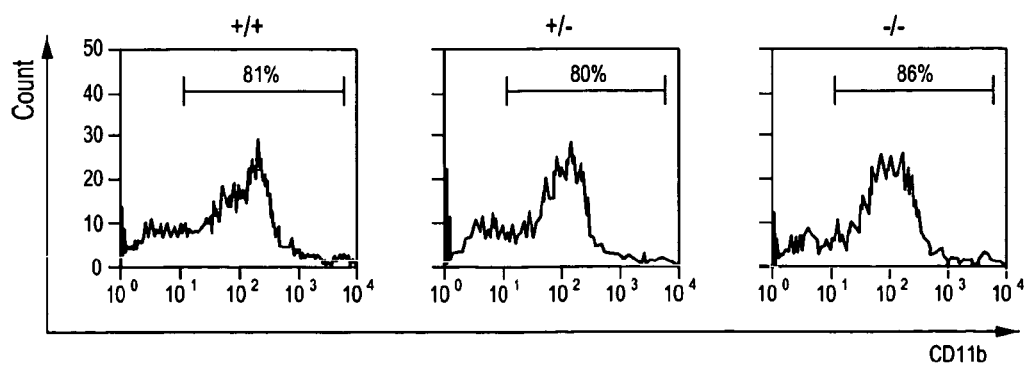
Figure 18A:
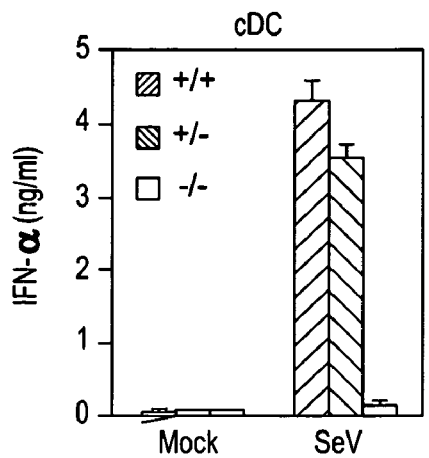
FIG. 18. MAVS is essential for interferon induction in conventional dendritic cells (cDC) but not plasmacytoid dendritic cells (pDC). (A-C). cDC were isolated from bone marrow cells following stimulation with GM-CSF. These cells were incubated with Sendai virus (A-C), LPS, poly(I:C) or CpG DNA (C), and the production of IFN-α, IFN-β and IL-6 was measured by ELISA. (D & E) pDC were isolated from Flt-3L-stimulated bone marrow cells and purified by FACS. These cells were stimulated with Sendai virus for 16 hours, and then culture supernatants were harvested for measurement of IFN-α and IFN-β by ELISA.
Figure 18B:
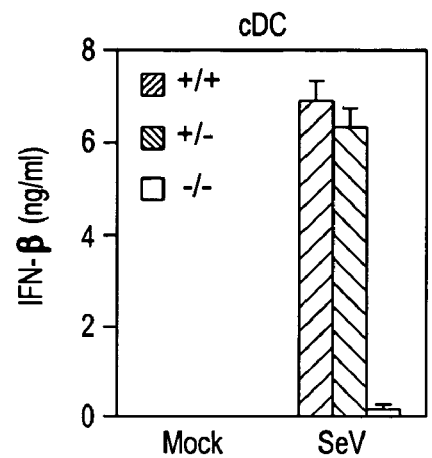
Figure 18C:
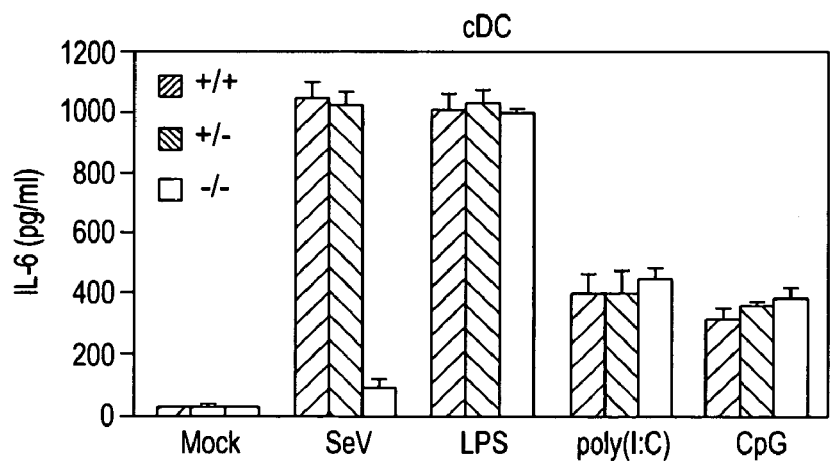
Figure 18D:
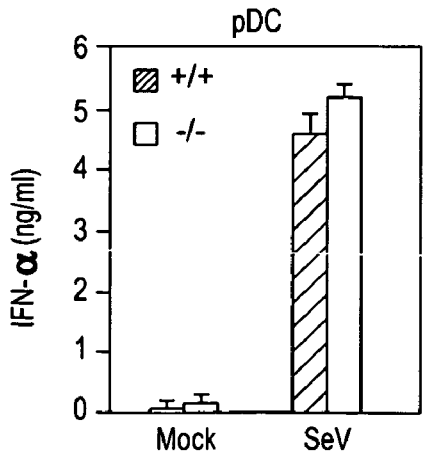
Figure 18E:
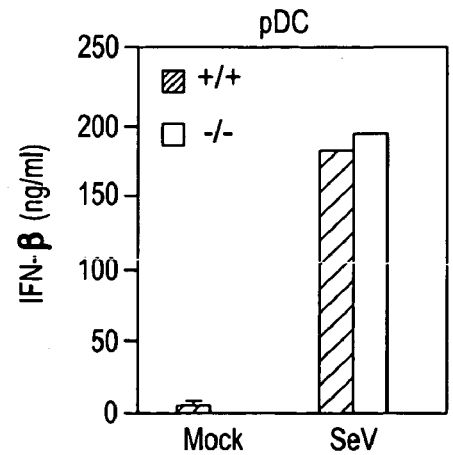

MAVS is Required for Interferon Induction in Conventional, but Not Plasmacytoid, Dendritic Cells. Dendritic cells play a pivotal role in bridging innate and adaptive responses, and these cells can be classified into conventional (cDC) and plasmacytoid dendritic cells (pDC), the latter being high producers of IFN-α/β (Liu, 2001). cDC and pDC were isolated from the bone marrow cultured with GM-CSF and Flt-3 ligand, respectively, and purified them by FACS sorting (the purities of cDC and pDC were 90-95%; FIG. 17I). These cells were stimulated with Sendai virus to measure cytokine production by ELISA. While cDC derived from the wild type and heterozygous mice were fully capable of producing IFN-α, IFN-β and IL-6, cDC from Mavs$^{-/-}$ mice were severely defective in producing these cytokines (FIG. 18A-C). When cDC from Mavs$^{-/-}$ mice were stimulated with LPS, poly(I:C) or CpG DNA (a TLR9 ligand), normal production of IL-6 was detected (FIG. 18C). In sharp contrast to cDC and other cell types, pDC from Mavs$^{-/-}$ mice produced comparable levels of IFN-α and IFN-β to those in wild type mice in response to Sendai virus infection (FIGS. 18D & 18E). Thus, as shown for RIG-I (Kato et al., 2005), the role of MAVS in interferon induction is cell type-dependent (see Discussion).

Figure 19A:
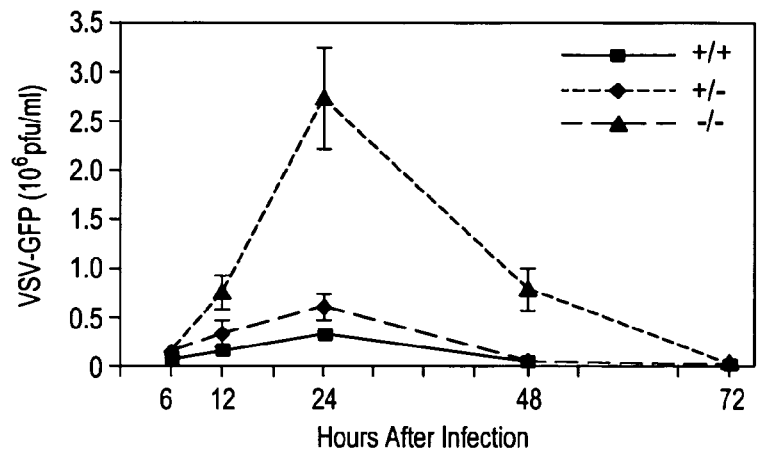
FIG. 19. MAVS is required for antiviral immune defense in vivo. (A) Wild type (n=7), Mavs$^{+/-}$ (n=5) and Mavs$^{-/-}$ (n=5) mice were infected with VSV-GFP (2×10$^8$ pfu) via tail vein injection. The sera were collected from the mice at different time point as indicated and used to measure viral titers by plaque assays. The error bars indicate standard errors. (B) Sera collected as in (A) were used for measurement of IFN-α and IFN-β by ELISA. The error bars indicate standard errors. (C) Mavs$^{+/+}$, Mavs$^{+/-}$ and Mavs$^{-/-}$ mice (n=6 for each genotype) were infected with wild type VSV (Indiana strain.
Figure 19B:
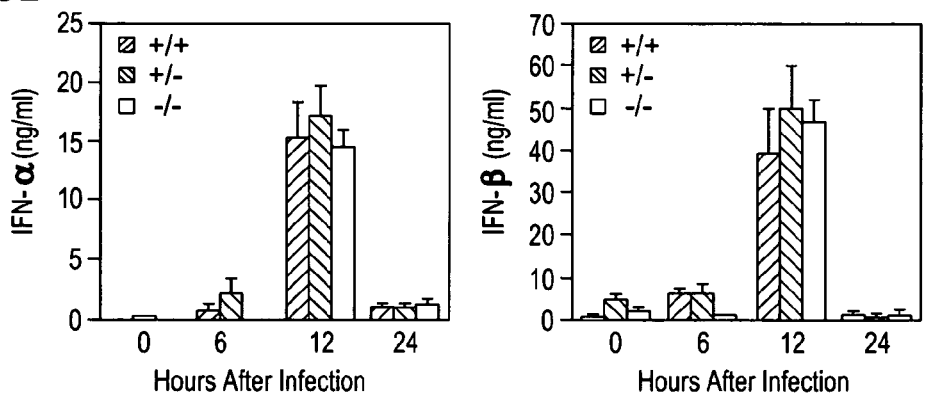

MAVS is Essential for Antiviral Immune Defense in vivo. To investigate the role of MAVS in antiviral responses in vivo, wild type and mutant Mavs mice were injected with VSV-GFP through the tail vein, and then collected sera to measure viral titers and interferon production. At 12-48 hours after viral infection, the viral titers in the Mavs$^{-/-}$ mice were significantly higher than those in the wild type and heterozygous mice (FIG. 19A). Nevertheless, the virus was largely cleared in both wild type and mutant mice at 72 hours post infection, suggesting that the immune system was still effective in clearing the virus in the absence of MAVS. Consistent with this notion, the sera of the Mavs$^{-/-}$ mice contained similar amounts of IFN-α and IFN-β to those of wild type mice (FIG. 19B), indicating that some cells in mice, likely pDC, could still produce sufficient amounts of interferons when the RIG-I-MAVS pathway was crippled.

Figure 19C:
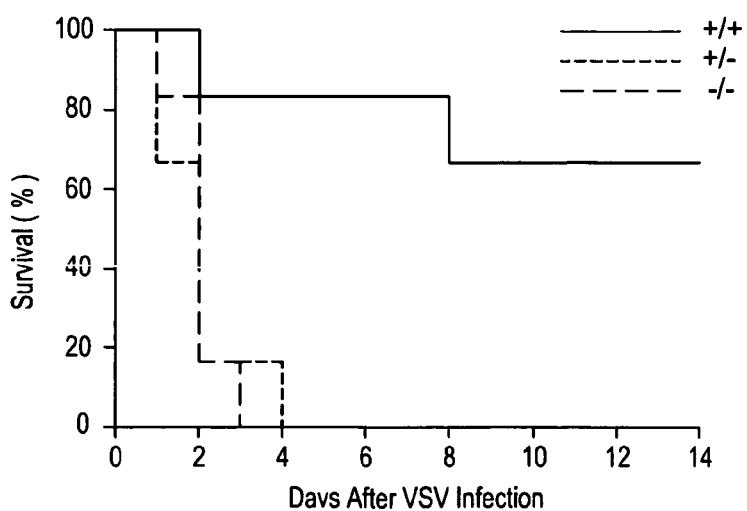
Figure 19D:
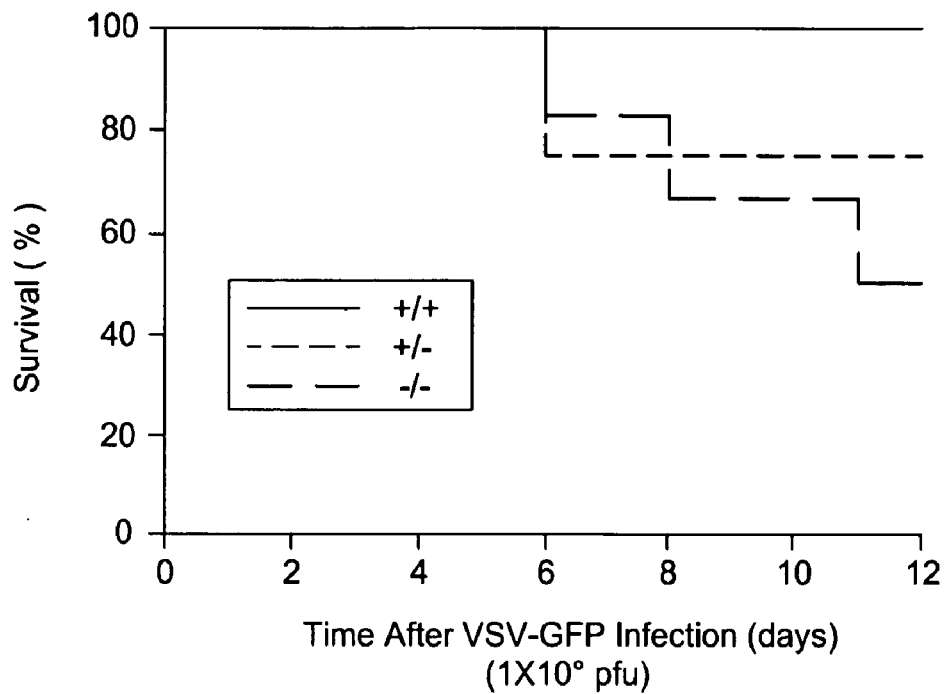
Figure 19E:
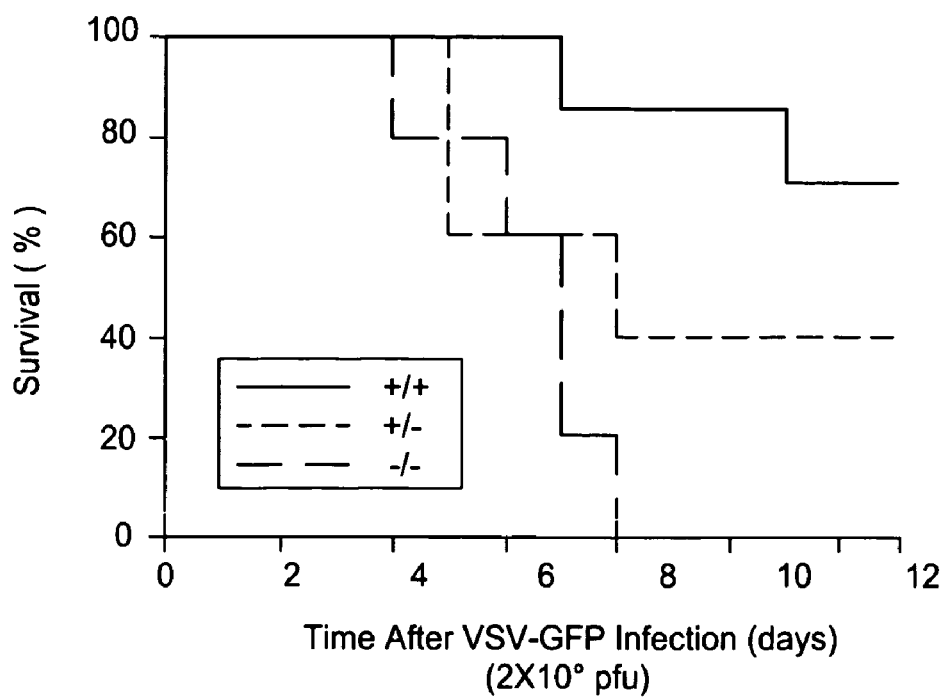

To determine if MAVS deficiency affects the survival of mice following viral infection, mice were infected with the wild type VSV (Indiana strain), and monitored their survival. As shown in FIG. 19C, while the majority of wild type mice (4/6) survived VSV infection, all of the Mavs$^{+/-}$ and Mavs$^{-/-}$ mice died within 4 days after the viral infection. The high mortality rate of Mavs$^{+/-}$ mice was surprising, as cell culture studies showed that Mavs$^{+/-}$ cells were capable of inducing interferons. To determine if there is a quantitative difference in the viability of mice carrying different copies of Mavs, these mice were infected with VSV-GFP, which is less virulent (FIGS. 19D & 19E). When $2\times10^8$ pfu of the virus was used to infect each mouse, all Mavs$^{-/-}$ mice died within 8 days (n=5), whereas 2 out of 5 Mavs$^{+/-}$ and 5 out of 7 wild type mice survived at 12 days. At $1\times10^8$ pfu per mouse, 50% of Mavs$^{-/-}$ mice (n=6) succumbed to viral infection at day 12, whereas 3 out of 4 Mavs$^{+/-}$ and all of wild type (n=4) mice remained alive. When the viral titer was further reduced to $5\times10^7$ pfu per mouse, none of the mice died of viral infection within 20 days, although the Mavs$^{-/-}$ mice appeared sick and later recovered (data not shown). Thus, MAVS protects the mice from VSV-induced mortality in a manner that depends on its gene dosage as well as the viral titer. These results suggest that interferons produced by pDC and other cells through the TLR pathway are not sufficient to protect mice from viral killing, and that the RIG-I-MAVS pathway may provide innate immunity through local production of interferons and/or other antiviral molecules. In the absence of MAVS, the initial high viral load might have caused irreversible damages to the mice that they failed to recover even after the virus was cleared. The observation that Mavs mice were vulnerable to VSV killing is particularly interesting, as it suggests that the expression level of MAVS is critical to antiviral immune defense (see below).

Figure 20A:
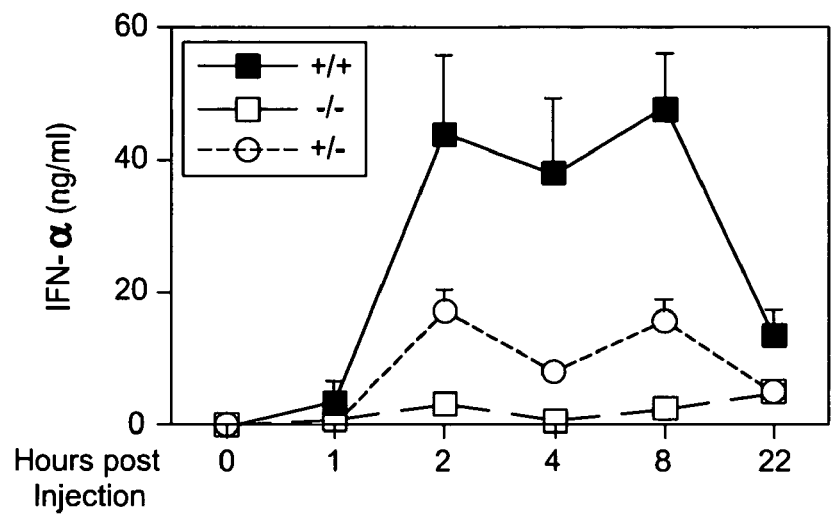
Figure 20B:
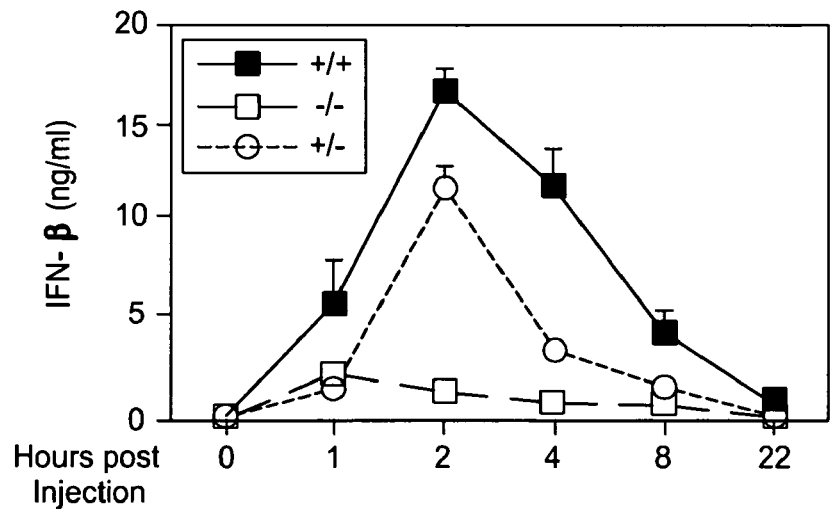
Figure 20C:
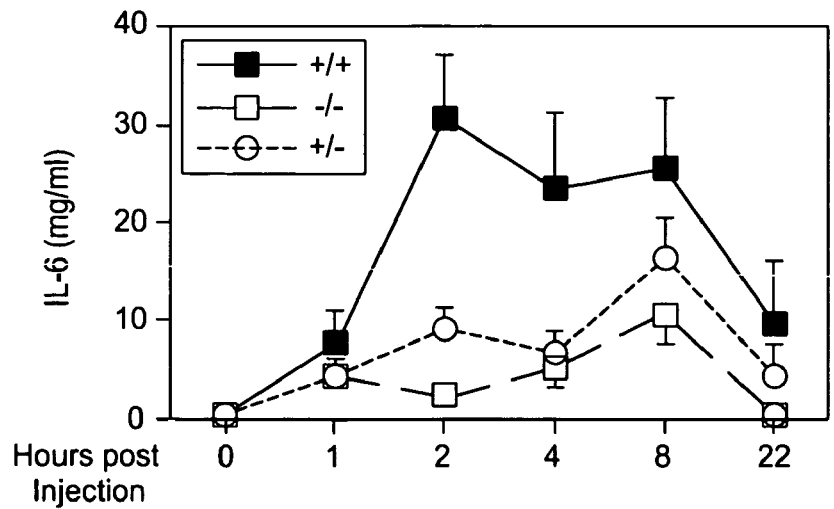

MAVS is Required for Interferon Induction by Poly(I:C) in vivo. As pDC appears to be the major source of interferons elicited by VSV infection in vivo and this may mask the contribution of interferon production by other cell types, the role of MAVS in interferon induction by poly(I:C) was examined, which activates the cytosolic RNA sensing pathway in most cell types. Intravenous injection of poly(I:C) led to a rapid and robust induction of IFN-α, IFN-β and IL-6 in the sera of wild type mice (FIG. 20A-20C). In contrast, the Mavs$^{-/-}$ mice failed to produce IFN-α and IFN-β, and the induction of IL-6 within the first 4 hours of poly(I:C) injection was also impaired. However, there was a late induction of IL-6 in Mavs$^{-/-}$ mice, albeit at a much reduced level as compared to the wild type (FIG. 20C; 8 hour time point). This may be due to the induction of IL-6 through TLR3 but not MAVS (see also FIG. 16C). Interestingly, Mavs$^{+/-}$ mice produced intermediate levels of IFN-α, IFN-β and IL-6, indicating that the gene dosage of Mavs is important for the cytosolic RNA signaling pathway. As the amount of MAVS protein in Mavs$^{+/-}$ cells is about half of that in the wild type cells (FIG. 14C), these results indicate that the steady state level of MAVS protein is a limiting factor in mounting an effective antiviral response in vivo.

The present inventors have genetic evidence that MAVS is essential for antiviral innate immune responses in fibroblasts, macrophages and conventional dendritic cells, but not in plasmacytoid dendritic cells. The cell type-specific requirement of MAVS in antiviral immunity is similar to that of RIG-I (Kato et al., 2005). However, RIG-I knockout mice are not viable, suggesting that RIG-I might be involved in other processes currently not understood. In contrast, Mavs$^{-/-}$ mice displayed no apparent developmental abnormality, but they were severely compromised in immune responses against viral infection. Thus, these results provide the genetic evidence that the cytosolic viral sensing and signaling pathway through MAVS is essential for antiviral immune defense in vivo. Interestingly, nornal levels of interferons are still detected in the sera of Mavs$^{-/-}$ mice, suggesting that other cell types such as pDC can still produce interferons in the absence of MAVS. Nevertheless, Mavs$^{-/-}$ mice have higher initial viral loads and are much more vulnerable to viral killing. Thus, although the host immune system is endowed with different cell types that provide two partially redundant antiviral pathways, TLR and RIG-I/MDA-5, each of these pathways is important for effective antiviral responses in vivo.

Previous studies have presented conflicting data concerning the role of MAVS in TLR signaling (Seth et al., 2006). While two reports showed that RNAi of MAVS/IPS-1 did not affect interferon induction by TRIF or poly(I:C) (Kawai et al., 2005; Seth et al., 2005), another report found that MAVS/VISA interacts with TRIF and is required for TLR3 signaling (Xu et al., 2005). Using MAVS-deficient cells, it was found that MAVS is not required for interferon induction by TLRs in multiple cell types. Therefore, TLRs and RIG-I are parallel antiviral signaling pathways that detect viral RNA in topologically different locations. The TLRs involved in viral sensing, including TLR3, 7, 8 and 9, are localized on the endosomal membrane, with the ligand sensing domain facing the lumen of the endosome (O'Neill, 2004). These TLRs detect viral RNA following the endocytosis and disassembly of the viral particles, and then transduce signals through the cytosolic Toll-IL1-Receptor (TIR) domain, which recruits MyD88 or TRIF to activate NF-κB and IRFs. In contrast to TLRs, RIG-I is a cytosolic receptor that detects double-stranded RNA generated during viral replication in the cytosol. It has been proposed that some RNA viruses such as respiratory syncytial virus (RSV) and Sendai virus, which enter host cells through fusion with the plasma membrane, induce type-I interferons through cytosolic RNA sensing pathway instead of TLR pathways in most cells including pDC (Hornung et al., 2004). Indeed, Sendai virus has been shown to induce interferons in pDC derived from Myd88$^{-/-}$ and Pkr$^{-/-}$ mice (Hornung et al., 2004). Since signaling by TLR7 and TLR9 in pDC is strictly dependent on MyD88, our finding that Mavs$^{-/-}$ pDC is still fully capable of inducing interferons (FIGS. 18D & 18E) raises the interesting possibilities that either MAVS and MyD88 function redundantly or there is a third pathway (MAVS- and MyD88-independent) that mediates the induction of type-I interferons in pDC in response to infection by some viruses such as Sendai virus.

The TLR and RIG-I pathways use distinct adaptors to activate IKK and TBK1/IKKε. The use of MAVS as an essential adaptor in the RIG-I pathway is particularly interesting, as the function of MAVS depends on its localization on the mitochondrial membrane. The importance of the mitochondrial localization of MAVS is underscored by the recent discovery that hepatitis C virus (HCV) employs a serine protease NS3/4A to cleave MAVS off the mitochondrial membrane, thereby blocking interferon induction by the viral RNA (See Example 3)(Li et al., 2005; Meylan et al., 2005). However, the in vivo situations appear to be more complicated, as microarray analyses have revealed abundant intrahepatic expression of IFN-stimulated genes (ISG) in HCV-infected chimpanzees, suggesting that IFNs are produced even though MAVS might have been cleaved in these animals (Bigger et al., 2004; Wieland and Chisari, 2005). This conundrum is reminiscent of the present inventors' observation that Mavs$^{-/-}$ mice remain capable of producing high levels of interferons following VSV infection. Thus, it is possible that both VSV and HCV can induce interferons through the TLR pathway in some cell types such as pDC. Although HCV is a hepatotropic virus, it can also infect and replicate in extrahepatic tissues such as B cells (Machida et al., 2006). In addition, a recent study has shown that the hepatoma cell line Huh7 expresses TLR7 (Lee et al., 2006), which could induce interferons in response to viral infection. Although the source of interferons in HCV-infected host remains to be investigated, the cleavage of MAVS by the HCV protease likely contributes to the pathogenesis of this widespread virus, as suggested by our finding that Mavs$^{-/-}$ mice were highly susceptible to viral killing. The importance of MAVS in antiviral defense may partially explain why the HCV protease inhibitors are highly effective in rapidly reducing HCV viral loads in early-stage clinical trials (Lamarre et al., 2003); these inhibitors are expected to not only inhibit viral replication and assembly, but also restore the host antiviral innate immunity by blocking the cleavage of MAVS.

Recent studies have uncovered a novel signaling pathway that induces interferons in response to cytosolic DNA, which can be introduced to the host cells through bacterial or viral infection or under certain pathological conditions that fail to degrade self-DNA during apoptosis (Ishii et al., 2006; Okabe et al., 2005; Stetson and Medzhitov, 2006). It has also been shown that *Listeria monocytogenes* induces interferon by releasing. the bacterial DNA into the host cytoplasm (Stetson and Medzhitov, 2006). In addition, it was reported that RNAi of MAVS/IPS-1 partially inhibited the induction of an interferon reporter in cultured cells, leading to the proposal that MAVS/IPS-1 is required for signaling by cytosolic DNA (Ishii et al., 2006). However, the inventors' studies using MAVS-deficient cells have shown clearly that MAVS is not required for interferon induction by cytosolic DNA or *Listeria monocytogenes*. Previous studies have also shown that RIG-I is not required for interferon induction by cytosolic DNA (Ishii et al., 2006), and that TLR, NOD1, NOD2 and RIP2 are dispensable for interferon induction by *Listeria monocytogenes* (O'Connell et al., 2005; Stockinger et al., 2004). Using the present invention, the skilled artisan can identify the sensor(s) of cytosolic DNA and the adaptor(s) that transduce the DNA signals to the activation of IKK and TBK1/IKKε.

The in vivo studies of Mavs mutant mice showed that both Mavs$^{-/-}$ and Mavs$^{+/-}$ mice were highly vulnerable to killing by VSV, suggesting that the dosage of MAVS is critical for antiviral immune defense. Since the Mavs mutant mice had normal levels of interferons in the circulation, the sensitivity of these mice to viral killing is likely due to the defect in the local production of antiviral molecules (Levy, 2002). Interferons and cytokines may be such molecules, as the production of IFN-α, INF-β and IL-6 was abolished in Mavs$^{-/-}$ mice that were stimulated with poly(I:C). A recent study has shown that poly(I:C) induces interferons through Mda5, but not RIG-I (Kato et al., 2006). Thus, these results provide the in vivo evidence that MAVS is essential for signaling downstream of Mda5, and it serves as a convergent point for both Mda5 and RIG-I pathways. Interestingly, the induction of interferons and IL-6 by poly(I:C) was also severely compromised in Mavs$^{+/-}$ mice, suggesting that one copy of Mavs is not sufficient to mediate full antiviral responses. That Mavs$^{+/-}$ mice are severely immune compromised may have important implications in human immunogenetics. It will be of great interest to analyze the Mavs gene locus in human populations to determine whether individuals homozygous and heterozygous for Mavs mutations have increased susceptibility to viral diseases.

Generation of Mavs-Deficient Mice. Genomic DNA containing the Mavs gene was isolated from 129/Sv mouse ES cell genomic DNA by PCR. The targeting vector was constructed by replacing a 1.7 kb fragment spanning from the ATG start codon of exon 2 to exon 3 of Mavs with a PGK-Neo positive selection cassette, which also contained two loxP sites flanking PGK-Neo. After electroporation of the Mavs targeting vector, three independently targeted ES cell clones were injected into C57BL/6 blastocysts to produce chimeric mice. Chimeric mice obtained from two targeted ES clones were bred to C57BL/6 mice to obtain germline transmission. The heterozygous F1 progenies were intercrossed to obtain Mavs$^{-/-}$ mice. Mice from these independent clones displayed indistinguishable phenotypes. The mice used in this study were 129/Sv/C57BL/6 hybrids. However, only littermates from the crossing of heterozygous mice were used in the same studies. All mice described in this report were engineered and housed in animal facilities at the University of Texas Southwestern Medical Center in compliance with guidelines set by Institutional Animal Care and Use Committee.

Antibodies. To generate polyclonal antibodies against mouse MAVS, a recombinant protein containing residues 127-276 of mouse MAVS was expressed in *E. coli* as a His$_6$-tagged protein and affinity purified. This protein fragment was used to immunize rabbits and the sera were further purified using the antigen column to obtain the MAVS antibodies. The antibody for mouse IRF3 was purchased from Zymed Inc, and antibodies for PARP and caspase 3 were from Cell Signaling Inc. FITC-conjugated antibodies against CD11c and CD11b, PE-conjugated antibody against B220, and APC-Annexin V were purchased from BD Pharmingen.

Cells. Embryonic fibroblasts from wild type and mutant mice were prepared from day 13.5 embryos and cultured in DMEM supplemented with 10% FBS. Bone marrow cells were prepared from the femurs and tibiae of mice. These cells were cultured in RPMI 1640 containing 10% FBS, 10 mM Hepes, pH 7.4, 50 µM B-mercaptoethanol and 100 ng/ml human Flt3 ligand (peproTech) or 10 ng/ml murine GM-CSF (peproTech). After 6-8 days, the cells were collected and used as Flt3L-induced BMDCs or GM-CSF-induced BMDCs, respectively. Flt3L-induced BMDCs were stained with antibodies against CD11c and B220 and sorted by FACS. FACS sorting was carried out using FACSVantage SE (with DIVA upgrade) after CD11c and B220 staining. CD11c$^+$B220$^+$ cells and CD11c$^+$B220$^-$ cells were used as bone marrow pDCs and cDCs, respectively. The purity of pDCs and cDCs was greater than 90% based on FACS analysis.

To isolate bone marrow derived macrophages, 1×10$^7$ bone marrow cells were cultured in DMEM containing 10% FBS and 10 ng/ml CSF-1 (Sigma). 24 hours later, non-adherent cells were transferred to a new flask and cultured for 3 days before 10 ml fresh media containing CSF-1 were added and cells were cultured for another 4 days. Mature macrophages were harvested by collagenase (Roche) digestion and cultured on 96-well or 12-well plates for studies. For peritoneal macrophages, cells were obtained by lavage of the peritoneal cavity with DMEM. Blood cells were lysed in ammonium chloride and macrophages were collected and resuspended in DMEM containing 10% FBS for further studies.

Stimulation of Cells and Functional Assays. To stimulate MEF cells or macrophages with cytosolic DNA, poly(dA:dT) or poly(dI:dC) (10 µg/ml; GE Biosciences) was incubated with lipofectamine 2000 (Invitrogen; 1 µl LF2000/µg DNA) at room temperature for 20 min and then added to cultured cells at the final concentration of 10 µg/ml of DNA. To stimulate TLR3, TLR4 or TLR9, cells were incubated with poly(I:C) (10 µg/ml; GE Biosciences), LPS (10 µg/ml; Sigma) or CpG-2084 DNA (TCCTGACGTTGAAGT; 5 µg/ml) (SEQ ID NO.: 13) (Lund et al., 2004), respectively. After incubation for indicated time periods, cell extracts were prepared to measure NF-κB activation by electrophoretic mobility shift assays (EMSA) or IRF3 activation by native gel dimerization assays (Seth et al., 2005). For EMSA, whole cell extracts were incubated with $^{32}$P end-labeled NF-κB oligos (AGT TGA GGG GAC TTT CCC AGG), (SEQ ID NO.: 14) and the protein-DNA complex was resolved by native gel electrophoresis. To measure the production of cytokines, culture supernatants were collected for ELISA. The ELISA kits for mouse IFN-α and IFN-β were purchased from PBL Biomedical Laboratories (Piscataway, N.J.), and the IL-6 ELISA kit was from BD Biosciences (San Diego, Calif.).

Viral and Bacterial Infection of Cells. Sendai virus (Cantell strain) and VSV (Indiana strain) have been described previously (Seth et al., 2005). VSV-GFP virus (kindly provided by Dr. Genhong Cheng; UCLA) was propagated in BHK21 cells (Oganesyan et al., 2006). *Listeria* monocytogenes (10403 serotype) were cultured in 3.7% Brain-Heart Infusion overnight (Berg et al., 2003). The bacteria were washed three times in PBS before being used to infect cells.

For viral infection, cells grown in media containing 1% FBS were incubated with viruses at the indicated MOIs for 1 hour before replacement with the complete media containing 10% FBS. For listerial infection, cells were incubated with the bacteria at MOI of 10 or 100 in antibiotic-free DMEM containing 10% FBS. After infection for 1 hour, excess bacteria were washed away and cells were incubated in complete media containing 50 µg/ml gentamycin.

Viral Infection and Poly(I:C) Injection in Mice and Measurement of Viral Titer. Mice of different genotypes were infected with VSV (5×10$^7$ pfu per mouse) or VSV-GFP (1×10$^8$ or 2×10$^8$ pfu per mouse) via tail vein injection. The viability of the infected mice was monitored for 2-5 weeks. Sera were collected at different time points to measure interferon induction by ELISA as described above and viral titers by plaque assays. For plaque assays, BHK21 cells were incubated with viral samples at serial dilutions for 1 hour and then overlaid with 1.5% methylcellulose in MEM containing 1% FBS. 48 hours later, cells were fixed in methanol and stained with 0.1% crystal violet. Plaques were counted to calculate viral titer. For poly(I:C) injection, 200 µg of poly(I:C) was injected into each mouse intravenously, and the sera were collected for ELISA as described above.

EXAMPLE 3

The Hepatitis C Virus Protease NS3/4A Cleaves MAVS off the Mitochondria to Evade Innate Immunity. Hepatitis C virus (HCV) is a global epidemic manifested mainly by chronic infection. One strategy that HCV employs to establish chronic infection is to use the viral serine protease NS3/4A to cleave some unknown cellular targets involved in innate immunity. Here it is shown that the target of NS3/4A is MAVS, a mitochondrial antiviral signaling protein that activates NF-κB and IRF3 to induce type-I interferons. NS3/4A cleaves MAVS at Cys-508, resulting in the dislocation of the N-terminal fragment of MAVS from the mitochondria. Remarkably, a point mutation of MAVS at Cys-508 renders MAVS resistant to cleavage by NS3/4A, thus maintaining the ability of MAVS to induce interferons in HCV replicon cells. NS3/4A binds to and co-localizes with MAVS in the mitochondrial membrane, and it can cleave MAVS directly in vitro. These results provide an example of host-pathogen interaction in which the virus evades innate immunity by dislodging a pivotal antiviral protein from the mitochondria, and suggest that blocking the cleavage of MAVS by NS3/4A may be applied to the prevention and treatment of HCV.

Hepatitis C virus (HCV) infects more than 170 million people in the world, and approximately 80% of the infected individuals develop persistent infection. HCV is an enveloped single-strand RNA virus belonging to the Flaviviridae family. It contains a 9.6-kb RNA genome that encodes a large polyprotein (over 3000 amino acids), which is cleaved into ten structural and non-structural (NS) proteins through the action of cellular peptidases as well as the viral encoded proteases including NS3/4A. NS3 contains serine protease and RNA helicase activities that require its cofactor NS4A, which tethers the holoenzyme complex to an intracellular membrane compartment. The NS3/4A protease is not only essential for generating mature viral proteins required for viral replication, but can also suppress the host antiviral immune system by cleaving putative cellular targets involved in the induction of type-I interferons (WN), such as IFN-α and IFN-β (3).

The induction of interferons is regulated by the transcription factors NF-κB and IRF3, which are activated by a signaling cascade emanating from double-stranded RNA (dsRNA) generated during the replication of viral RNA (4, 5). The activation of NF-κB requires the phosphorylation of its inhibitor IκB by the IκB kinase (IKK) complex, which can be activated by a large variety of agents, including proinflammatory cytokines and microbial pathogens (6). The phosphorylation of IκB targets this inhibitor for ubiquitination and subsequent degradation by the proteasome, thereby allowing NF-κB to enter the nucleus to regulate downstream genes. The activation of IRF3 requires its phosphorylation by two IKK-related kinases, TBK1 and IKKε (7, 8). Following phosphorylation, IRF3 is dimerized and translocated into the nucleus where it forms an enhanceosome complex together with NF-κB and other transcription factors to turn on the expression of targets genes such as IFN-β (4). Interferons then induce a large array of antiviral genes through the activation of the JAK-STAT pathway.

The receptor for intracellular viral dsRNA has recently been identified as RIG-I, which contains an RNA helicase domain that binds to dsRNA(9). RIG-I also contains tandem N-terminal CARD domains that interact with another CARD domain protein MAVS (also known as IPS-1, VISA and CARDIF) (10-13). MAVS contains a C-terminal transmembrane (TM) domain that targets it to the mitochondrial outer membrane (Seth, R. B.,. Sun, L., Ea, C. K. & Chen, Z. J. (2005) Cell 122, 669-82). Importantly, the mitochondrial localization of MAVS is essential for its signaling function, as the removal of the mitochondrial targeting domain of MAVS abolishes its ability to induce interferons. Epistasis studies have shown that MAVS functions downstream of RIG-I and upstream of IKK and TBK1 in the viral signaling pathway.

Recent studies have shown that NS3/4A inhibits interferon induction by RIG-I; however, RIG-I is not cleaved by NS3/4A(14, 15). NS3/4A was also found to cleave TRIF (16), an adaptor protein that binds to Toll-like receptors such as TLR3 and TLR4 (17). However, TRIF is not essential for interferon induction by viruses (18). Thus, the target of NS3/4A in the viral pathway remains to be identified. Therefore, MAVS is the proteolytic target of NS3/4A. It was found that NS3/4A cleaves MAVS at Cys-508, resulting in the dislocation of the N-terminal fragment of MAVS from the mitochondria, thereby suppressing the induction of IFN-β. A point mutation at Cys-508 prevents the cleavage of MAVS by NS3/4A, and restores IFN-β induction in a HCV replicon cell line, suggesting that the cleavage of MAVS is responsible for the suppression of interferon induction in HCV replicating cells. Also shown is that NS3/4A binds to and colocalizes with MAVS in the mitochondria. Finally, it is shown that NS3/4A cleaves MAVS at Cys-508 in vitro, providing the direct biochemical evidence that MAVS is the target of NS3/4A.

Plasmids and antibodies. Expression constructs for MAVS, MAVS (CARD-TM), TBK1, RIG-I(N), IFN-β-Luc, NF-κB-Luc, UAS-Luc, and Gal4-IRF3 have been described previously( Seth, R. B., Sun, L., Ea, C. K. & Chen, Z. J. (2005) Cell 122, 669-82). pcDNA3-Flag-MAVS-HA was constructed by subcloning the DNA fragment encoding MAVS-HA into the XhoI and XbaI sites of the pcDNA3-Flag vector such that the N-terminal Flag epitope was fused in frame with MAVS-HA. NS3/4A was amplified by RT-PCR from the RNA of HCV replicon cell line K2040 (19), and then cloned into pcDNA3 in frame with an N-terminal Flag or Myc tag. The S139A mutant of NS3/4A and the cysteine mutants of MAVS (C435R, C452R and C508R) were generated by site-directed mutagenesis using the QuickChange kit (Strategene). PET14b-NS3/4A was constructed by subcloning NS3/4A into the XhoI and BamH1 sites of pET14b (Novagen). All plasmids were verified by automatic DNA sequencing.

The polyclonal antibody against MAVS was generated and purified by antigen column as previously described (Seth, R. B., Sun, L., Ea, C. K. & Chen, Z. J. (2005) Cell 122, 669-82). The HCV NS3 antibody was purchased from Novocastra Laboratories Ltd. The monoclonal antibodies against Flag (M2, Sigma), Myc (9E10, Santa Cruz) and HA (HA.11, Covance) were purchased from the indicated suppliers.

Cell culture, transfection, and luciferase reporter assays. HEK293 and HeLa cells were from ATCC. The Huh7 and HCV replicon cell line K2040 were provided by Dr. Michael Gale (UT Southwestern) (19). Transfection of HEK293 cells was carried out using the calcium phosphate precipitation method. HeLa cells were transfected using the PolyFect reagent (Qiagen). Huh7 and replicon cells were transfected using lipofectamine 2000 (Invitrogen) or Superfect (Qiagen) reagents. Luciferase reporter assays were performed as described previously(10).

Subcellular fractionation. HEK293 cells were transfected with expression vectors for Flag-MAVS-HA or the C508R mutant together with Myc-tagged NS3/4A or its inactive mutant S139A. 36 hr after transfection, cells were washed in the hypotonic buffer [10 mM Tris-HCl, pH7.5, 10 mM KCl, 1.5 mM MgCl$_2$, and protease inhibitors] and then homogenized in the same buffer by douncing for 20 times. The homogenate was centrifuged at 500×g for 5 minutes to remove nuclei and unbroken cells. The supernatant was centrifuged again at 5,000×g for 10 minutes to generate membrane pellets (P; containing mostly mitochondria) and cytosolic supernatant (S). The same procedure was used for subcellular fractionation of Huh7 and HCV replicon cells.

Cleavage of MAVS by NS3/4A protease in vitro. pcDNA3-Flag-NS3/4A or its mutant S139A was transfected into HEK293 cells to express the protease, which was then purified by binding to the Flag-Sepharose (M2-Sepharose, Sigma) followed by elution with the Flag peptide (0.2 mg/ml). The eluted NS3/4A or S139A mutant was concentrated using Amicon microconcentrator (Millipore, 10,000 Dalton cut-off) and diluted in Buffer A (20 mM Tris-HCl, 150 mM NaCl, 0.1% Triton X-100, and 5 mM DTT). This procedure was repeated three times to reduce the concentration of the Flag peptide. For expression of NS3/4A in E. coli, pET14b-NS3/4A was transfected into the E.coli strain BL21/pLysS, and the transformant was induced to express His$_6$-NS3/4A following the addition of IPTG. His$_6$-NS3/4A was purified using nickel affinity column and dialyzed against Buffer B (20 mM Tris-HCl, pH 7.5, 100 mM NaCl, 10% glycerol).

Flag-MAVS or its mutant C508R was translated in vitro using the TNT rabbit reticulocyte lysate (Promega) supplemented with $^{35}$S-Methionine. The $^{35}$S-labeled Flag-MAVS or C508R was purified using Flag-Sepharose as described above for NS3/4A. To measure the cleavage of MAVS by NS3/4A, 0.5 µl of $^{35}$S-labeled MAVS or C508R was incubated with 0.5 µl of NS3/4A or S139A in a 10 µl reaction containing Buffer A. After incubation at 30° C. for 2 hours, the reaction products were resolved by SDS-PAGE and analyzed using PhosphorImager (Molecular Dynamics).

The procedures for viral infection, immunoblotting, immunoprecipitation, and confocal microscopy have been described previously (Seth, R. B., Sun, L., Ea, C. K. & Chen, Z. J. (2005) Cell 122, 669-82).

Figure 21A:
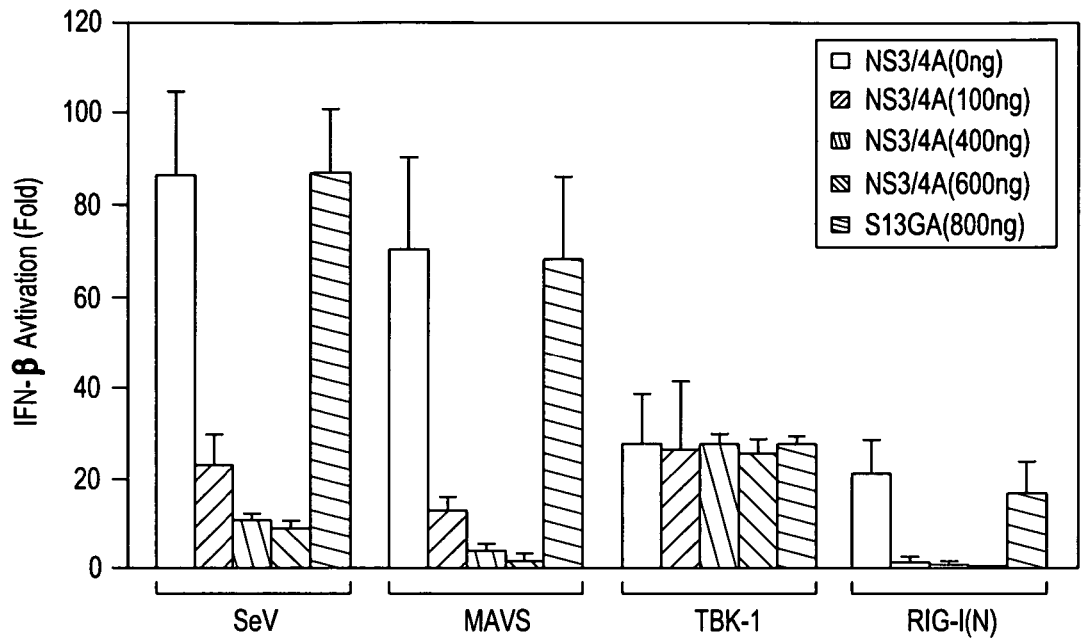
Figure 21B:
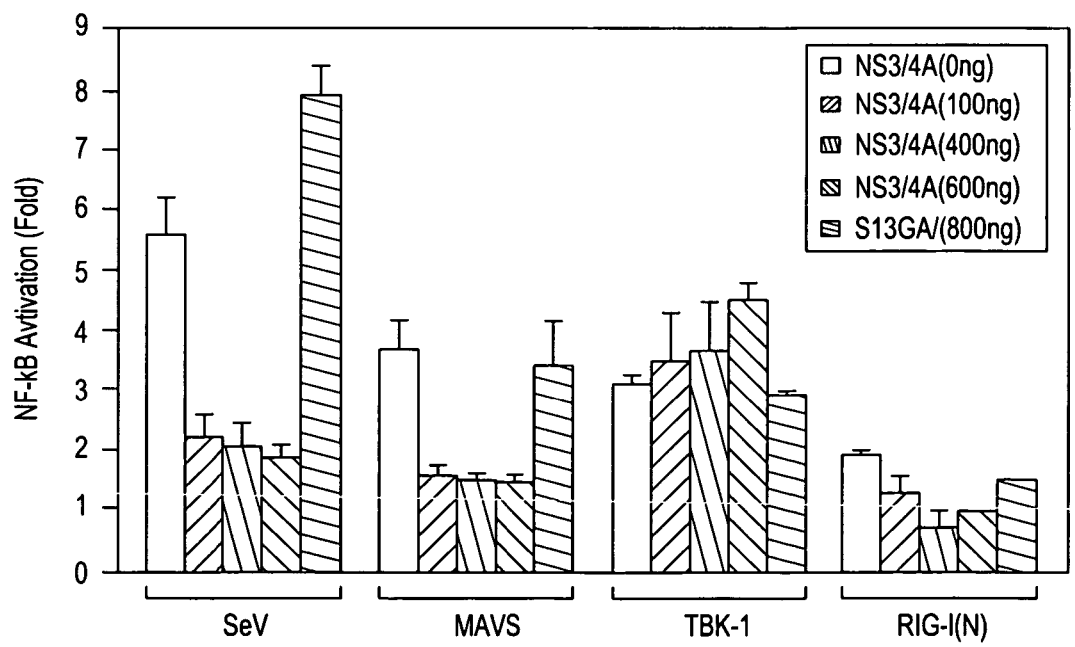
Figure 21C:
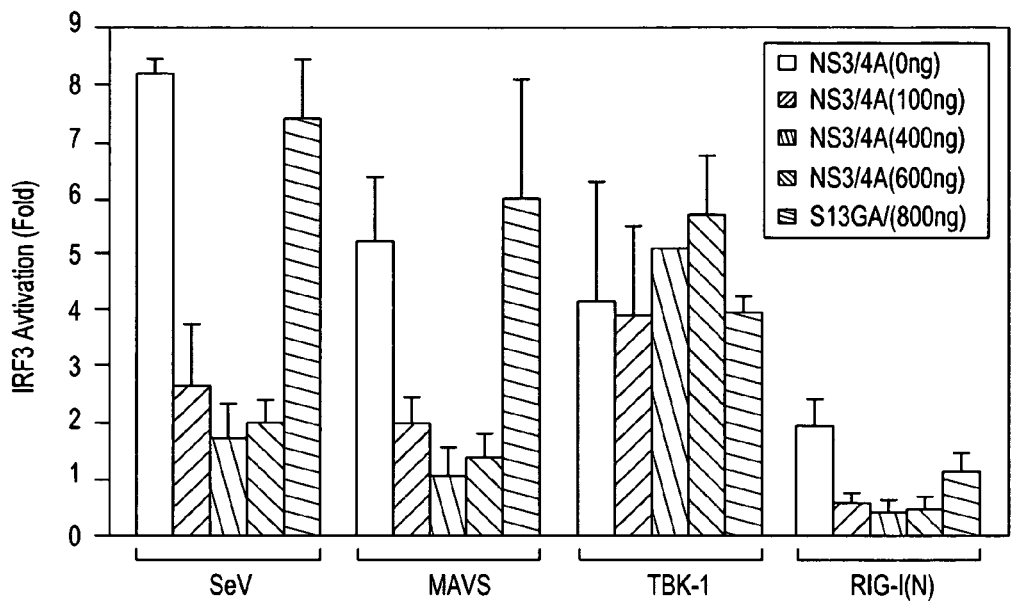
Figure 21D:
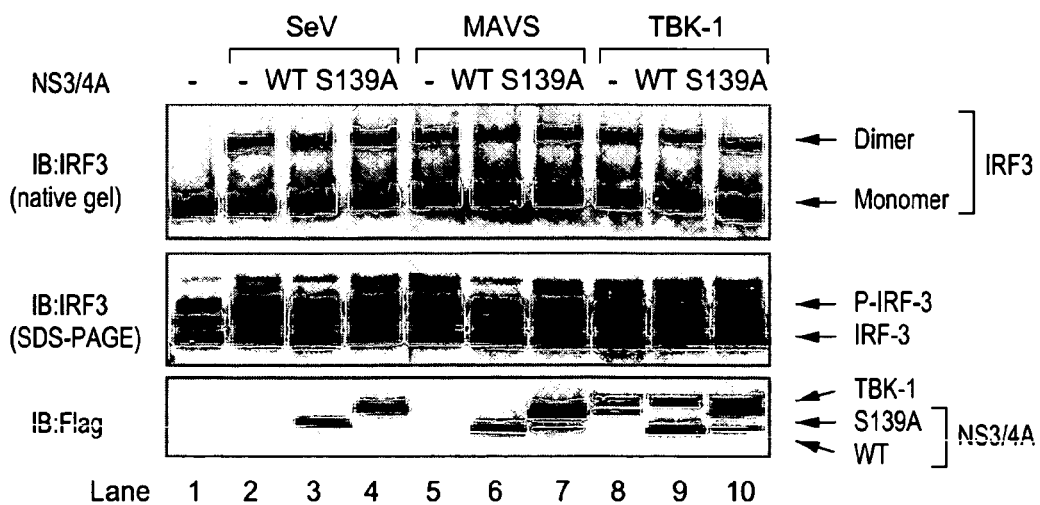

NS3/4A blocks IFN-β induction by MAVS. To determine if NS3/4A inhibits IFN-β induction by MAVS, expression vectors encoding NS3/4A and MAVS were transfected into HEK293 cells together with a luciferase reporter driven by the IFN-β promoter (IFNβ-Luc). As controls, cells with Sendai virus (SeV) or transfected cells were infected with an expression vector encoding the N-terminal CARD domains of RIG-I [RIG-I(N)], which has previously been shown to induce IFN-β (9). In each case, NS3/4A inhibited the induction of IFN-β (FIG. 21A). In contrast, the induction of IFN-β by TBK1 was not affected by NS3/4A, suggesting that NS3/4A inhibits the RIG-I pathway at the level of MAVS or at a step downstream of MAVS but upstream of TBK1. To determine if the protease activity of NS3/4A was required for this inhibition, the active site Ser-139 of NS3/4A was mutated (equivalent to Ser-1165 of the HCV polyprotein) to alanine (20, 21). This mutant migrated more slowly than the wild type NS3 (FIG. 21D, bottom panel), as it could no longer be cleaved at the junction between NS3 and NS4A. The protease-dead mutant completely lost its ability to inhibit IFN-β induction by Sendai virus, RIG-I(N) or MAVS. Thus, it is likely that NS3/4A inhibits interferon induction by cleaving MAVS or a target downstream of MAVS. NS3/4A also prevented the MAVS-induced activation of NF-κB (FIG. 21B) and IRF3 reporters (FIG. 21C), as well as the phosphorylation and dimerization of IRF3 (FIG. 21D), further supporting the notion that NS3/4A inactivates a common target required for both NF-κB and IRF3 activation.

Figure 22A:
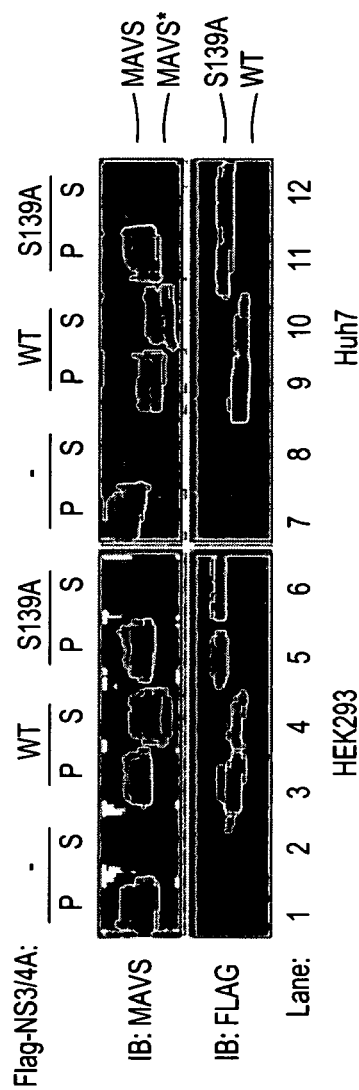

MAVS is the proteolytic target of NS3/4A. To determine if MAVS is the proteolytic target of NS3/4A, the expression vector encoding FLAG-NS3/4A or FLAG-NS3/4A (S139A) was transfected into HEK293 or Huh7 (a human hepatoma cell line). As MAVS is a mitochondrial membrane protein, the cell lysates were separated into cytosolic fraction (S) and membrane pellets (P) by centrifugation, and the endogenous MAVS protein analyzed by immunoblotting with an affinity-purified MAVS antibody (FIG. 22A). In both cell lines, the expression of NS3/4A, but not the protease-dead mutant of NS3/4A, led to the generation of a faster-migrating fragment of MAVS that was approximately 3-5 kDa shorter than the full-length MAVS (compare lanes 3 & 4, 9 & 10; upper panel). Interestingly, unlike the full-length MAVS that was present in the membrane pellet, the truncated fragment of MAVS was mainly present in the soluble cytosolic fraction, suggesting that the truncated fragment did not contain the C-terminal transmembrane domain. Immunoblotting studies also showed that the majority of NS3 is in the membrane pellet, presumably due to its association with NS4A (FIG. 22A, lower panel).

Figure 22B:
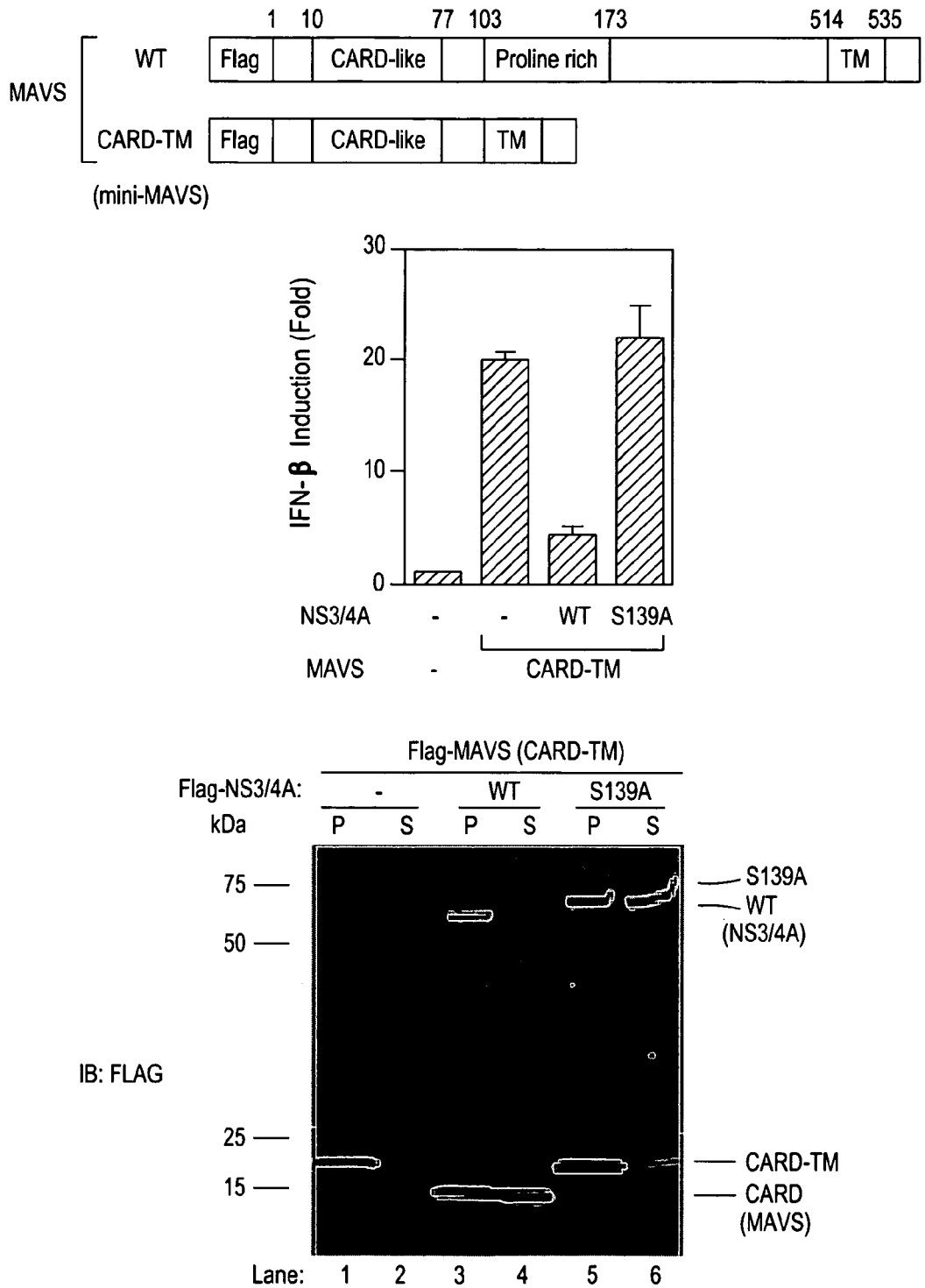

MAVS contains an N-terminal CARD domain, a middle proline-rich domain, and a C-terminal transmembrane (TM) domain. The present inventors have previously shown that a truncated MAVS protein containing only the CARD and TM domains (herein referred to as mini-MAVS) is sufficient to induce IFN-β (10). To further delineate the NS3/4A cleavage site of MAVS, whether the mini-MAVS was also sensitive to NS3/4A inhibition was tested. As shown in FIG. 22B, IFN-β induction by the mini-MAVS was also inhibited by NS3/4A (middle panel). Furthermore, the mini-MAVS was cleaved to a shorter fragment by the wild type, but not the S139A mutant, of NS3/4A (FIG. 22B, lower panel). The truncated fragment was also about 4 kDa shorter than the mini-MAVS (FIG. 22B, compare lane 4 & 5), suggesting that this small MAVS protein of only 140 residues in length contains a cleavage site of NS3/4A, most likely at a residue near the TM domain.

Figures 22C, 22E:
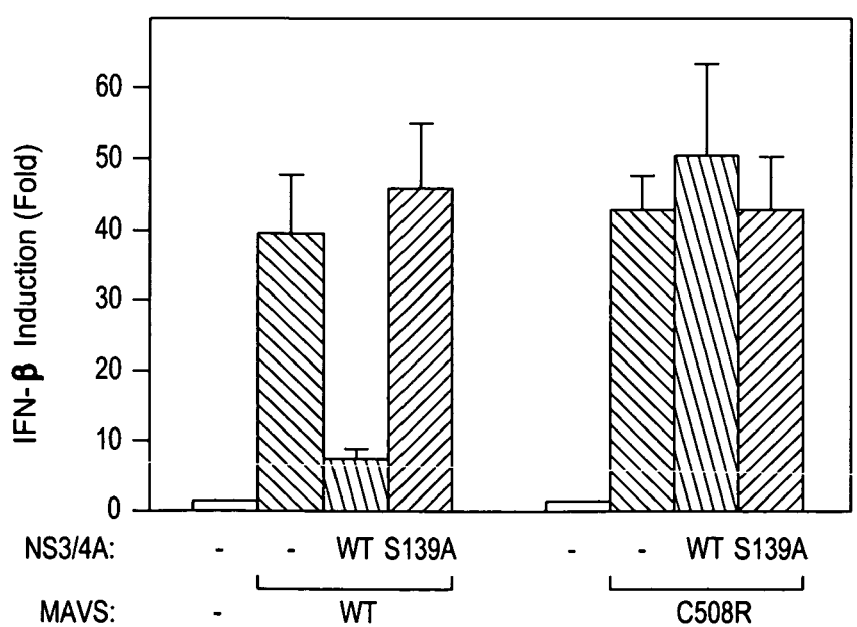
Figure 22D:
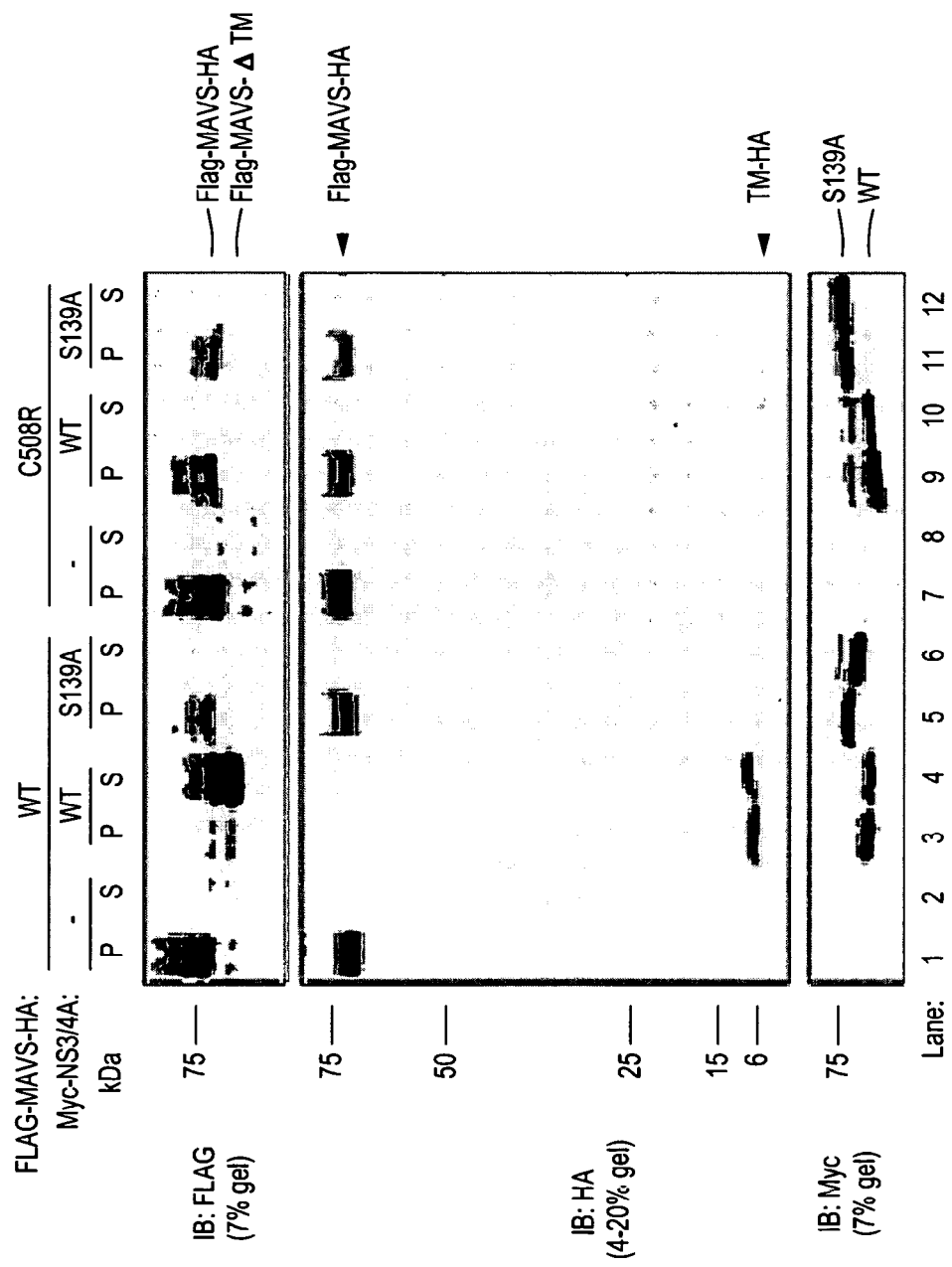

NS3/4A Cleaves MAVS at Cys-508. NS3/4A is a serine protease that cleaves at the C-terminus of a Cys or Thr residue within a loosely defined consensus sequence [(E/D)xxxx(C/T)(S/A), where x denotes any amino acid], which is found at the junction of HCV nonstructural proteins (FIG. 22C) (22). Inspection of the mini-MAVS amino acid sequence revealed a potential NS3/4A cleavage sequence, $^{503}$EREVPCH$^{509}$. The potential cleavage site, Cys-508, is located 6 amino acids from the beginning of the transmembrane domain and 32 amino acids from the C-terminus of MAVS. Cleavage at Cys-508 is predicted to generate an approximately 32-residue C-terminal fragment, consistent with the size difference between the mini-MAVS and the mini-MAVS lacking the TM domain (compare lane 4 & 5 of FIG. 22B, bottom panel). Indeed, when NS3/4A was co-transfected together with an expression construct encoding a MAVS protein that is tagged with FLAG at the N-terminus and HA at the C-terminus, the MAVS protein was cleaved into a soluble FLAG-tagged N-terminal fragment that was smaller than the intact protein (FIG. 22D, upper panel; compare lanes 1 & 4). Moreover, a C-terminal fragment of approximately 7 kDa in size was detectable in both the membrane pellet and cytosolic fractions with an HA antibody (FIG. 22D, middle panel; lanes 3 & 4). This cleavage product of MAVS was not detected in cells expressing the S139A mutant of NS3/4A. Although the apparent molecular mass of the C-terminal cleavage fragment was greater than the theoretical molecular mass of the fragment containing the C-terminal 32 residues of MAVS plus an HA epitope (approximately 5 kDa), this is likely due to the abnormal migration of small peptides on SDS-PAGE. Indeed, when the C-terminal 32 residues of MAVS (residue 509 to 540) plus the HA epitope was synthesized by in vitro translation, this fragment also migrated as an approximately 7 kDa band (FIG. 25A), identical to the C-terminal fragment of MAVS after cleavage by NS3/4A.

Figure 25B:
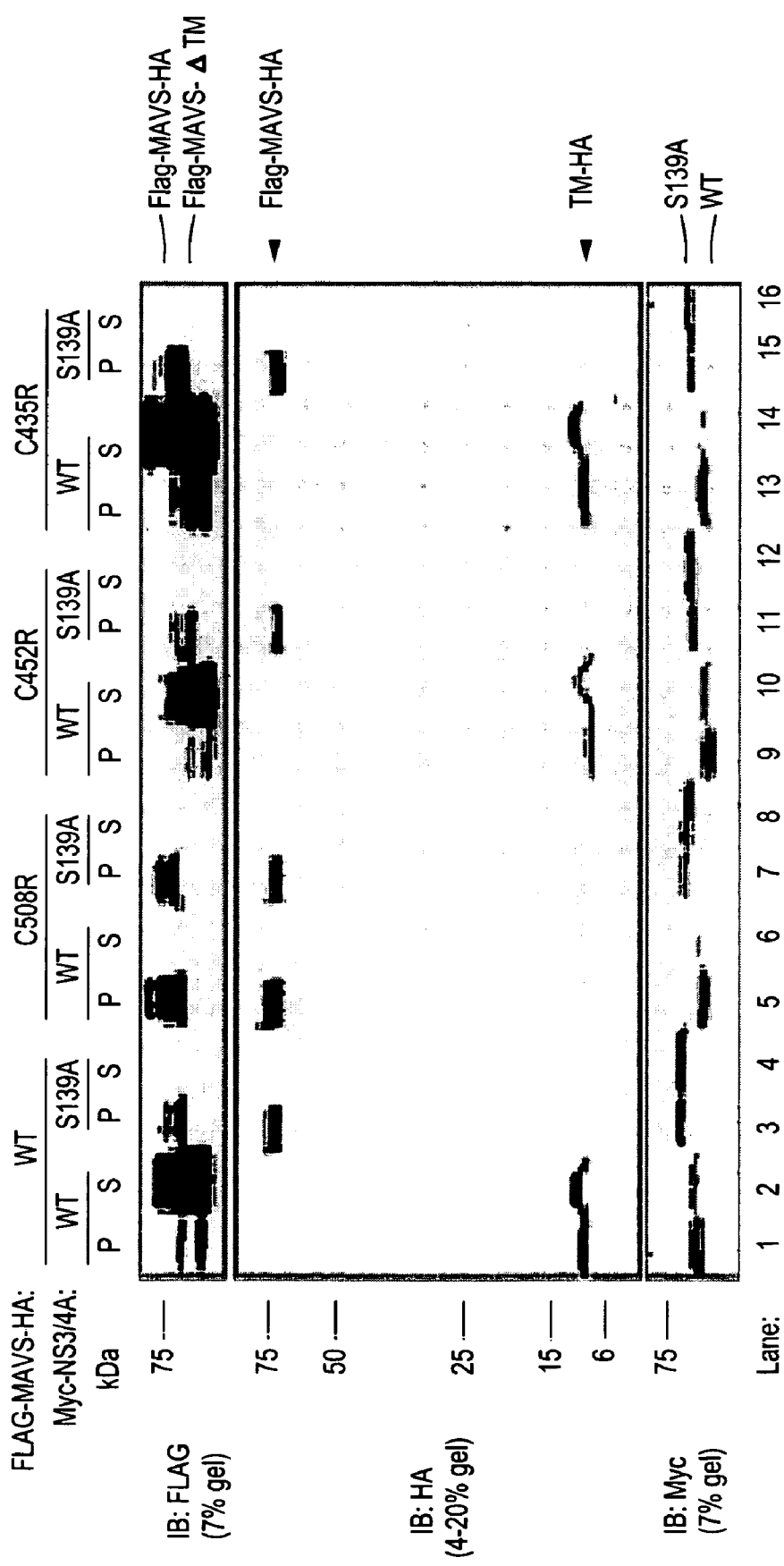

To demonstrate that Cys-508 is indeed the cleavage site, Cys-508 was mutated to Arg, which is predicted to disrupt NS3/4A cleavage based on the analysis of sequence requirement for HCV polyprotein cleavage (23). Remarkably, this single amino acid substitution completely blocked the cleavage of MAVS by NS3/4A (FIG. 22D, lanes 7-12). Furthermore, the protease-resistant mutant of MAVS was fully capable of inducing IFN-β, and this induction was no longer inhibited by NS3/4A (FIG. 22E). In contrast to Cys-508, mutations at two adjacent cysteines, Cys-435 and Cys452, did not prevent the cleavage of MAVS by NS3/4A (FIG. 25B). Taken together, these results indicate that NS3/4A cleaves MAVS at Cys-508 when these proteins are co-expressed in the same cells.

Figures 26A, 26B:
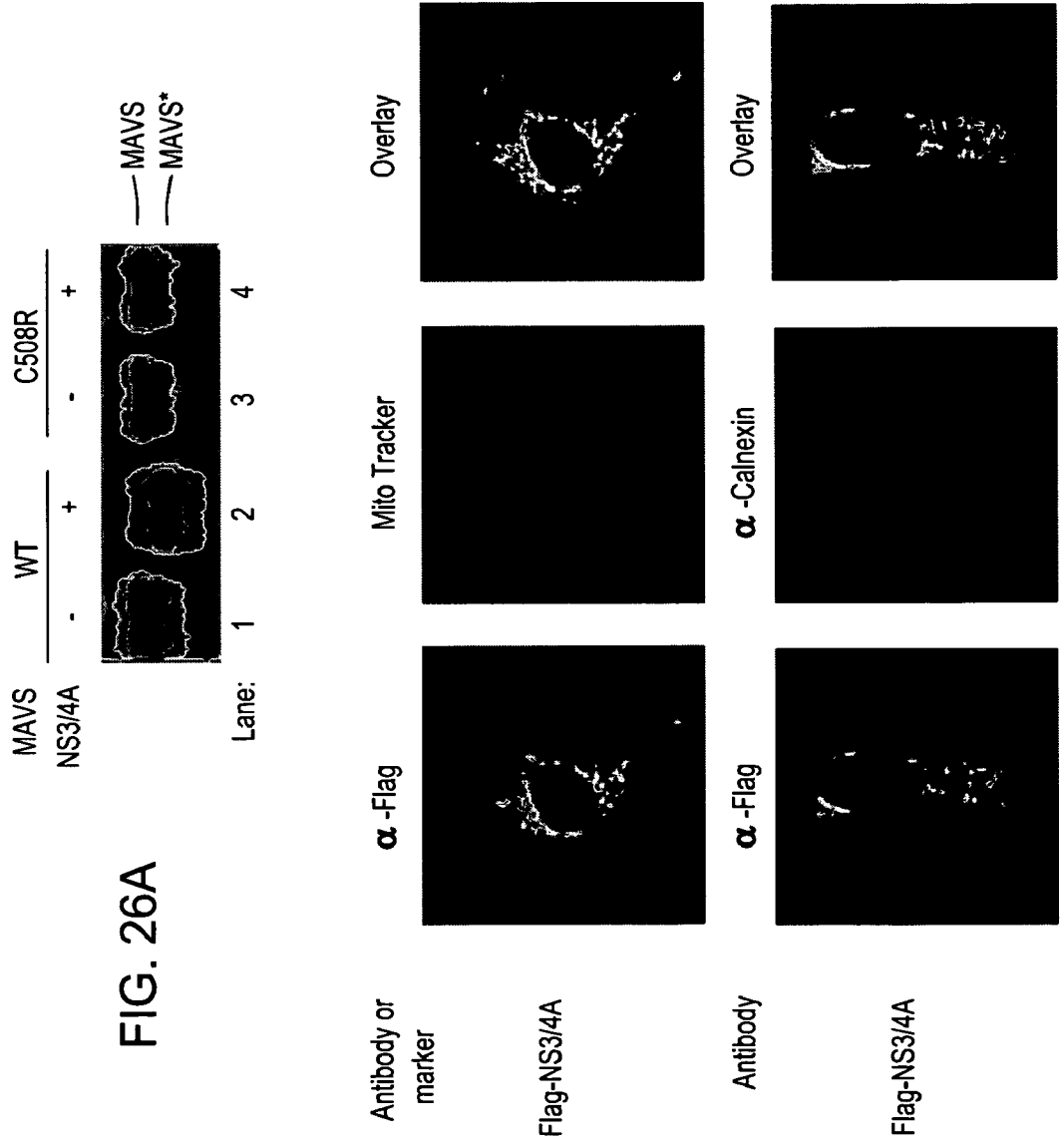

NS3/4A binds to and cleaves MAVS directly in vitro. To determine if NS3/4A could cleave MAVS directly in vitro, FLAG-NS3/4A or FLAG-NS3/4A (S139A) protein was expressed in HEK293 cells, and immunopurified the protein using the FLAG antibody followed by elution with a FLAG peptide. Also synthesized was an $^{35}$S-labeled FLAG-MAVS or FLAG-MAVS-C508R protein in vitro using rabbit reticulocyte lysates and purified the proteins using the FLAG antibody. The purified MAVS proteins were incubated with NS3/4A protease or lysates containing the protease. As shown in FIG. 23A, the wild type MAVS was cleaved by the active NS3/4A protease, but not the inactive NS3/4A mutant (lanes 1-5). In contrast, a point mutation at Cys-508 completely blocked the cleavage of MAVS by NS3/4A in vitro (lanes 6-10). The in vitro cleavage product represents the N-terminal fragment of MAVS, since the C-terminal 32 amino acid fragment does not contain any methionine that can be radioactively labeled. Similar results were obtained using NS3/4A protease expressed and purified from E. coli (FIG. 26A). These results indicate that NS3/4A directly cleaves MAVS at Cys-508 in vitro.

The cleavage of MAVS by NS3/4A suggests that these two proteins may interact directly. To investigate this possibility, MAVS and NS3/4A or their mutants were co-transfected into HEK293 cells, immunoprecipitated MAVS with the MAVS antibody, and then determined if NS3/4A was co-precipitated with MAVS by immunoblotting (FIG. 23B). Interestingly, only the S139A mutant, but not the wild type, NS3/4A co-precipitated with MAVS (compare lane 3 & 9), suggesting that the cleaved MAVS dissociated from the wild type protease, whereas the mutant protease was able to "trap" its substrate. Consistent with this interpretation, C508R also bound to either wild type or S139A mutant of NS3/4A, but this binding was weaker than that observed between MAVS and the S139A mutant of NS3/4A (compare lanes 6 & 12 with lane 9), suggesting that C508R mutation may partially impair its binding to the protease.

NS3/4A colocalizes with MAVS in the mitochondria. It has been shown that HCV core protein and NS3/4A are localized to a mitochondrion-associated membrane structure in both cultured hepatocytes (24, 25) and liver biopsies of chronic hepatitis C patients(26). Since MAVS is a mitochondrial membrane protein, whether MAVS and NS3/4A co-localize in the same membrane compartment was examined. Expression vectors encoding Myc-NS3/4A and/or HA-MAVS were transfected into HeLa cells, which were then stained with the corresponding antibodies followed by imaging with a laser scanning confocal microscope. To stain the mitochondria, cells were incubated with Mito Tracker, a fluorescent dye taken up by the mitochondria of living cells. The staining patterns of the wild type NS3/4A overlapped with that of Mito Tracker, but not the endoplasmic reticulum resident protein calnexin (FIG. 26B), suggesting that NS3/4A is localized to the mitochondria or in a mitochondrion-associated membrane. When the wild type NS3/4A and MAVS were co-expressed, the majority of MAVS became cytosolic (presumably due to cleavage), as revealed by an antibody that detects the N4-terminus of MAVS (FIG. 23C). In sharp contrast, when the wild type NS3/4A was co-expressed with MAVS-C508R, both NS3/4A and MAVS-C508R proteins co-localized in the mitochondrial membrane and showed an extensive overlapping staining pattern. These results indicate that MAVS and NS3/4A are co-localized in the mitochondrial membrane or are positioned in very close proximity, thus rendering MAVS vulnerable to cleavage by NS3/4A.

Figure 24A:
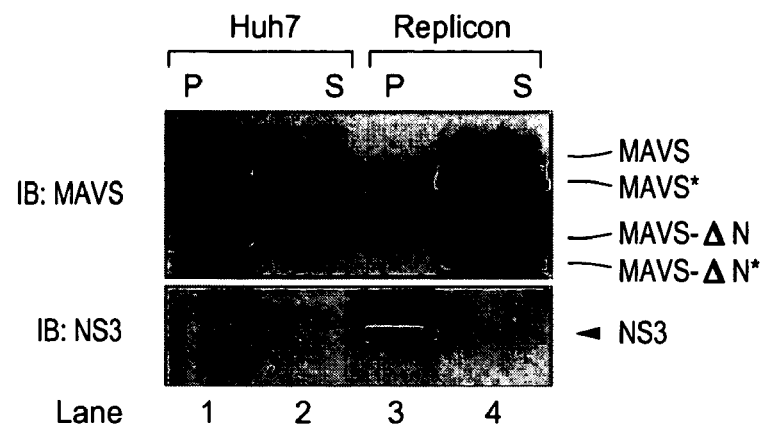

MAVS is cleaved in an HCV replicon cell line. To determine if MAVS is a target of HCV during viral replication, the HCV replicon cell culture system was used in which the subgenomic RNA of HCV replicates autonomously in the human hepatoma cell line Huh7(27). The HCV subgenomic RNA encodes all the nonstructural proteins, including the NS3/4A protease and the NS5B RNA polymerase. It has been shown previously that the HCV replicon cell lines that replicate the viral RNA efficiently can suppress the host interferon induction through the proteolytic activity of NS3/4A (3). To determine whether the endogenous MAVS is cleaved in the replicon cells, subcellular fractionation and immunoblotting were used to analyze the MAVS protein from the wild type Huh7 and a replicon cell line K2040 (19). As shown in FIG. 24A, the MAVS protein is present predominately in the mitochondrial membrane pellet isolated from Huh7 cells. In contrast, in the HCV replicon cells, a cleaved form of MAVS was found mostly in the soluble cytosolic fraction, whereas NS3 was detected mainly in the membrane pellets.

Figure 24B:
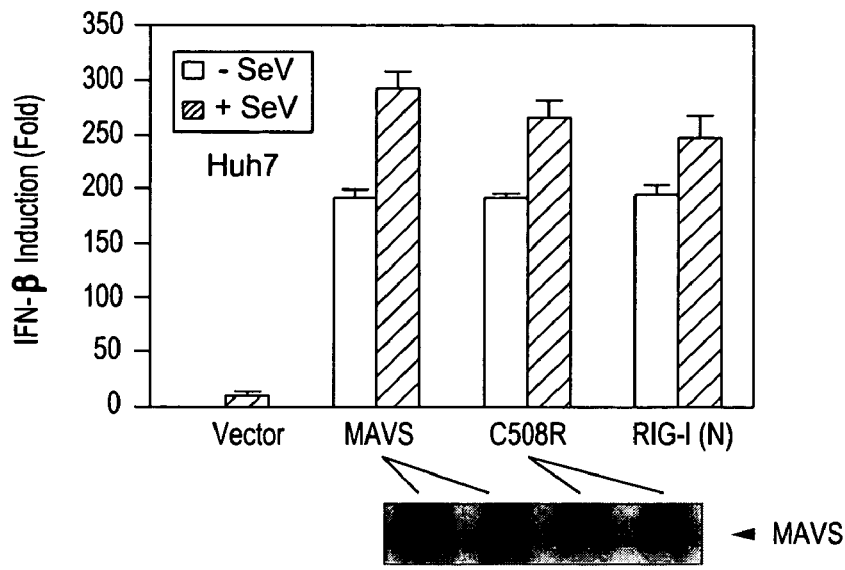
Figure 24C:
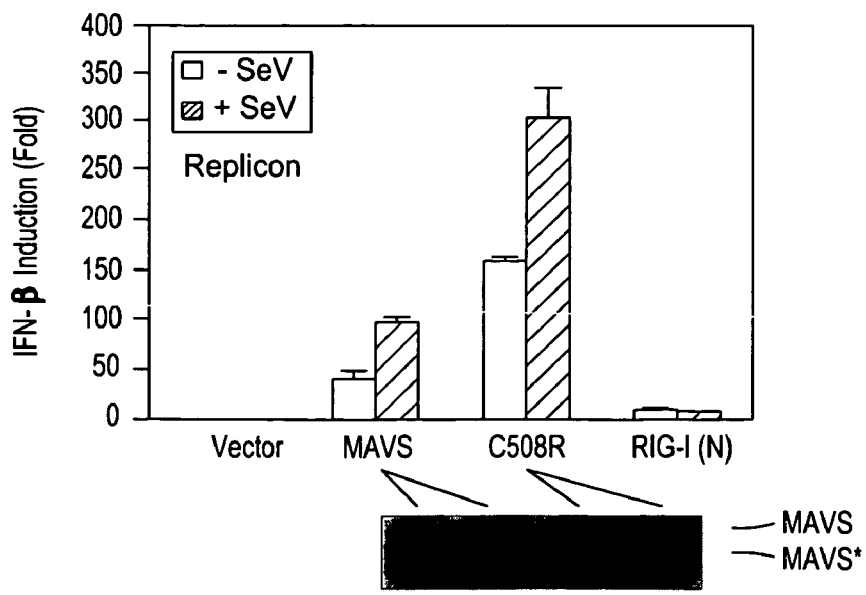

Prevention of MAVS cleavage restores the interferon response in HCV replicon cells. If the cleavage of MAVS is solely responsible for the failure to induce interferons in HCV replicon cells, prevention of MAVS cleavage should restore interferon induction in these cells. To address this question, the C508R mutant of MAVS was introduced as well as the wild type MAVS into the HCV replicon cells to examine the induction of IFN-β. As previously reported (3), Sendai virus induced IFN-β in the Huh7 cells, but failed to do so in the replicon cell line (FIGS. 24B & 24C). Even overexpression of RIG-I (N) failed to induce IFN-β in the replicon cells (FIG. 24C), presumably because the endogenous MAVS was cleaved into an inactive soluble fragment (FIG. 24A, lane 4). Overexpression of wild type MAVS was able to induce partial interferon response in the replicon cells, and this response was further enhanced by Sendai virus. This may be due to the incomplete cleavage of the overexpressed MAVS by the NS3/4A protease in the replicon cells. Most significantly, expression of the protease-resistant mutant of MAVS (C508R) restored IFN-β induction in the replicon cells to the same level observed in Huh7 cells (FIGS. 24B and 24C). These results demonstrate that the evasion of innate immune response in the HCV replicon cells is due to the cleavage of MAVS by NS3/4A.

The inventors have previously shown that MAVS is an essential antiviral signaling protein and proposed that MAVS may be a prime target of viruses that have succeeded in evading the host immune system (Seth, R. B., Sun, L., Ea, C. K. & Chen, Z. J. (2005) Cell 122, 669-82). In this Example, it is shown that MAVS is indeed the proteolytic target of HCV NS3/4A protease. Specifically, it was found that HCV cleaves MAVS at Cys-508, dislocating MAVS from the mitochondria, thus preventing the induction of interferon-β. NS3/4A binds to and colocalizes with MAVS at the mitochondrial membrane, and it can cleave MAVS at Cys-508 directly in vitro. These studies also provide direct evidence that the endogenous MAVS protein is cleaved in an HCV replicon cell line that failed to elicit interferon response. Importantly, a point mutation of MAVS at Cys-508 that prevents its cleavage restores interferon induction in the HCV replicon cell line. These results provide compelling evidence that MAVS is the prime target of the HCV protease. While our manuscript was in preparation, Meylan et al also reported the identification of MAVS/CARDIF as the target of NS3/4A (12). This example provides the direct biochemical evidence that MAVS is the proteolytic target of NS3/4A (FIG. 23) and shows that the cleavage of endogenous MAVS at Cys-508 in the HCV replicon cell line is solely responsible for the suppression of interferon induction in these cells (FIG. 24). Furthermore, the finding that NS3/4A inactivates MAVS by cleaving and dislodging it from the mitochondria underscores the importance of mitochondrial localization of MAVS in antiviral immunity.

Infectious diseases are a manifestation of constant battles between the host and pathogenic microbes. This host-pathogen antagonism is now vividly demonstrated from the study of the interaction between MAVS and HCV. MAVS can orchestrate strong immune defense against HCV; however, HCV counterattacks by using the NS3/4A protease to cleave MAVS, thus crippling the immune response. Since a point mutation at Cys-508 of MAVS completely prevents its cleavage by NS3/4A and preserves its antiviral activity, it would be interesting to determine whether there are sequence variations of MAVS in human population that confer differential sensitivity to NS3/4A, hence differential immunity to HCV. However, the prevalence of persistent HCV infection in humans suggests that HCV might have won the battle between the virus and the host. In the next battle of "our wits versus their genes", it may be possible to exploit the knowledge of MAVS-HCV interaction to fight back HCV. The cleavage of MAVS from the mitochondrial membrane serves as a diagnostic marker for an established HCV infection. Furthermore, using the compositions and methods of the present invention allow for the identification, isolation and characterization of agents that block the cleavage of MAVS by NS3/4A may be effective in the prevention and treatment of HCV.

HCV may not be the only pathogen that targets MAVS to evade the host immune system. Although the mitochondrial localization of MAVS may allow the host immune system to detect many viruses that replicate in intracellular membrane locations proximal to the mitochondria, it may also render MAVS vulnerable to viral attack. For example, it has recently been shown that the hepatitis A virus (HAV) inhibits interferon response at a step downstream of RIG-I but upstream of TBK1/IKKε (28), raising the possibility that MAVS may be a target of an HAV protein. These results and tools provided herein allow the skilled artisan to identify agents that affect the host-pathogen interaction that revolves around the battle for MAVS in order to gain control of the host immune system.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Akira, S., and Takeda, K. (2004). Toll-like receptor signalling. Nat Rev Immunol 4, 499-511.

Andrejeva, J., Childs, K. S., Young, D. F., Carlos, T. S., Stock, N., Goodbourn, S., and Randall, R. E. (2004). The V proteins of paramyxoviruses bind the IFN-inducible RNA helicase, mda-5, and inhibit its activation of the IFN-beta promoter. Proc Natl Acad Sci USA 101, 17264-17269.

Baeuerle, P. A., and Baltimore, D. (1988). Activation of DNA-binding activity in an apparently cytoplasmic precursor of the NF-kappa B transcription factor. Cell 53, 211-217.

Balachandran, S., Thomas, E., and Barber, G. N. (2004). A FADD-dependent innate immune mechanism in mammalian cells. Nature 432, 401-405.

Berg, R. E., Crossley, E., Murray, S., and Forman, J. (2003). Memory CD8+ T cells provide innate immune protection against Listeria monocytogenes in the absence of cognate antigen. J Exp Med 198, 1583-1593.

Bigger, C. B., Guerra, B., Brasky, K. M., Hubbard, G., Beard, M. R., Luxon, B. A., Lemon, S. M., and Lanford, R. E. (2004). Intrahepatic gene expression during chronic hepatitis C virus infection in chimpanzees. J Virol 78, 13779-13792.

Crozat, K., and .Beutler, B. (2004). TLR7: A new sensor of viral infection. Proc Natl Acad Sci U S A 101, 6835-6836.

Dalton, K. P., and Rose, J. K. (2001). Vesicular stomatitis virus glycoprotein containing the entire green fluorescent protein on its cytoplasmic domain is incorporated efficiently into virus particles. Virology 279, 414-421.

Darnell, J. E., Jr., Kerr, I. M., and Stark, G. R. (1994). Jak-STAT pathways and transcriptional activation in response to IFNs and other extracellular signaling proteins. Science 264, 1415-1421.

Deng, L., Wang, C., Spencer, E., Yang, L., Braun, A., You, J., Slaughter, C., Pickart, C., and Chen, Z. J. (2000). Activation of the IkappaB kinase complex by TRAF6 requires a dimeric ubiquitin-conjugating enzyme complex and a unique polyubiquitin chain. Cell 103, 351-361.

Diebold, S. S., Kaisho, T., Hemmi, H., Akira, S., and Reis e Sousa, C. (2004). Innate antiviral responses by means of TLR7-mediated recognition of single-stranded RNA. Science 303, 1529-1531.

Fitzgerald, K. A., McWhirter, S. M., Faia, K. L., Rowe, D. C., Latz, E., Golenbock, D. T., Coyle, A. J., Liao, S. M., and Maniatis, T. (2003). IKKepsilon and TBK1 are essential components of the IRF3 signaling pathway. Nat Immunol 4, 491-496.

Fitzgerald, K. A., McWhirter, S. M., Faia, K. L., Rowe, D. C., Latz, E., Golenbock, D. T., Coyle, A. J., Liao, S. M., and Maniatis, T. (2003). IKKepsilon and TBK1 are essential components of the IRF3 signaling pathway. Nat Immunol 4, 491-496.

Freundt, E. C., and Lenardo, M. J. (2005). Interfering with interferons: Hepatitis C virus counters innate immunity. Proc Natl Acad Sci USA 102, 17539-17540.

Heil, F., Hemmi, H., Hochrein, H., Ampenberger, F., Kirschning, C., Akira, S., Lipford, G., Wagner, H., and Bauer, S. (2004). Species-specific recognition of single-stranded RNA via toll-like receptor 7 and 8. Science 303, 1526-1529.

Hemmi, H., Takeuchi, O., Sato, S., Yamamoto, M., Kaisho, T., Sanjo, H., Kawai, T., Hoshino, K., Takeda, K., and Akira, S. (2004). The roles of two IkappaB kinase-related kinases in lipopolysaccharide and double stranded RNA signaling and viral infection. J Exp Med 199, 1641-1650.

Hiscott, J., Grandvaux, N., Sharma, S., Tenoever, B. R., Servant, M. J., and Lin, R. (2003). Convergence of the NF-kappaB and interferon signaling pathways in the regulation of antiviral defense and apoptosis. Ann N Y Acad Sci 1010, 237-248.

Hockenbery, D., Nunez, G., Milliman, C., Schreiber, R. D., and Korsmeyer, S. J. (1990). Bcl-2 is an inner mitochondrial membrane protein that blocks programmed cell death. Nature 348, 334-336.

Honda, K., Yanai, H., Negishi, H., Asagiri, M., Sato, M., Mizutani, T., Shimada, N., Ohba, Y., Takaoka, A., Yoshida, N., and Taniguchi, T. (2005). IRF-7 is the master regulator of type-I interferon-dependent immune responses. Nature 434, 772-777.

Honda, K., Yanai, H., Takaoka, A., and Taniguchi, T. (2005). Regulation of the type I IFN induction: a current view. Int Immunol 17, 1367-1378.

Hornung, V., Schlender, J., Guenthner-Biller, M., Rothenfusser, S., Endres, S., Conzelmann, K. K., and Hartmann, G. (2004). Replication-dependent potent IFN-alpha induction in human plasmacytoid dendritic cells by a single-stranded RNA virus. J Immunol 173, 5935-5943.

Inohara, N., del Peso, L., Koseki, T., Chen, S., and Nunez, G. (1998). RICK, a novel protein kinase containing a caspase recruitment domain, interacts with CLARP and regulates CD95-mediated apoptosis. J Biol Chem 273, 12296-12300.

Ishii, K. J., Coban, C., Kato, H., Takahashi, K., Torii, Y., Takeshita, F., Ludwig, H., Sutter, G., Suzuki, K., Hemmi, H., et al. (2006). A Toll-like receptor-independent antiviral response induced by double-stranded B-form DNA. Nat Immunol 7, 40-48.

Kang, D. C., Gopalkrishnan, R. V., Wu, Q., Jankowsky, E., Pyle, A. M., and Fisher, P. B. (2002). mda-5: An interferon-inducible putative RNA helicase with double-stranded RNA-dependent ATPase activity and melanoma growth-suppressive properties. Proc Natl Acad Sci USA 99, 637-642.

Kato, H., Sato, S., Yoneyama, M., Yamamoto, M., Uematsu, S., Matsui, K., Tsujimura, T., Takeda, K., Fujita, T., Takeuchi, O., and Akira, S. (2005). Cell Type-Specific Involvement of RIG-I in Antiviral Response. Immunity 23, 19-28.

Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature.

Kaufmann, T., Schlipf, S., Sanz, J., Neubert, K., Stein, R., and Borner, C. (2003). Characterization of the signal that directs Bcl-x(L), but not Bcl-2, to the mitochondrial outer membrane. J Cell Biol 160, 53-64.

Kawai, T., and Akira, S. (2006). Innate immune recognition of viral infection. Nat Immunol 7, 131-137.

Kawai, T., Sato, S., Ishii, K. J., Coban, C., Hemmi, H., Yamamoto, M., Terai, K., Matsuda, M., Inoue, J., Uematsu, S., et al. (2004). Interferon-alpha induction. through Toll-like receptors involves a direct interaction of IRF7 with MyD88 and TRAF6. Nat Immunol 5, 1061-1068.

Kawai, T., Takahashi, K., Sato, S., Coban, C., Kumar, H., Kato, H., Ishii, K. J., Takeuchi, O., and Akira, S. (2005). IPS-1, an adaptor triggering RIG-I- and Mda5-mediated type I interferon induction. Nat Immunol 6, 981-988.

Kim, P. K., Hollerbach, C., Trimble, W. S., Leber, B., and Andrews, D. W. (1999). Identification of the endoplasmic reticulum targeting signal in vesicle-associated membrane proteins. J Biol Chem 274, 36876-36882.

Kovacsovics, M., Martinon, F., Micheau, O., Bodmer, J. L., Hofmann, K., and Tschopp, J. (2002). Overexpression of Helicard, a CARD-containing helicase cleaved during apoptosis, accelerates DNA degradation. Curr Biol 12, 838-843.

Lamarre, D., Anderson, P. C., Bailey, M., Beaulieu, P., Bolger, G., Bonneau, P., Bos, M., Cameron, D. R., Cartier, M., Cordingley, M. G., et al. (2003). An NS3 protease inhibitor with antiviral effects in humans infected with hepatitis C virus. Nature 426, 186-189.

Lee, J., Wu, C. C., Lee, K. J., Chuang, T. H., Katakura, K., Liu, Y. T., Chan, M., Tawatao, R., Chung, M., Shen, C., et al. (2006). Activation of anti-hepatitis C virus responses via Toll-like receptor 7. Proc Natl Acad Sci USA 103, 1828-1833.

Levy, D. E. (2002). Whence interferon? Variety in the production of interferon in response to viral infection. J Exp Med 195, F15-18.

Li, X. D., Sun, L., Seth, R. B., Pineda, G., and Chen, Z. J. (2005). Hepatitis C virus protease NS3/4A cleaves mitochondrial antiviral signaling protein off the mitochondria to evade innate immunity. Proc Natl Acad Sci USA 102, 17717-17722.

Liu, Y. J. (2001). Dendritic cell subsets and lineages, and their functions in innate and adaptive immunity. Cell 106, 259-262.

Lund, J. M., Alexopoulou, L., Sato, A., Karow, M., Adams, N. C., Gale, N. W., Iwasaki, A., and Flavell, R. A. (2004). Recognition of single-stranded RNA viruses by Toll-like receptor 7. Proc Natl Acad Sci USA 101, 5598-5603.

Machida, K., Cheng, K. T., Sung, V. M., Levine, A. M., Foung, S., and Lai, M. M. (2006). Hepatitis C virus induces toll-like receptor 4 expression, leading to enhanced production of beta interferon and interleukin-6. J Virol 80, 866-874.

Maniatis, T., Falvo, J. V., Kim, T. H., Kim, T. K., Lin, C. H., Parekh, B. S., and Wathelet, M. G. (1998). Structure and function of the interferon-beta enhanceosome. Cold Spring Harb Symp Quant Biol 63, 609-620.

Matsuda, A., Suzuki, Y., Honda, G., Muramatsu, S., Matsuzaki, O., Nagano, Y., Doi, T., Shimotohno, K., Harada, T., Nishida, E., et al. (2003). Large-scale identification and characterization of human genes that activate NF-kappaB and MAPK signaling pathways. Oncogene 22, 3307-3318.

McWhirter, S. M., Fitzgerald, K. A., Rosains, J., Rowe, D. C., Golenbock, D. T., and Maniatis, T. (2004). IFN-regulatory factor 3-dependent gene expression is defective in Tbk1-deficient mouse embryonic fibroblasts. Proc Natl Acad Sci USA 101, 233-238.

McWhirter, S. M., Tenoever, B. R., and Maniatis, T. (2005). Connecting mitochondria and innate immunity. Cell 122, 645-647.

Meylan, E., Curran, J., Hofinann, K., Moradpour, D., Binder, M., Bartenschlager, R., and Tschopp, J. (2005). Cardif is an adaptor protein in the RIG-I antiviral pathway and is targeted by hepatitis C virus. Nature 437, 1167-1172.

Michaelson, D., Silletti, J., Murphy, G., D'Eustachio, P., Rush, M., and Philips, M. R. (2001). Differential localization of Rho GTPases in live cells: regulation by hypervariable regions and RhoGDI binding. J Cell Biol 152, 111-126.

O'Connell, R. M., Vaidya, S. A., Perry, A. K., Saha, S. K., Dempsey, P. W., and Cheng, G. (2005). Immune activation of type I IFNs by Listeria monocytogenes occurs independently of TLR4, TLR2, and receptor interacting protein 2 but involves TNFR-associated NF kappa B kinase-binding kinase 1. J Immunol 174, 1602-1607.

Oganesyan, G., Saha, S. K., Guo, B., He, J. Q., Shahangian, A., Zarnegar, B., Perry, A., and Cheng, G. (2006). Critical role of TRAF3 in the Toll-like receptor-dependent and -independent antiviral response. Nature 439, 208-211.

Okabe, Y., Kawane, K., Akira, S., Taniguchi, T., and Nagata, S. (2005). Toll-like receptor-independent gene induction program activated by mammalian DNA escaped from apoptotic DNA degradation. J Exp Med 202, 1333-1339.

O'Neill, L. A. (2004). Immunology. After the toll rush. Science 303, 1481-1482.

Perry, A. K., Chen, G., Zheng, D., Tang, H., and Cheng, G. (2005). The host type I interferon response to viral and bacterial infections. Cell Res 15, 407-422.

Perry, A. K., Chow, E. K., Goodnough, J. B., Yeh, W. C., and Cheng, 6. (2004). Differential requirement for TANK-binding kinase-1 in type I interferon responses to toll-like receptor activation and viral infection. J Exp Med 199, 1651-1658.

Rehermann, B., and Nascimbeni, M. (2005). Immunology of hepatitis B virus and hepatitis C virus infection. Nat Rev Immunol 5, 215-229.

Schwer, B., Ren, S., Pietschmann, T., Kartenbeck, J., Kaehlcke, K., Bartenschlager, R., Yen, T. S., and Ott, M. (2004). Targeting of hepatitis C virus core protein to mitochondria through a novel C-terminal localization motif. J Virol 78, 7958-7968.

Seth, R. B., Sun, L., and Chen, Z. J. (2006). Antiviral innate immunity pathways. Cell Res 16, 141-147.

Seth, R. B., Sun, L., Ea, C. K., and Chen, Z. J. (2005). Identification and characterization of MAVS, a mitochondrial antiviral signaling protein that activates NF-kappaB and IRF 3. Cell 122, 669-682.

Sharma, S., tenOever, B. R., Grandvaux, N., Zhou, G. P., Lin, R., and Hiscott, J. (2003). Triggering the interferon antiviral response through an IKK-related pathway. Science 300, 1148-1151.

Silverman, N., and Maniatis, T. (2001). NF-kappaB signaling pathways in mammalian and insect innate immunity. Genes Dev 15, 2321-2342.

Stetson, D. B., and Medzhitov, R. (2006). Recognition of cytosolic DNA activates an IRF3-dependent innate immune response. Immunity 24, 93-103.

Stockinger, S., Reutterer, B., Schaljo, B., Schellack, C., Brunner, S., Materna, T., Yamamoto, M., Akira, S., Taniguchi, T., Murray, P. J., et al. (2004). IFN regulatory factor 3-dependent induction of type I IFNs by intracellular bacteria is mediated by a TLR- and Nod2-independent mechanism. J Immunol 173, 7416-7425.

Sumpter, R., Jr., Loo, Y. M., Foy, E., Li, K., Yoneyama, M., Fujita, T., Lemon, S. M., and Gale, M., Jr. (2005). Regulating intracellular antiviral defense and permissiveness to hepatitis C virus RNA replication through a cellular RNA helicase, RIG-I. J Virol 79, 2689-2699.

Sun, L., and Chen, Z. J. (2004). The novel functions of ubiquitination in signaling. Curr Opin Cell Biol 16, 119-126.

ven Oers, B. R., Sharma, S., Zou, W., Sun, Q., Grandvaux, N., Julkunen, I., Hemmi, H., Yamamoto, M., Akira, S., Yeh, W. C., et al. (2004). Activation of TBK1 and IKKvarepsilon kinases by vesicular stomatitis virus infection and the role of viral ribonucleoprotein in the development of interferon antiviral immunity. J Virol 78, 10636-10649.

van Oers, N. S., and Chen, Z. J. (2005). Cell biology. Kinasing and clipping down the NF-kappa B trail. Science 308, 65-66.

Wang, X. (2001). The expanding role of mitochondria in apoptosis. Genes Dev 15, 2922-2933.

Wieland, S. F., and Chisari, F. V. (2005). Stealth and cunning: hepatitis B and hepatitis C viruses. J Virol 79, 9369-9380.

Xu, L. G., Wang, Y. Y., Han, K. J., Li, L. Y., Zhai, Z., and Shu, H. B. (2005). VISA Is an Adapter Protein Required for Virus-Triggered IFN-beta Signaling. Mol Cell 19, 727-740.

Ye, H., Arron, J. R., Lamothe, B., Cirilli, M;, Kobayashi, T., Shevde, N. K., Segal, D., Dzivenu, O. K., Vologodskaia, M., Yim, M., et al. (2002). Distinct molecular mechanism for initiating TRAF6 signalling. Nature 418, 443-447.

Yoneyama, M., Kikuchi, M., Natsukawa, T., Shinobu, N., Imaizumi, T., Miyagishi, M., Taira, K., Akira, S., and Fujita, T. (2004). The RNA helicase RIG-I has an essential function in double-stranded RNA-induced innate antiviral responses. Nat Immunol 5, 730-737.

Yoneyama, M., Suhara, W., and Fujita, T. (2002). Control of IRF-3 activation by phosphorylation. J Interferon Cytokine Res 22, 73-76.

What is claimed is:

1. A polynucleotide that encodes a mitochondrial anti-viral signaling protein encoded by the nucleic acid as set forth by SEQ ID NO. 1.

2. The polynucleotide of claim 1, further defined as DNA.

3. The polynucleotide of claim 1, operably linked to a promoter.

4. The polynucleotide of claim 1, operably linked to a promoter, wherein the promoter is selected from the group consisting of a polyoma, Adenovirus 2, Simian Virus 40, β-lactamase, MAVS, lac, tac, trp, Osf, Runt, 3-phosphoglycerate kinase, enolase, alcohol dehydrogenase 2, isocytochrome C, acid phosphatase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase promoter.

5. The polynucleotide of claim 1, further comprising a vector.

6. The polynucleotide of claim 1, further comprising a vector wherein the vector is a plasmid or viral vector.

7. The polynucleotide of claim 1, comprising the contiguous nucleic acid sequence of SEQ ID NO:1.

8. An isolated host cell comprising a vector that expresses a mitochondrial anti-viral signaling protein encoded by the nucleic acid as set forth by SEQ ID NO. 1.

9. The host cell of claim 8, wherein the host cell is a prokaryotic cell or a eukaryotic cell.

10. The host cell of claim 8, further defined as a bacterial, fungal or animal host cell.

11. The host cell of claim 8, comprised within a non-human transgenic animal.

12. The host cell of claim 8, wherein the host cell expresses the mitochondrial anti-viral signaling protein.

* * * * *

UNITED STATES PATENT AND TRADEMARK OFFICE
CERTIFICATE OF CORRECTION

| | | |
|---|---|---|
| PATENT NO. | : 7,625,724 B2 | Page 1 of 1 |
| APPLICATION NO. | : 11/509924 | |
| DATED | : December 1, 2009 | |
| INVENTOR(S) | : Zhijian J. Chen et al. | |

It is certified that error appears in the above-identified patent and that said Letters Patent is hereby corrected as shown below:

Col. 2, line 45
Replace "and IRF3. is currently not" with --and IRF3 is currently not--

Col. 4, line 25
Replace "obtaining a cellular samples" with --obtaining cellular samples--

Col. 5, line 11
Replace "binds to an mitochondrial" with --binds to a mitochondrial--

Col. 5, line 16
Replace "expression mitochondrial anti-viral" with --expression of the mitochondrial anti-viral--

Col. 19, line 20
Replace "an oligonucleotides referred to" with --an oligonucleotide is referred to--

Col. 21, line 36
Replace "The designation. (-)" with --The designation (-)--

Col. 23, line 26
Replace "to be sorted oat from" with --to be sorted out from--

Col. 27, line 23
Replace "human genes. XV" with --human genes XV--

Col. 43, line 23
Replace "Interestingly, nornal levels of" with --Interestingly, normal levels of--

Signed and Sealed this
Twenty-third Day of August, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 1623
<212> TYPE: DNA
<213> ORGANISM: Homo sapiens

<400> SEQUENCE: 1

```
atgccgtttg ctgaagacaa gacctataag tatatctgcc gcaatttcag caattttgc      60
aatgtggatg ttgtagagat tctgccttac ctgccctgcc tcacagcaag agaccaggat    120
cgactgcggg ccacctgcac actctcaggg aaccgggaca ccctctggca tctcttcaat    180
acccttcagc ggcggcccgg ctgggtggag tacttcattg cggcactgag gggctgtgag    240
ctagttgatc tcgcggacga agtggcctct gtctacgaga gctaccagcc tcggacctcg    300
gaccgtcccc cagacccact ggagccaccg tcacttcctg ctgagaggcc agggccccc     360
acacctgctg cggcccacag catcccctac aacagctgca gagagaagga gccaagttac    420
cccatgcctg tccaggagac ccaggcgcca gagtccccag agagaattc agagcaagcc     480
ctgcagacgc tcagccccag agccatccca aggaatccag atggtggccc cctggagtcc    540
tcctctgacc tggcagccct cagccctctg acctccagcg gcatcagga aaggacaca     600
gaactgggca gtacccacac agcaggtgcg acctccagcc tcacaccatc ccgtgggcct    660
gtgtctccat ctgtctcctt ccagcccctg gcccgttcca cccccagggc aagccgcttg    720
cctggaccca gggtcagt tgtatctact ggcacctcct tctcctcctc atcccctggc     780
ttggcctctg cagggctgc agagggtaaa cagggtgcag agagtgacca ggccgagcct    840
atcatctgct ccagtggggc agaggcacct gccaactctc tgccctccaa agtgcctacc    900
accttgatgc ctgtgaacac agtggccctg aaagtgcctg ccaacccagc atctgtcagc    960
acagtgccct ccaagttgcc aactagctca agccccctg gtgcagtgcc ttctaatgcg    1020
ctcaccaatc cagcaccatc caaattgccc atcaactcaa cccgtgctgg catggtgcca   1080
tccaaagtgc ctactagcat ggtgctcacc aaggtgtctg ccagcacagt ccccactgac   1140
gggagcagca gaaatgagga gcccccagca gctccaacac ccgccggcgc cactggaggc   1200
agctcagcct ggctagacag cagctttgag aatagggggcc ttgggtcgga gctgagtaag   1260
cctggcgtgc tggcatccca gtagacagc ccgttctcgg gctgcttcga ggatcttgcc    1320
atcagtgcca gcacctcctt gggcatgggg ccctgccatg cccagagga gaatgagtat    1380
aagtccgagg gcacctttgg gatccacgtg gctgagaacc ccagcatcca gctcctggag   1440
ggcaaccctg ggccacctgc ggacccgat ggcggcccca ggccacaagc cgaccggaag    1500
ttccaggaga gggaggtgcc atgccacagg ccctcacctg gggctctgtg gctccaggtg   1560
gctgtgacag gggtgctggt agtcacactc ctggtggtgc tgtaccggcg gcgtctgcac   1620
tag                                                                  1623
```

<210> SEQ ID NO 2
<211> LENGTH: 540
<212> TYPE: PRT
<213> ORGANISM: Homo sapiens

<400> SEQUENCE: 2

```
Met Pro Phe Ala Glu Asp Lys Thr Tyr Lys Tyr Ile Cys Arg Asn Phe
 1               5                  10                  15
```

-continued

```
Ser Asn Phe Cys Asn Val Asp Val Glu Ile Leu Pro Tyr Leu Pro
         20                  25                  30

Cys Leu Thr Ala Arg Asp Gln Asp Arg Leu Arg Ala Thr Cys Thr Leu
         35                  40                  45

Ser Gly Asn Arg Asp Thr Leu Trp His Leu Phe Asn Thr Leu Gln Arg
 50                  55                  60

Arg Pro Gly Trp Val Glu Tyr Phe Ile Ala Ala Leu Arg Gly Cys Glu
 65                  70                  75                  80

Leu Val Asp Leu Ala Asp Glu Val Ala Ser Val Tyr Glu Ser Tyr Gln
                 85                  90                  95

Pro Arg Thr Ser Asp Arg Pro Asp Pro Leu Glu Pro Pro Ser Leu
                100                 105                 110

Pro Ala Glu Arg Pro Gly Pro Thr Pro Ala Ala His Ser Ile
                115                 120                 125

Pro Tyr Asn Ser Cys Arg Glu Lys Glu Pro Ser Tyr Pro Met Pro Val
                130                 135                 140

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
                180                 185                 190

Ser Gly His Gln Glu Lys Asp Thr Glu Leu Gly Ser Thr His Thr Ala
                195                 200                 205

Gly Ala Thr Ser Ser Leu Thr Pro Ser Arg Gly Pro Val Ser Pro Ser
                210                 215                 220

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
                245                 250                 255

Ser Ser Pro Gly Leu Ala Ser Ala Gly Ala Ala Glu Gly Lys Gln Gly
                260                 265                 270

Ala Glu Ser Asp Gln Ala Glu Pro Ile Ile Cys Ser Ser Gly Ala Glu
                275                 280                 285

Ala Pro Ala Asn Ser Leu Pro Ser Lys Val Pro Thr Thr Leu Met Pro
                290                 295                 300

Val Asn Thr Val Ala Leu Lys Val Pro Ala Asn Pro Ala Ser Val Ser
305                 310                 315                 320

Thr Val Pro Ser Lys Leu Pro Thr Ser Ser Lys Pro Pro Gly Ala Val
                325                 330                 335

Pro Ser Asn Ala Leu Thr Asn Pro Ala Pro Ser Lys Leu Pro Ile Asn
                340                 345                 350

Ser Thr Arg Ala Gly Met Val Pro Ser Lys Val Pro Thr Ser Met Val
                355                 360                 365

Leu Thr Lys Val Ser Ala Ser Thr Val Pro Thr Asp Gly Ser Ser Arg
                370                 375                 380

Asn Glu Glu Thr Pro Ala Ala Pro Thr Pro Ala Gly Ala Thr Gly Gly
385                 390                 395                 400

Ser Ser Ala Trp Leu Asp Ser Ser Phe Glu Asn Arg Gly Leu Gly Ser
                405                 410                 415

Glu Leu Ser Lys Pro Gly Val Leu Ala Ser Gln Val Asp Ser Pro Phe
                420                 425                 430

Ser Gly Cys Phe Glu Asp Leu Ala Ile Ser Ala Ser Thr Ser Leu Gly
```

```
            435                 440                 445
Met Gly Pro Cys His Gly Pro Glu Glu Asn Glu Tyr Lys Ser Glu Gly
    450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
                485                 490                 495

Ala Asp Arg Lys Phe Gln Glu Arg Glu Val Pro Cys His Arg Pro Ser
            500                 505                 510

Pro Gly Ala Leu Trp Leu Gln Val Ala Val Thr Gly Val Leu Val Val
        515                 520                 525

Thr Leu Leu Val Val Leu Tyr Arg Arg Arg Leu His
    530                 535                 540

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 3
gcagaagaac ggcaucaag                                                 19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 4
aauucaucag agauaguca                                                 19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 5
ccaccuugau gccugugaa                                                 19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 6
cagaggagaa ugaguauaa                                                 19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
```

Oligonucleotide

<400> SEQUENCE: 7
cacgacagct ctttccatga                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
agccagtgct cgatgaatct                                               20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
atgaaggtct ccgcggcacg cct                                           23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
ctagctcatc tccaaagagt tg                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
aaaatcaagt ggggcgatgc t                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
gggcagagat gatgaccctt t                                             21

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 13
tcctgacgtt gaagt                                                15

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
agttgagggg actttcccag g                                         21
```